US010092720B2

(12) United States Patent
Kooij et al.

(10) Patent No.: US 10,092,720 B2
(45) Date of Patent: Oct. 9, 2018

(54) UNOBTRUSIVE INTERFACE SYSTEMS

(75) Inventors: Michiel Kooij, Amsterdam (NL); Paul Jan Klasek, Bonnyrigg Heights (AU); Adam Vivian Benjafield, Thornleigh (AU); Peter John Sweeney, Greenwich (AU); Richard Sokolov, Earlwood (AU); Philip Rodney Kwok, Chatswood (AU); Gerard Michael Rummery, Woodford (AU); Scott Alexander Howard, Frenchs Forest (AU); Robert Edward Henry, Baulkham Hills (AU); Renee Frances Doherty, Eastwood (AU); Enrico Brambilla, Drummoyne (AU); Dieter Heidmann, Cherrybrook (AU); Glenn Richards, Clevedon (NZ); Ian Frederick Johnson, Pennant Hills (AU)

(73) Assignee: ResMed Limited, Bella Vista (AU)

( * ) Notice: Subject to any disclaimer, the term of this patent is extended or adjusted under 35 U.S.C. 154(b) by 874 days.

(21) Appl. No.: 12/920,969

(22) PCT Filed: Mar. 4, 2009

(86) PCT No.: PCT/AU2009/000263
§ 371 (c)(1),
(2), (4) Date: Nov. 24, 2010

(87) PCT Pub. No.: WO2009/109005
PCT Pub. Date: Sep. 11, 2009

(65) Prior Publication Data
US 2011/0067704 A1 Mar. 24, 2011

Related U.S. Application Data

(60) Provisional application No. 61/058,659, filed on Jun. 4, 2008, provisional application No. 61/080,847, filed on Jul. 15, 2008.

(30) Foreign Application Priority Data

Mar. 4, 2008 (AU) ................................ 2008901055

(51) Int. Cl.
*A61M 16/00* (2006.01)
*A61M 16/06* (2006.01)
*A61M 16/08* (2006.01)

(52) U.S. Cl.
CPC .... *A61M 16/0666* (2013.01); *A61M 16/0672* (2014.02); *A61M 16/0683* (2013.01);
(Continued)

(58) Field of Classification Search
CPC ...... A61M 16/06–16/0694; A61M 2016/0661; A62B 7/00; A62B 7/14; A62B 18/00;
(Continued)

(56) References Cited

U.S. PATENT DOCUMENTS 3,754,552 A * 8/1973 King ......................... 128/207.18
3,814,103 A * 6/1974 Fettel et al. ............. 128/207.18
(Continued)

FOREIGN PATENT DOCUMENTS

EP 2022528 A2 2/2009
WO WO 2000/064521 11/2000
(Continued)

OTHER PUBLICATIONS

International Search Report for PCT/AU2009/000263, dated Aug. 20, 2009.
(Continued)

*Primary Examiner* — Gregory Anderson
*Assistant Examiner* — Ned T Heffner
(74) *Attorney, Agent, or Firm* — Nixon & Vanderhye P.C.

(57) ABSTRACT

An apparatus for delivering a flow of breathable gas to a patient for the treatment of Sleep Disordered Breathing
(Continued)

(SDB) that is less obtrusive includes a nasal cannula, cannulae (2a, 2b), prongs, or pillows and may be sealed or unsealed with the nares of the patient in use. The cannula, pillows or prongs may be positioned on the face of the patient by a headgear (6). The cannula, pillows or prongs may be smaller, lighter, and/or less visible than other nasal cannula, cannulae, pillows or prongs and may therefore be less obtrusive to the patient.

45 Claims, 58 Drawing Sheets

(52) U.S. Cl.
CPC .... *A61M 16/0816* (2013.01); *A61M 16/0858* (2014.02); *A61M 16/0866* (2014.02)

(58) Field of Classification Search
CPC ......... A62B 18/02; A62B 18/04; A62B 18/06; A62B 18/08–18/088; B63C 11/12; B63C 11/18
USPC ............ 128/200.24, 200.26, 203.22, 206.11, 128/207.13, 207.18
See application file for complete search history.

(56) References Cited

U.S. PATENT DOCUMENTS

| | | | |
|---|---|---|---|
| 4,052,990 A * | 10/1977 | Dodgson | 128/207.14 |
| 4,149,556 A * | 4/1979 | Schwabe | 137/115.01 |
| 4,708,831 A * | 11/1987 | Elsworth et al. | 261/130 |
| 4,753,233 A | 6/1988 | Grimes | |
| 4,944,310 A | 7/1990 | Sullivan | |
| 4,971,050 A * | 11/1990 | Bartos | A61M 16/00 128/204.18 |
| 5,009,227 A * | 4/1991 | Nieuwstad | 128/207.17 |
| 5,320,092 A | 6/1994 | Ryder | |
| 5,513,634 A | 5/1996 | Jackson | |
| 5,600,752 A * | 2/1997 | Lopatinsky | 392/488 |
| 6,050,260 A | 4/2000 | Daniell et al. | |
| 6,536,436 B1 | 3/2003 | McGlothen | |
| 7,047,972 B2 * | 5/2006 | Ging et al. | 128/207.11 |
| 7,080,645 B2 | 7/2006 | Genger et al. | |
| 7,318,437 B2 | 1/2008 | Gunaratnam et al. | |
| 2003/0209246 A1 | 11/2003 | Schroeder et al. | |
| 2004/0200476 A1 | 10/2004 | Bamford | |
| 2004/0226566 A1 * | 11/2004 | Gunaratnam et al. | 128/207.18 |
| 2004/0245658 A1 | 12/2004 | Niland et al. | |
| 2004/0261797 A1 | 12/2004 | White et al. | |
| 2005/0011523 A1 | 1/2005 | Aylsworth et al. | |
| 2005/0034730 A1 | 2/2005 | Wood | |
| 2006/0028346 A1 | 2/2006 | White | |
| 2006/0283461 A1 | 12/2006 | Lubke et al. | |
| 2007/0144525 A1 | 6/2007 | Davidson et al. | |
| 2008/0047560 A1 | 2/2008 | Veliss et al. | |
| 2008/0060649 A1 | 3/2008 | Veliss et al. | |
| 2008/0105257 A1 * | 5/2008 | Klasek | A61M 16/161 128/203.27 |
| 2009/0078259 A1 | 3/2009 | Kooij et al. | |
| 2009/0223514 A1 | 9/2009 | Smith et al. | |

FOREIGN PATENT DOCUMENTS

| | | | |
|---|---|---|---|
| WO | 2004/073778 A1 | 9/2004 | |
| WO | WO 2005/018524 | 3/2005 | |
| WO | 2006130903 | 12/2006 | |
| WO | 2007/053878 A1 | 5/2007 | |
| WO | 2008/007985 | 1/2008 | |
| WO | WO 2008/019294 | 2/2008 | |
| WO | WO 2009/052560 A1 | 4/2009 | |
| WO | 2009/109005 | 9/2009 | |
| WO | WO 2009/146484 A1 | 12/2009 | |
| WO | 2011/068418 | 6/2011 | |
| WO | 2011/078703 | 6/2011 | |
| WO | 2012/164407 | 6/2012 | |

OTHER PUBLICATIONS

International Preliminary Report on Patentability dated Sep. 16, 2010 in International Application No. PCT/AU2009/000263.
Further Examination Report dated Nov. 12, 2015 issued in New Zealand Application No. 623338 (2 pages).
Further Examination Report dated May 1, 2014 in New Zealand Application No. 605600 (2 pages).
First Examination Report dated May 1, 2014 in New Zealand Application No. 623338 (2 pages).
First Examination Report dated Nov. 12, 2015 issued in New Zealand Application No. 713510 (2 pages).
Further Examination Report dated Feb. 24, 2017 issued in New Zealand Application No. 713510 (3 pages).
Further Examination Report dated May 29, 2017 issued in New Zealand Application No. 713510 (2 pages).
First Examination Report dated May 30, 2017 issued in New Zealand Application No. 731481 (2 pages).
Proceeding Correspondence dated Dec. 14, 2016 issued in New Zealand Application No. 623338 (4 pages).
First Amended Statement of Case dated Dec. 6, 2016 filed in New Zealand Application No. 623338 with track changes (19 pages).
First Amended Statement of Case dated Dec. 6, 2016 filed in New Zealand Application No. 623338 without mark ups (19 pages).
Examination Report dated May 17, 2017 issued in German Application No. 11 2009 000 517.9 with English translation (16 pages).

* cited by examiner

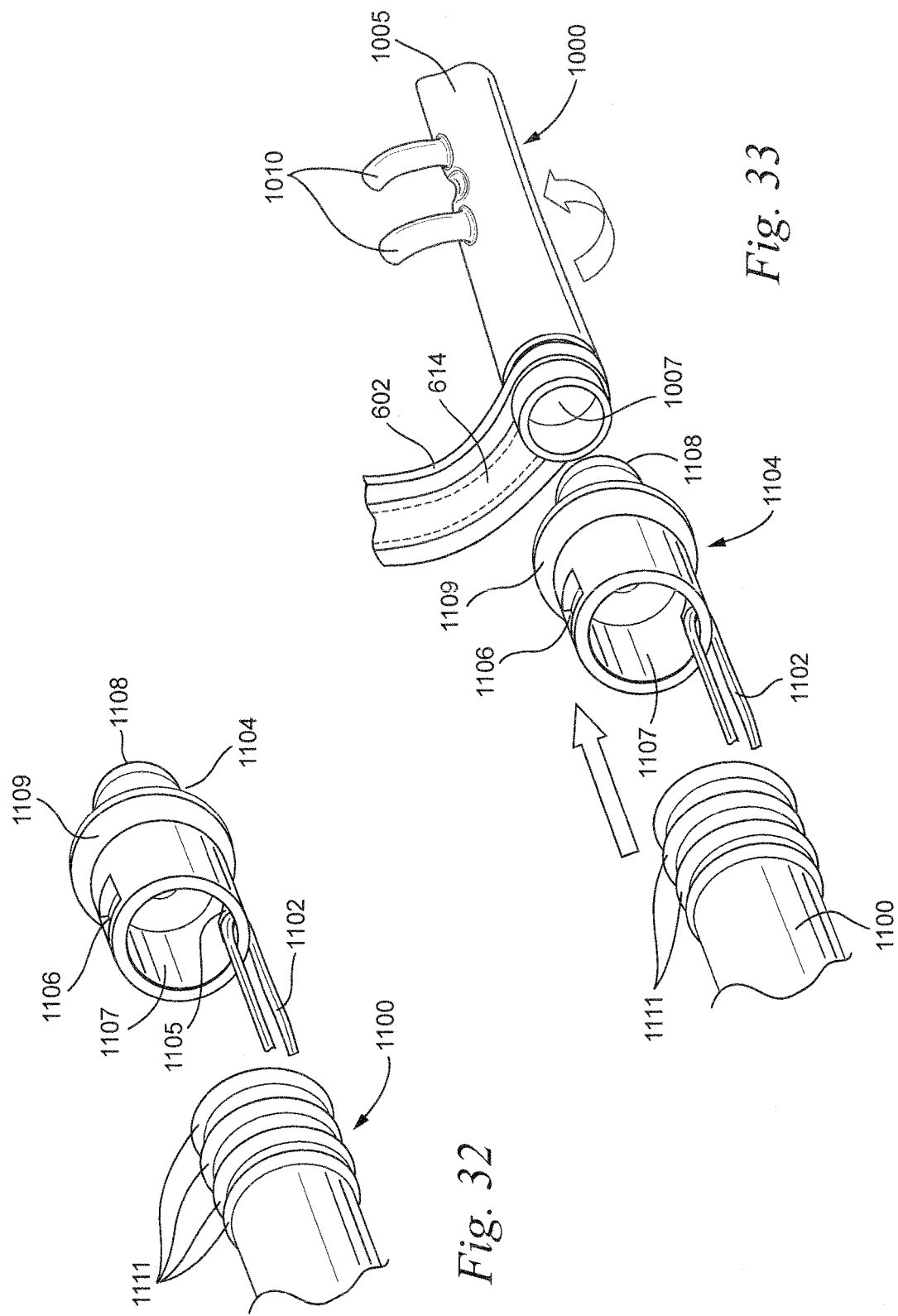

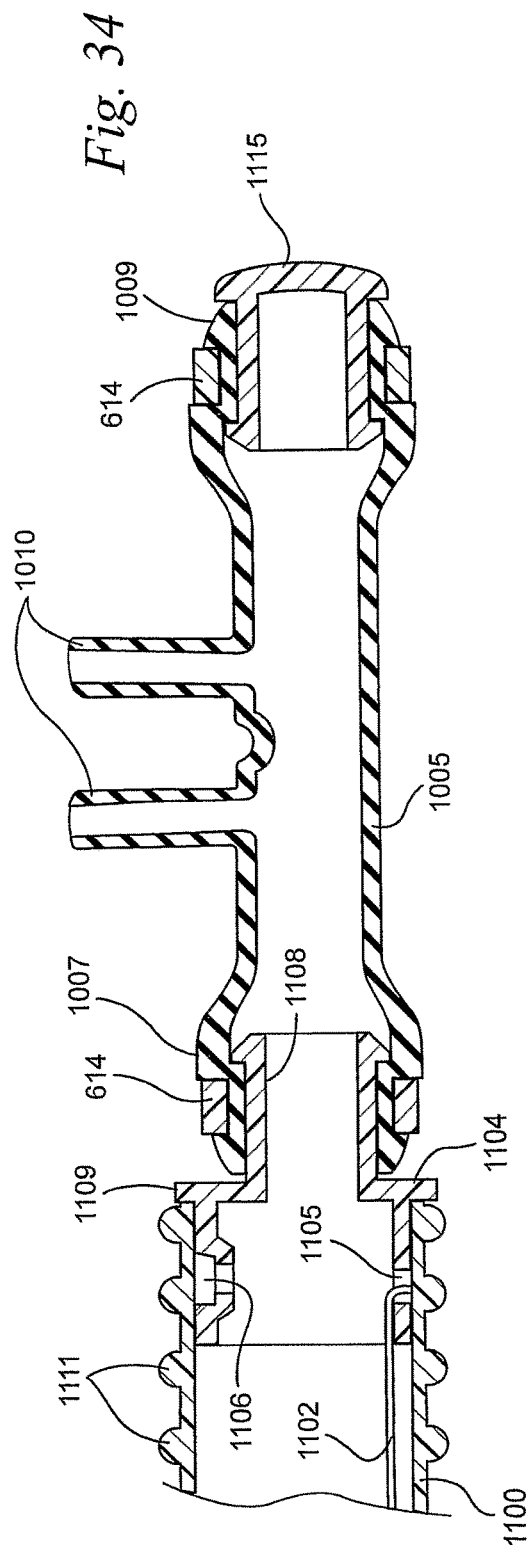
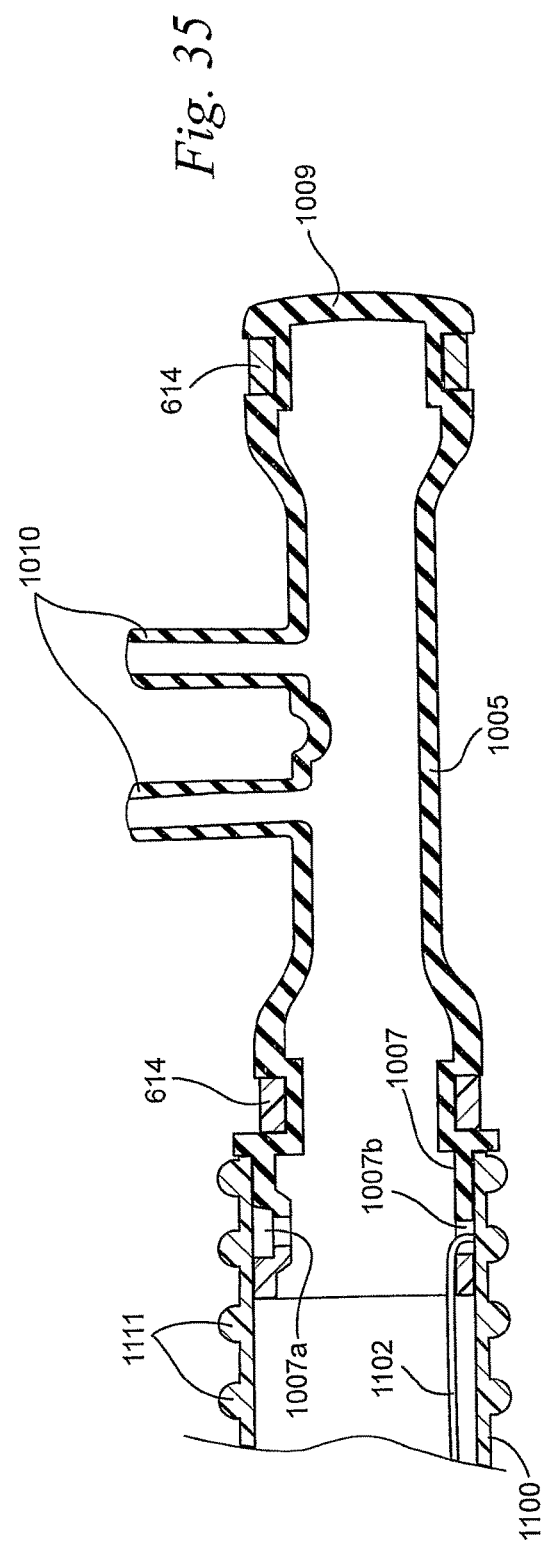

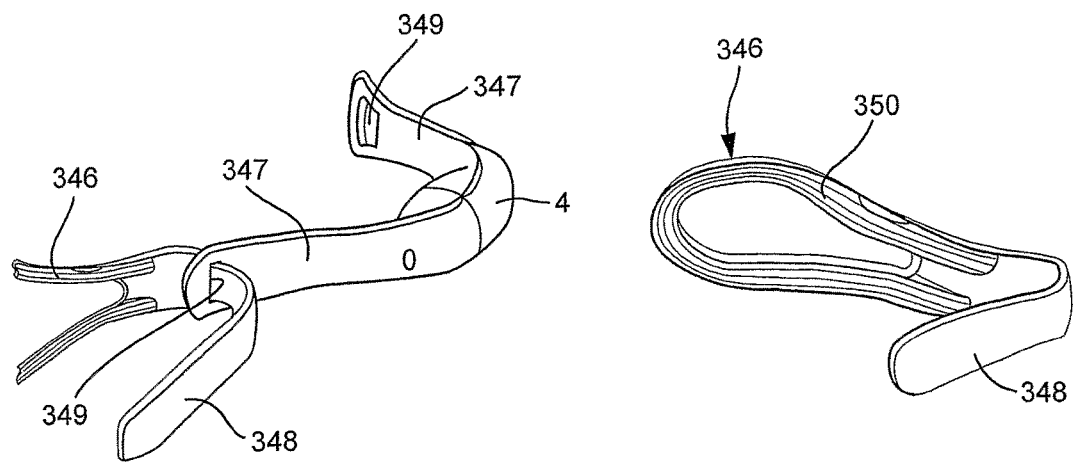
*Fig. 51a*  *Fig. 51b*
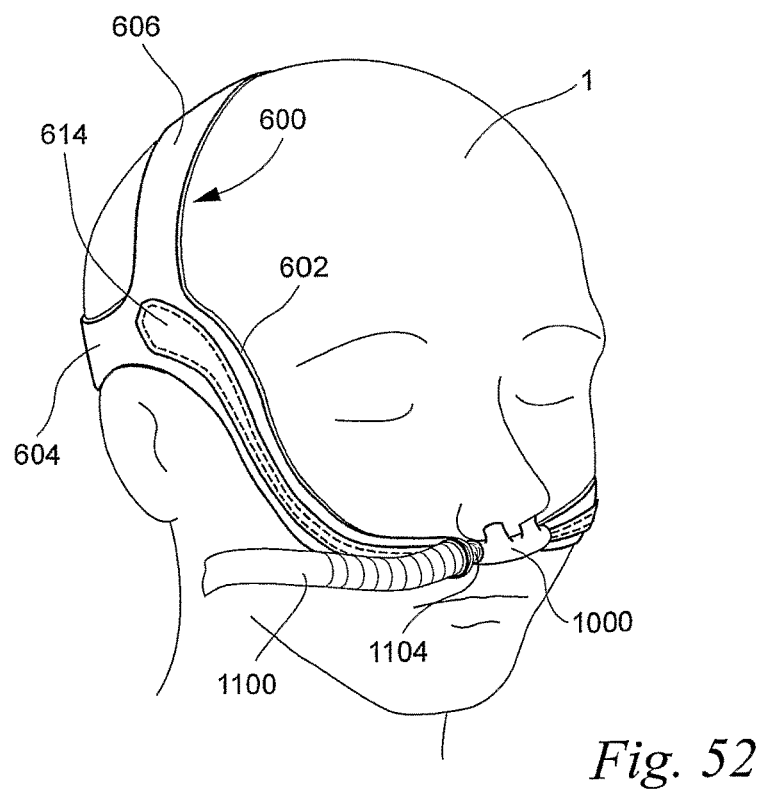
*Fig. 52*

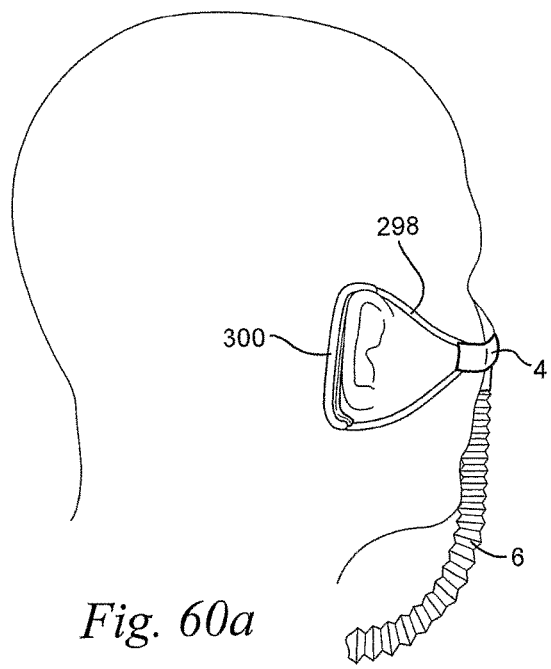
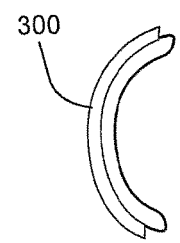
*Fig. 60c*
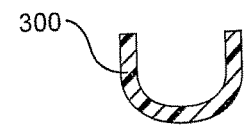
*Fig. 60d*
*Fig. 60a*
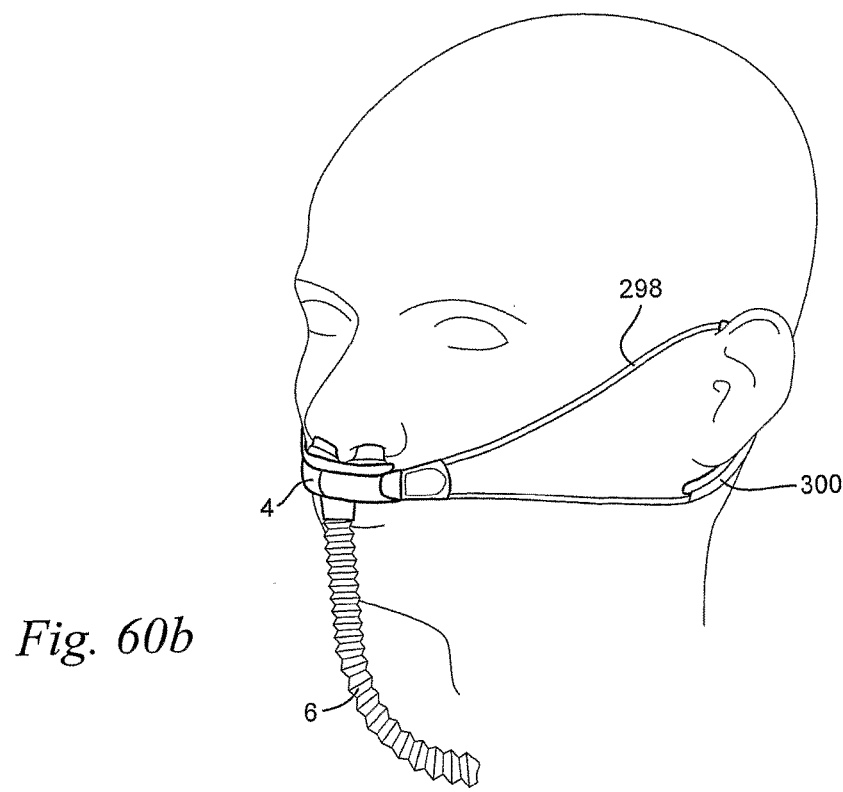
*Fig. 60b*

UNOBTRUSIVE INTERFACE SYSTEMS

CROSS REFERENCE TO RELATED APPLICATIONS

This application is the U.S. national phase of International Application No. PCT/AU2009/000263 filed 4 Mar. 2009 which designated the U.S. and, claims priority to Australian Patent Application 2005901055, filed Mar. 4, 2008, and U.S. Applications 61/058,659, filed Jun. 4, 2008, and 61/080,847 filed Jul. 15, 2008, the entire contents of each being incorporated herein by reference.

FIELD OF THE INVENTION

The sample embodiments relate to interface systems for delivery of a flow of breathable gas to a patient that are less obtrusive than currently available interface systems. The sample embodiments also relate to interface systems for delivery of a flow of breathable gas by a nasal cannula, or cannulae, or similar device, to the patient's nares with the use of an interface that does not form a seal with the patient's airways. The sample embodiments also relate to interface systems for delivery of a flow of breathable gas to a patient's nares with the use of an interface that forms a seal with the patient's airways.

BACKGROUND OF THE INVENTION

The use of positive airway pressure (PAP) for the treatment of sleep disordered breathing (SDB), such as obstructive sleep apnea (OSA), was disclosed in U.S. Pat. No. 4,944,310. Treatment using PAP, which may be continuous PAP, or CPAP, involves the use of a patient interface which is sealingly attached to the patient's face for the provision of the flow of breathable gas. PAP treatment involving the use of a patient interface that is sealingly attached to the wearer's face may be referred to as closed PAP.

Mild or moderate cases of SDB may not be suitable for treatment using closed PAP methods. For example, patients who experience mild sleep apnea, or who may snore, may not gain a significant benefit from the use of closed PAP treatment. In addition, such patients may tend to resist treatment as closed PAP treatment methods generally are obtrusive.

U.S. Pat. No. 7,080,645 discloses an anti-snoring device including a compressor and a nasal air cannula. An air compressor blows air through the nasal cannula into the nose of a sleeping person. The nasal air cannula may, or may not, form a tight seal with the sleeping person's nostrils. If no seal is formed, a throttle valve is provided between the air compressor for flow regulation. If a seal is formed, a bypass valve is provided to allow the sleeping person to exhale.

Because of the small diameter of the nasal cannula, the pressure drop is significant and the compressor must be able to generate excess pressure from 100 to 1,000 mbars relative to ambient. In order to reduce, or prevent, the noise generated by the air compressor from reaching the sleeping person, the air compressor may be fitted with acoustic insulation. A turbine regulator may be provided to the air compressor so that the compressor turbine is able to run at the lowest possible angular speed. The air compressor may also be located in an adjacent room, which may prevent the person from operating the turbine regulator.

The nasal air cannula of U.S. Pat. No. 7,080,645 comprises two tubes running rearward over the ears of the sleeping person. The noise generated by the flow through the cannula may be distracting and disrupt the person's sleep cycle.

For patients that require a higher prescribed pressure for treatment of OSD, a patient interface, e.g. a mask, that forms a seal with the patient's airways may be required. However, the patient may find adapting to current interfaces difficult. For example, the patient may have difficulty sleeping in a familiar, comfortable position once the mask, including the headgear and air delivery hose, are fitted to the patient to provide the required seal. Although the mask is capable of providing a seal and the prescribed pressure, the patient may be reluctant to use the mask due to the problem of sleeping comfortably while wearing the mask. This may result in the patient abandoning the treatment.

SUMMARY OF THE INVENTION

One aspect relates to a patient interface, e.g. a mask or cannula, which delivers a flow of breathable gas to a patient's airways in a less obtrusive manner than current patient interfaces.

Another aspect relates to an apparatus for delivering a flow of breathable gas to a patient's airways without sealing the patient's airways.

A further aspect relates to an apparatus for delivering a flow of breathable gas to a patient while sealing the patient's airways.

A still further aspect relates to treating mild SDB, including mild OSA, or snoring, or asthma, in a less obtrusive manner.

Yet another aspect relates to an unobtrusive interfacing structure that may include septum accommodation.

Another aspect relates to an interfacing structure that may have a foam gasket.

A still further aspect relates to an interfacing structure that may have vented cannula(e).

Another aspect relates to an interfacing structure that may have reduced exhalation noise.

A further aspect relates to an interfacing structure that may have cannula(e) and/or prong(s).

A still further aspect relates to positioning and stabilizing structures for an unobtrusive interfacing structure that may include a clip.

Another aspect relates to positioning and stabilizing structures for an unobtrusive interfacing structure that may include nasal prongs and a barrel connection.

A further aspect relates to positioning and stabilizing structures for an unobtrusive interfacing structure that may include tube rotation.

Yet another aspect relates to positioning and stabilizing structures for an unobtrusive interfacing structure that may include top lip stabilization.

Another aspect relates to positioning and stabilizing structures for an unobtrusive interfacing structure that may include ear attachments.

Another aspect relates to positioning and stabilizing structures for an unobtrusive interfacing structure that may include headgear.

Additional aspects relating to tube connection, pressure port and respiratory therapy are also disclosed.

According to a sample embodiment, an apparatus for delivering a flow of breathable gas to a patient comprises a cannula; first and second cannula branches extending from the cannula, the first and second cannula branches having respective first and second ends configured to engage the nares of the patient in a non-sealing manner; a frame configured to contact the patient's face and support the first and second ends in engagement with the patient's nares; and straps provided at respective ends of the frame, the straps being configured to engage the patient's ears to maintain the frame in contact with the patient's face.

According to a further sample embodiment, an apparatus for delivering a flow of breathable gas to a patient comprises a cannula; and a patient interface connected to the cannula, the patient interface comprising two nasal prongs configured to engage the patient's nares in a non-sealing manner. The patient interface is connected to the cannula so that the position of the nasal prongs is adjustable with respect to the cannula.

According to another sample embodiment, an apparatus for delivering a flow of breathable gas to a patient comprises a cannula; and a patient interface connected to the cannula, the patient interface comprising two nasal prongs configured to engage the patient's nares in a non-sealing manner; and a clip configured to engage the septum of the patient's nose to retain the nasal prongs in engagement with the patient's nares.

According to yet another sample embodiment, an apparatus for delivering a flow of breathable gas to a patient comprises a cannula, the cannula having a first cannula branch and a second cannula branch; and a patient interface connected to the cannula. The patient interface comprises two nasal prongs configured to engage the patient's nares in a non-sealing manner and two opposed leg portions connected to the first and second cannula branches. In a relaxed state of the patient interface, the nasal prongs are spaced apart by a first distance less than the thickness of the septum of the patient's nose. Upon application of opposing forces on the two opposed leg portions, the nasal prongs are spaced apart by a second distance greater than the thickness of the septum of the patient's nose.

According to a further sample embodiment, an apparatus for delivering a flow of breathable gas to a patient comprises a retractable tube; and a clip attached to the tube and configured to engage the patient's nose to hold the retractable tube adjacent to the patient's nares.

According to an even further sample embodiment, an apparatus for delivering a flow of breathable gas to a patient comprises a patient interface configured to sealingly engage the patient's nares; and a headgear configured to maintain the patient interface in sealing engagement with the patient's nares, the headgear comprising first elements configured to extend along the sides of the patient's face, each first element extending to at least a position in contact with the top of the patient's ear, and second elements configured to extend along the sides of the patient's face, each second element extending to at least a position in contact with the bottom of the patient's ear.

According to another sample embodiment, an apparatus for delivering a flow of breathable gas to a patient comprises a patient interface configured to sealingly engage the patient's nares; and headgear configured to maintain the patient interface in sealing engagement with the patient's nares, the headgear comprising a first strap connected to the patient interface, configured to extend around the patient's head below the patient's ears, and a pair of second straps, each second strap connected at a first end to the first strap at a position in front of the patient's ears and connected at a second end to the first strap at a position behind the patient's ears.

According to yet another sample embodiment, an apparatus for delivering a flow of breathable gas to a patient comprises a patient interface configured to sealingly engage the patient's nares; headgear configured to maintain the patient interface in sealing engagement with the patient's nares, the headgear comprising flexible straps extending from opposite sides of the patient interface along opposite sides of the patient's face, a pair of stiffening elements, each stiffening element being connected to an end of a respective flexible strap, and a pair of ear engaging straps, each ear engaging strap being connected to a respective stiffening element and configured to extend around an ear of the patient.

According to still another sample embodiment, an apparatus for delivering a flow of breathable gas to a patient comprises a patient interface configured to sealingly engage the patient's nares; and headgear configured to maintain the patient interface in sealing engagement with the patient's nares, the headgear comprising a pair of first straps, each first strap having a first end connected to the patient interface, each first strap configured to extend from the patient interface along a side of the patient's face and above the patient's ear, and a pair of back straps configured to extend around the back of the patient's head and connect second ends of the first straps, the pair of back straps including an upper back strap and a lower back strap.

According to a further sample embodiment, an apparatus for delivering a flow of breathable gas to a patient comprises a patient interface configured to sealingly engage the patient's nares; and headgear configured to maintain the patient interface in sealing engagement with the patient's nares, the headgear comprising a pair of rigid or semi-rigid frame members, each frame member having a first end connected to the patient interface, and earplugs provided at respective second ends of the frame members, wherein the earplugs are configured to be received in the patient's ears.

According to a still further sample embodiment, an apparatus for delivering a flow of breathable gas to a patient comprises a patient interface configured to sealingly engage the patient's nares; and headgear configured to maintain the patient interface in sealing engagement with the patient's flares, the headgear comprising a strap connected to opposite ends of the patient interface and configured to extend around the patient's head and above the patient's ears.

According to an even further sample embodiment, an apparatus for delivering a flow of breathable gas to a patient comprises a patient interface configured to sealingly engage the patient's nares; and headgear configured to maintain the patient interface in sealing engagement with the patient's nares, the headgear comprising a strap configured to extend around the patients head and below the patient's ears, the strap being configured to maintain the patient interface in sealing engagement with the patient's nares, and a nose bridging strap connected to the strap and configured to extend across the bridge of the patient's nose.

According to yet another sample embodiment, an apparatus for delivering a flow of breathable gas to a patient comprises a patient interface configured to sealingly engage the patient's nares; and headgear configured to maintain the patient interface in sealing engagement with the patient's nares, the headgear comprising a strap configured to extend around the patients head and above the patient's ears, the strap being configured to maintain the patient interface in sealing engagement with the patient's nares, a nose bridging strap connected to the strap and configured to extend across the bridge of the patient's nose, and a forehead strap connected to the strap and configured to extend across the patient's forehead.

According to still another sample embodiment, an apparatus for delivering a flow of breathable gas to a patient comprises a patient interface configured to sealingly engage the patient's nares; and headgear configured to maintain the patient interface in sealing engagement with the patient's flares, the headgear comprising a pair of looped straps extending from opposite sides of the patient interface, wherein each looped strap is configured to loop around a respective ear of the patient.

According to another sample embodiment, a patient interface for delivering a flow of breathable gas to a patient comprises a generally cylindrical portion having a first end and a second end; and a pair of nasal prongs extending from the generally cylindrical portion between the first end and the second end. The pair of nasal prongs are configured to engage the nares of the patient in a non-sealing manner. The generally cylindrical portion and the pair of nasal prongs are integrally formed as a single piece.

According to a still further sample embodiment, a patient interface for delivering a flow of breathable gas to a patient comprises a generally cylindrical portion having a first end and a second end; and a pair of nasal prongs extending from the generally cylindrical portion between the first end and the second end. The pair of nasal prongs are configured to engage the nares of the patient in a non-sealing manner. The pair of nasal prongs are selectively attachable and detachable from the generally cylindrical portion.

According to another sample embodiment, a patient interface for delivering a flow of breathable gas to a patient comprises a generally cylindrical sleeve, the sleeve comprising a first end and a second end, and a pair of nasal prongs extending from the sleeve between the first and second ends; a generally cylindrical barrel configured to be coaxially received in the sleeve so as to be relatively rotatable with respect to the sleeve. The generally cylindrical barrel comprises an aperture configured to align with the nasal prongs of the sleeve to define a flow path for the flow of breathable gas.

According to a further sample embodiment, a patient interface for delivering a flow of breathable gas to a patient comprises a barrel comprising a first end and a second end, a tubular portion extending between the first end and the second end, and a pair of nasal prongs extending from the tubular portion; and a tube connector configured to connect a tube or cannula to the barrel. The tube connector comprises a first end configured to be inserted into the first end or second end of the barrel, and a second end configured to be inserted into the tube or cannula. The barrel is rotatable relative to the tube connector.

According to yet another sample embodiment, a patient interface for delivering a flow of breathable gas to a patient comprises a generally cylindrical barrel having a first end and a second end; a pair of nasal prongs extending from the barrel between the first end and the second end, the nasal prongs being configured to engage the patient's nares in a non-sealing manner to deliver the flow of breathable gas; a tube connector connected to the generally cylindrical barrel and configured to connect the generally cylindrical barrel to a tube or cannula for delivering the flow of breathable gas. The tube connector comprising a first cylindrical portion configured to be connected to the barrel, a second cylindrical portion configured to be connected to the tube or cannula, and a third cylindrical portion connecting the first and second cylindrical portions. The generally cylindrical barrel comprises an intermediate circumferential portion configured to engage and support the first cylindrical portion of the tube connector.

According to still another sample embodiment, a patient interface for delivering a flow of breathable gas to a patient comprises a generally cylindrical barrel comprising a first end and a second end; a pair of nasal prongs extending from the barrel between the first and second ends, the nasal prongs being configured to engage the patient's nares in a non-sealing manner; a frame comprising a generally cylindrical first end and a generally cylindrical second end; a flexible member extending from each of the cylindrical ends of the frame; and a connector provided to each flexible member. The ends of the barrel are received in the respective ends of the frame so that the barrel is rotatable relative to the frame.

According to a further sample embodiment, a patient interface for delivering a flow of breathable gas to a patient comprises a frame comprising a mounting boss; a first barrel portion extending from the mounting boss; a pair of nasal prongs extending from the first barrel portion, the nasal prongs being configured to engage the patient's nares in a non-sealing manner; and a second barrel portion, the second barrel portion being configured to be supported by the mounting boss in engagement with the first barrel portion to define a barrel configured to receive the flow of breathable gas.

According to a still further sample embodiment, a patient interface for delivering a flow of breathable gas to a patient comprises a cushion, the cushion including a base portion defining a breathing cavity configured to receive the flow of breathable gas through an aperture in the cushion, pair of nasal pillows or prongs configured to engage the nares of the patient to deliver the flow of breathable gas from the breathing cavity to the patient; and adhesive on the pair of nasal pillows or prongs configured to secure the cushion to the patient.

According to a further sample embodiment, a patient interface for delivering a flow of breathable gas to a patient comprises a cushion comprising a pair of nasal prongs or pillows configured to sealingly engage the patient's nares; and at least one spring configured to bias the nasal prongs or pillows outwards into engagement with the nares of the patient.

It may be appropriate that some sample embodiments may only operate when sealingly communicating with the nares of the patient. However, it should be appreciated that some sample embodiments of the invention may operate when not sealed with the nares of the patient, or alternatively, may function as intended whether sealed or unsealed with the nares of the patient.

Other aspects, features, and advantages will become apparent from the following detailed description when taken in conjunction with the accompanying drawings, which are a part of this disclosure and which illustrate, by way of example, principles of the inventions.

BRIEF DESCRIPTION OF THE DRAWINGS

The accompanying drawings facilitate an understanding of the various embodiments of this invention. In such drawings:

FIG. 32 schematically illustrates a tube and tube connector according to a sample embodiment;

FIG. 33 schematically illustrate an interface system according to another sample embodiment that includes the tube and tube connector of FIG. 32;

FIG. 34 schematically illustrates an interface system according to another sample embodiment;

FIG. 35 schematically illustrates an interface system according to a sample embodiment;

FIGS. 51*a* and 51*b* schematically illustrate an interface system according to another sample embodiment;

FIG. 52 schematically illustrates an interface system according to another sample embodiment;

FIGS. 60*a*-60*d* schematically illustrate an interface system according to another sample embodiment;

DETAILED DESCRIPTION OF ILLUSTRATED EMBODIMENTS

The following description is provided in relation to several sample embodiments which may share common characteristics and features. It is to be understood that one or more features of any one embodiment may be combinable with one or more features of the other embodiments. In addition, any single feature or combination of features in any of the sample embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

In this application, the terms "mask", "interface", "interface system", and "patient interface" are used interchangeably. However, the terms have the same implied meanings.

1 Interfacing Structure

Figure 1:
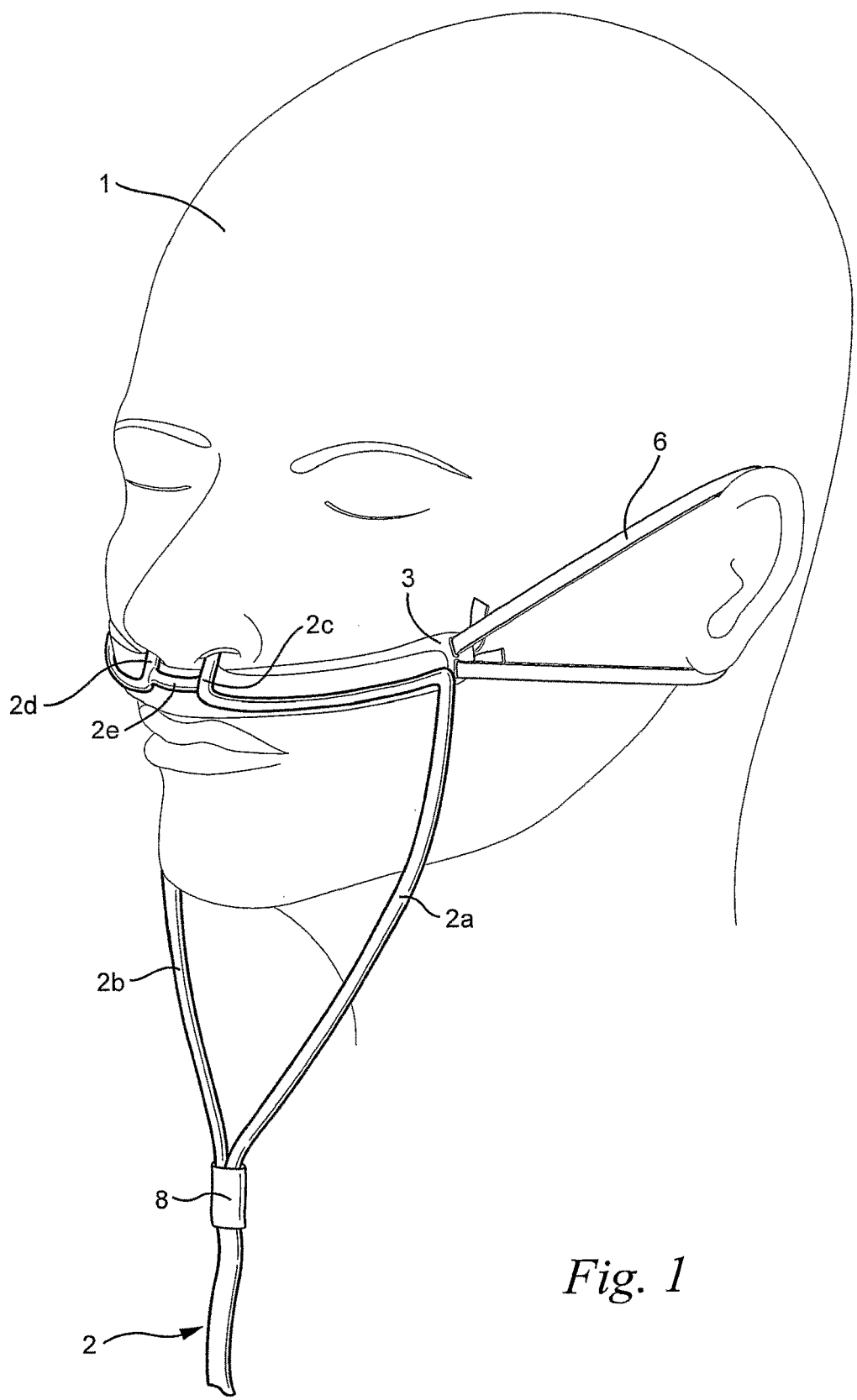
FIG. 1 schematically illustrates a patient interface, or mask, according to a sample embodiment.

Referring to FIG. 1, a flow of breathable gas is delivered to a patient 1 through a cannula 2. The cannula 2 may include a branch connector 8 that connects two cannulae, or branches, 2*a*, 2*b* to the cannula 2. The connector 8 may be provided to connect the cannula 2 and the branch cannulae 2*a*, 2*b* close to one another in the vicinity of the patient 1. Each branch cannulae 2*a*, 2*b* has an end 2*c*, 2*d*, respectively, that is configured for insertion into the nares of the patient 1. The ends 2*c*, 2*d* of the branch cannulae 2*a*, 2*b*, may be connected by a branch 2*e* that allows the flow of breathable gas in the end 2*c* of the cannula 2*a* to communicate with the end 2*d* of the cannula 2*b*. The branch 2*e* may thus tend to equalize the pressure delivered at each end 2*c*, 2*d* of the cannulae 2*a*, 2*b*.

The ends 2*c*, 2*d* of the branch cannulae 2*a*, 2*b* are configured so as not to create a seal with the nares of the patient 1. The flow of breathable gas is delivered by the cannulae 2*a*, 2*b* and vacant spaces created between the ends 2*c*, 2*d* and the nares of the patient 1 allow exhaled air to vent properly.

The ends 2*c*, 2*d* of the branch cannulae 2*a*, 2*b* may be supported by a frame 3. The frame 3 may be configured to extend across the face of the patient 1 in the region between the upper lip of the patient 1 and the nose of the patient 1. The frame 3 may be maintained in contact with the face of the patient 1 by a strap 6 at each end of the frame 3. It should be appreciated that only one strap 6 is visible in FIG. 1. The straps 6 are configured to extend around the ears of the patient. It should be appreciated that the straps 6 may be adjustable in length to accommodate different sized patients, or that the straps may be elastic to stretch from the ends of the frame 3 around the ears of the patient. Also, the straps can extend around the back of the head, either above or below the patient or user's ears. The frame 3 supports the branch cannulae 2*a*, 2*b* and the cannulae ends 2*c*, 2*d* and the branch 2*e* so that the cannulae 2*a*, 2*b* do not extend over the ears of the patient 1 The sound generated by the flow of breathable gas in the cannulae 2*a*, 2*b* is thus distanced from the patient's ears.

Figure 2:
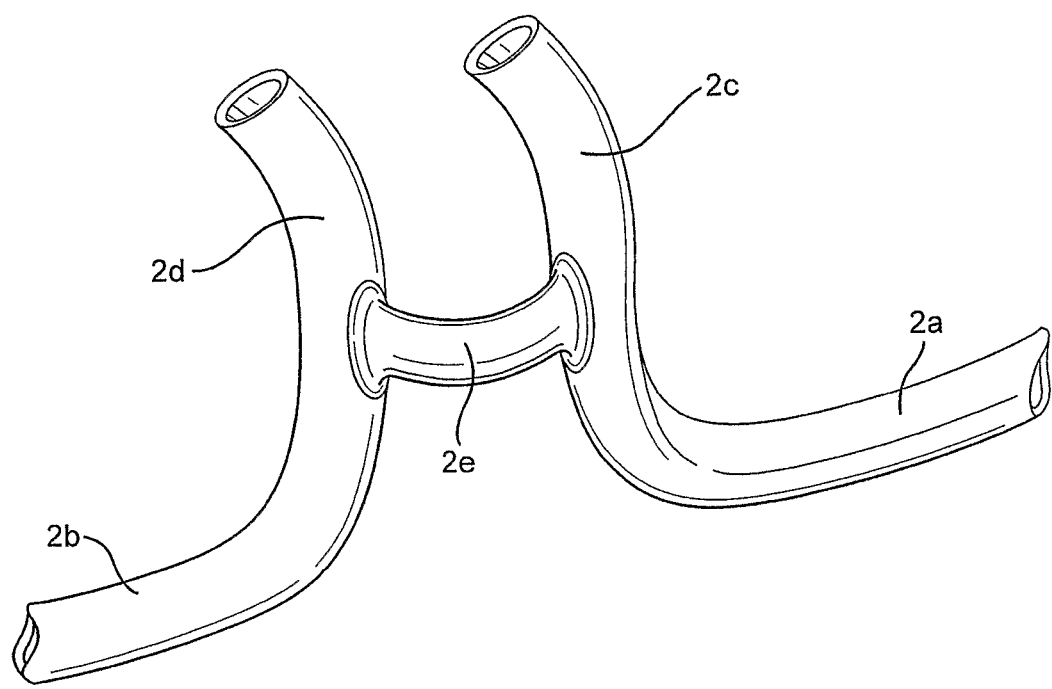
FIG. 2 schematically illustrates nasal cannulae of the interface of FIG. 1.

As shown in FIG. 2, the branch 2*e* connects the ends 2*c*, 2*d* of the cannulae 2*a*, 2*b*. It should be appreciated that the branch 2*e* may be hollow to permit the flow of breathable gas to equalize between the ends 2*c*, 2*d*. The provision of a hollow branch 2*e* also provides for air delivery to the patient 1 even in the event that the patient 1 may tend to sleep on one side and restrict, or cutoff, delivery of the flow of breathable gas through one of the branch cannulae 2*a*, 2*b*. The provision of the hollow branch 2*e* thus assures that the flow of breathable gas is always delivered to both ends 2*c*, 2*d*. It should also be appreciated, however, that the branch 2*e* may be a solid member and serve only to maintain the spacing between the two ends 2*c*, 2*d* and/or provide structural support for the ends 2*c*, 2*d*.

The cannula 2 may have an outer diameter of about, for example, 2 mm-13 mm. The cannula 2 may have an inner diameter of about, for example, 2 mm-8 mm. The thickness of the wall of the cannula 2 may be no more than about, for example, 2 mm, for example no more than about 1 mm.

1.1 Septum Accommodation

Figure 3:
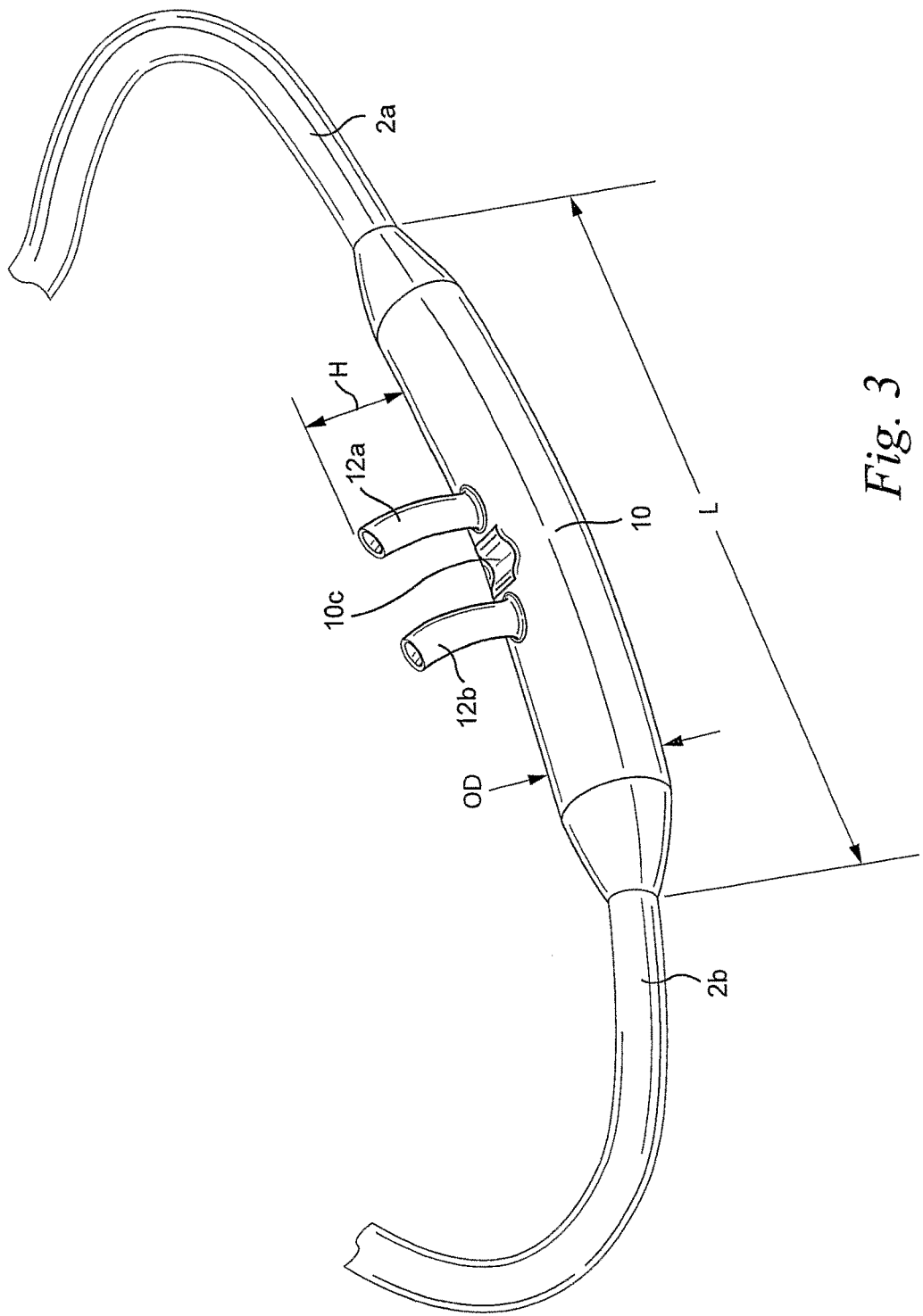
FIG. 3 schematically illustrates a patient interface according to another sample embodiment.

As shown in FIG. 3, the cannulae 2*a*, 2*b*, the patient interface 10, and the nasal prongs 12*a*, 12*b* may be formed as a single piece. For example, the cannulae 2*a*, 2*b*, the patient interface 10 and the nasal prongs may be formed of, for example, silicone. The patient interface may comprise a septum notch 10*c* to accommodate the nasolabial ridges. The septum notch 10*c* may have a depth of about 0-10 mm, for example about 2-7 mm.

The barrel of the patient interface may have a length L that is between about 20 mm-80 mm, for example about 60 mm. The nasal prongs 12*a*, 12*b* may have a height H between about 5 mm-20 mm. The outer diameter OD of the barrel of the patient interface 10 may be between about 5 mm-15 mm, for example about 10 mm.

1.2 Foam Gasket

Figure 4A:
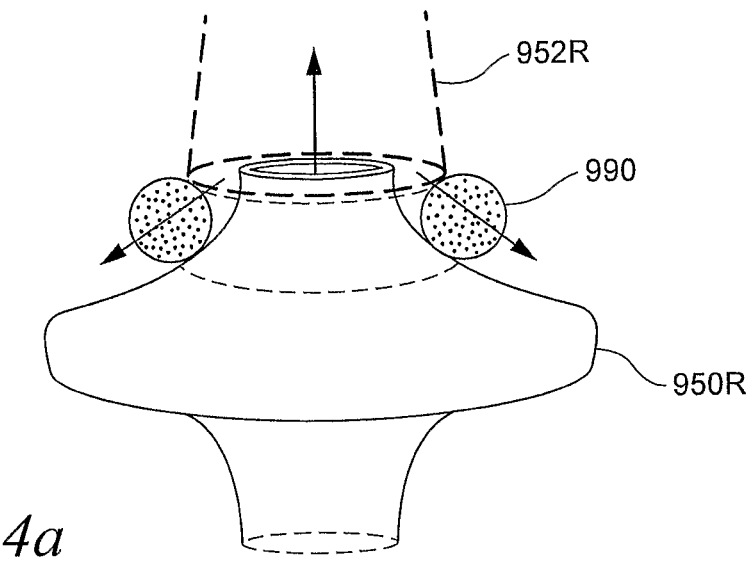
FIGS. 4a-4c schematically illustrate an interface system according to another sample embodiment on of the invention.
Figure 4B:
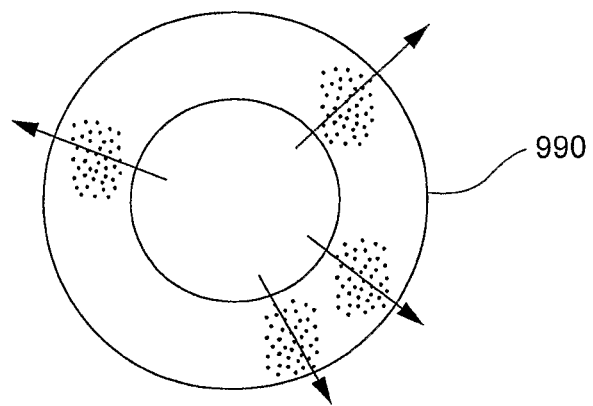
Figure 4C:
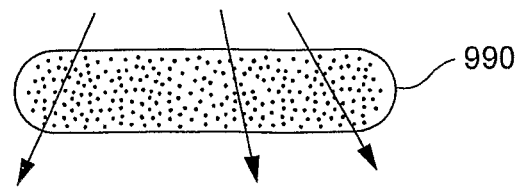

Referring to FIGS. 4*a*-4*c*, the nasal cannula can be utilized with a foam gasket 990 to surround each of the prongs and to contact the nares 952R. The foam gasket 990 may be in the form of a ring and be provided to each prong 950R of the nasal cannula, designed to prevent an outer surface of each prong 950R from sealing against a perimeter surface of each nare 952R (as shown in FIG. 4*a*).

The foam gasket 990 may be circular or oval in shape comparable with an outer edge of the nares 952R and the prongs 950R. While the foam gasket 990 may be formed in the appropriate shape of the nares 952R and the prongs 950R, the soft and flexible nature of the material of the foam gasket will permit it to conform to both the nares 952R and the prongs 950R.

In one form, the size and shape of the foam gasket 990 may affect the size of the gap between the nares 952R and the prongs 952R.

In another form, a separate foam ring or gasket may be provided to each nasal cannula. In an alternative form, two or more foam rings or gaskets may be provided to each nasal prong. In yet another form, a single foam gasket surrounding a perimeter of each prong may also be utilized.

The foam may be permeable. Thus, the foam may be permeable to expiratory air in excess of a certain pressure such as the pressure associated with the combined flow generator flow and expiratory flow of the patient. In this manner, the foam gasket 990 serves as an opening and flow restriction element permitting expiratory air to escape from the nares around the prongs but impeding escape of some of the breathable gas flow of the flow generator particularly during inspiration. In this way, the gasket comfortably permits a lower level of pressurization of the upper airway of the patient.

An example of open celled foam that may be used in this invention is disclosed in U.S. application Ser. Nos. 11/878,932 and 11/878,933, both filed Jul. 27, 2007, the entire contents of each being incorporated herein by reference.

1.3 Vented Cannula

Figure 5A:
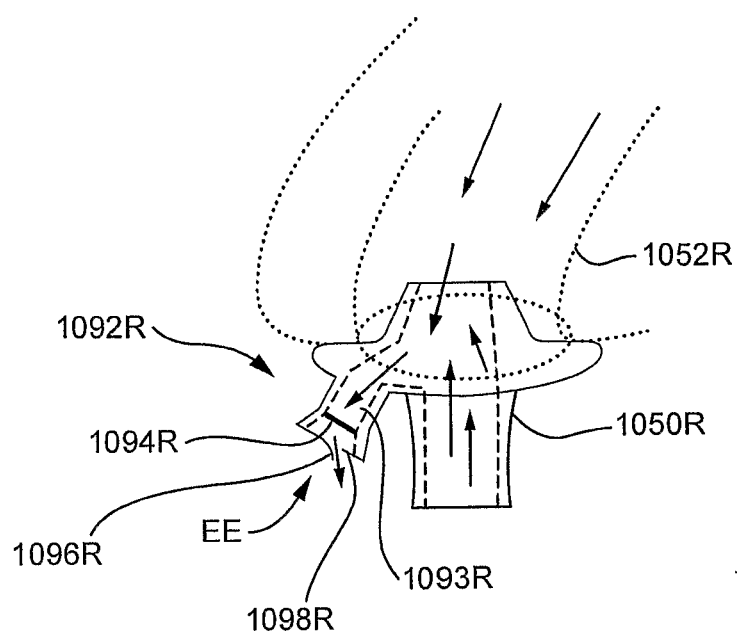
FIGS. 5a-5c schematically illustrate an interface system according to another sample embodiment.
Figure 5B:
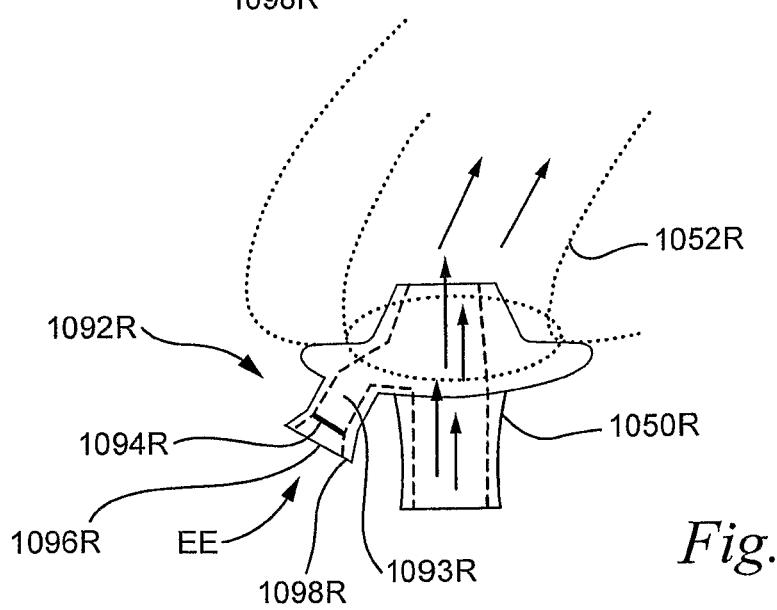
Figure 5C:
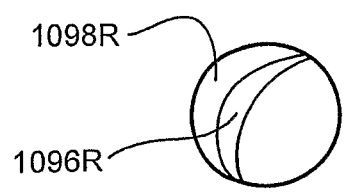

Referring to FIGS. 5a-5c, exhaust gas of the blower and/or expiratory gas from the patient's airway can be vented away from the patient interface from a location proximate to the patient's airway or the nares themselves.

In one form of the embodiment, a nasal cannula is equipped with an exhaust vent as illustrated in FIGS. 5a and 5b. Vents may be implemented on each prong 1050R of the nasal cannula or a common vent may be utilized for both prongs.

As shown in FIG. 5a, the vent 1092R of one prong 1050R is provided at an end of an exhaust canal 1093R such that the vent 1092R may receive a flow of air or gas from a nare 1052R and the flow generator of the open airway treatment device. The vent 1092R may include a flow restriction element 1094R, such as a screen or filter, to restrict flow through the exhaust canal 1093R. The flow restriction element 1094R may also take the form of a mesh material, for example a hydrophobic material. The flow restriction element 1094R may also take the form of a valve, e.g. a passive or active valve. The flow restriction element 1094R may also take the form of a structured membrane, e.g. a slotted or perforated membrane.

The flow restriction element 1094R may be used to control the flow through the vent 1092R and/or to maintain certain pressure levels during inspiration and/or expiration.

The flow restriction element 1094R may be molded together with the cannula and/or nasal prong(s). Alternatively, the flow restriction element 1094R may be provided as in insert to the nasal prong(s). Different sizes of inserts may be used to adjust to different conditions. The inserts may be coded by, for example, color or imprints, to identify the size of each particular insert. The density and/or the dimensions and/or the elasticity of the material may be selected to adjust a certain pressure drop across the flow restriction element 1094R. For example, the density, the dimensions, and/or the elasticity of the flow restriction element may be selected to provide a pressure drop of 1 cm $H_2O$ at a flow of 30 l/min.

The vent 1092R may also include a valve portion including a release flap 1096R and flap contact portion 1098R. The release flap 1096R may be formed from a flexible material, such as silicone. Due to its flexibility, or elasticity, the release flap 1096R may move during use of the nasal cannula as illustrated in FIGS. 5a and 5b. As a result of a higher pressure in the exhaust canal 1093R than ambient pressure outside the vent, such as a pressure increase due to patient expiration and/or flow of the flow generator, the release flap 1096R at the exhaust end EE may distend away from the flap contact portion 1098R as illustrated in FIG. 5a. This permits a flow of air or gas to exit the vent. By choosing a lower elasticity for the material of the flap 1096R, the vent may be designed to permit a pressure difference between the exhaust canal and ambient air (e.g., allowing a higher pressure than ambient pressure in the exhaust canal) without the flap distending. When the exhaust canal pressure does increase beyond such a threshold pressure difference, the flap 1096R may then distend. In the case that the flexibility of the flap 1096R is designed for no such threshold, any above ambient pressure in the exhaust canal 1093R of the prong 1050R will cause the flap 1096R to distend from the flap contact portion 1098R to a position such as that illustrated in the example of FIG. 5a. This will permit an open flow from the exhaust canal 1093R. The elasticity of the flap 1096R and/or a pressure lower than ambient in the exhaust canal 1093R will cause the flap 1096R to return to its position proximate flap contact portion 1098R as shown in FIG. 5b.

In another form of the embodiment, the release flap 1096R may be configured to overlap the flap contact portion as illustrated in FIGS. 5b and 5c. The overlap of the flap 1096R may be designed such that the flap contact portion 1098R resides between the release flap 1096R and the exhaust canal 1093R as illustrated in FIG. 5b. In the event of a lower pressure than ambient in the exhaust canal, such as one created by patient inspiration, the flap may impede significant flow into the exhaust canal from the vent 1092R. In this way, the valve portion may limit a flow through the vent in a single exhaust direction shown by the arrow proximate to the flap in FIG. 5a. Thus, the vent of the prong may be designed to limit the patient's supply of breathable gas or air to the gas supplied from the flow generator rather than ambient air inhaled in through the vent 1092R. Such a feature may help to ensure that the patient is getting the desired filtered, humidified, warmed and/or treatment gas mixture from the airway treatment device rather than any direct ambient air.

In still another form, the flow restriction provided by the vent may be formed by the dimensions of the exhaust canal 1093R and/or the exhaust end EE, i.e. the release flap 1096R and/or the flap contact portion 1098R.

1.4 Reduced Exhalation Noise

Figure 85A:
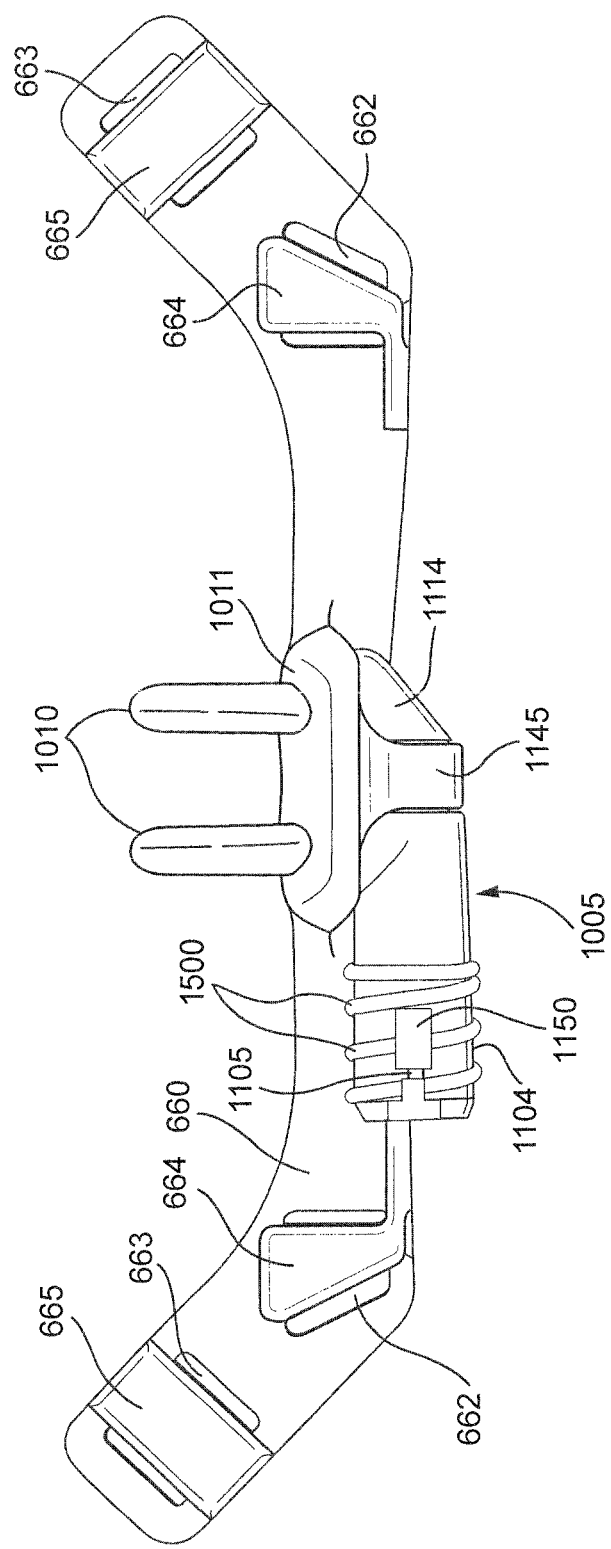
FIGS. 85*a*-85*j* schematically illustrate an interface system according to another sample embodiment.
Figure 85B:
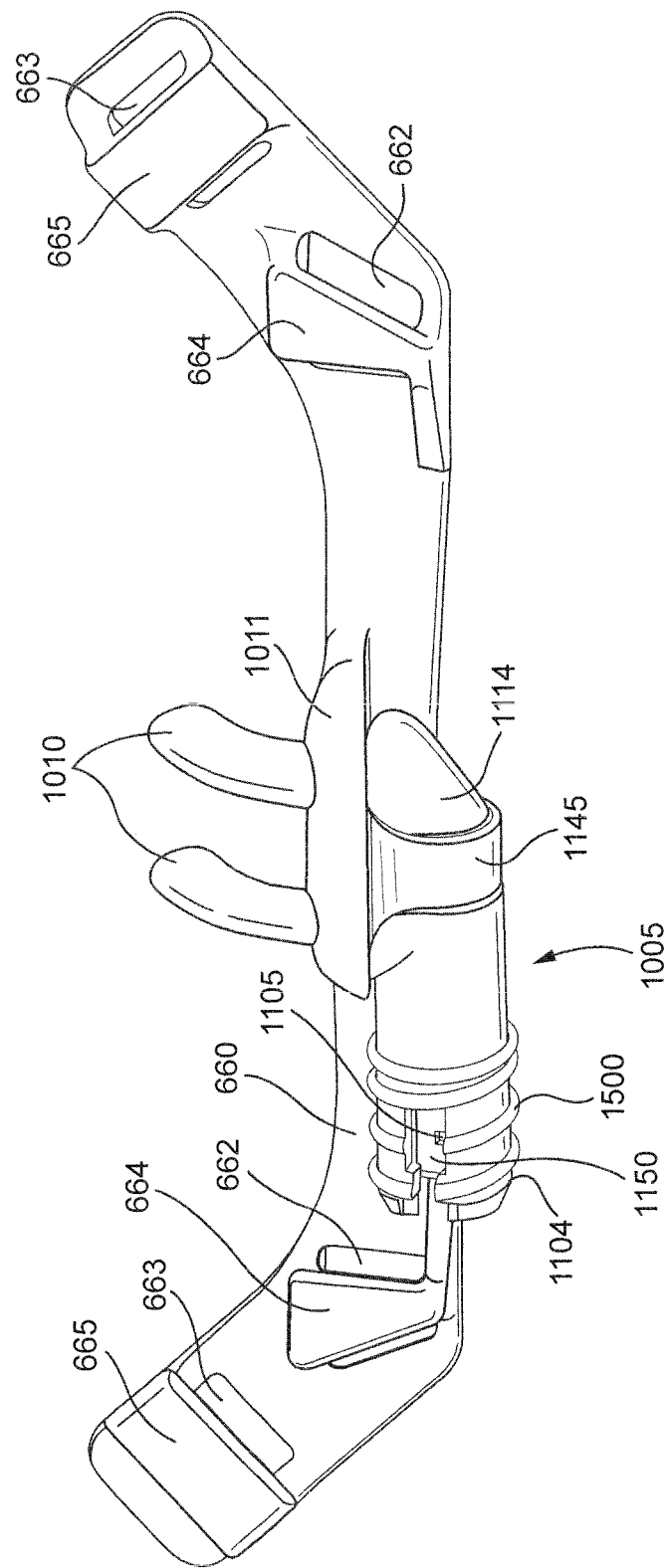
Figure 85C:
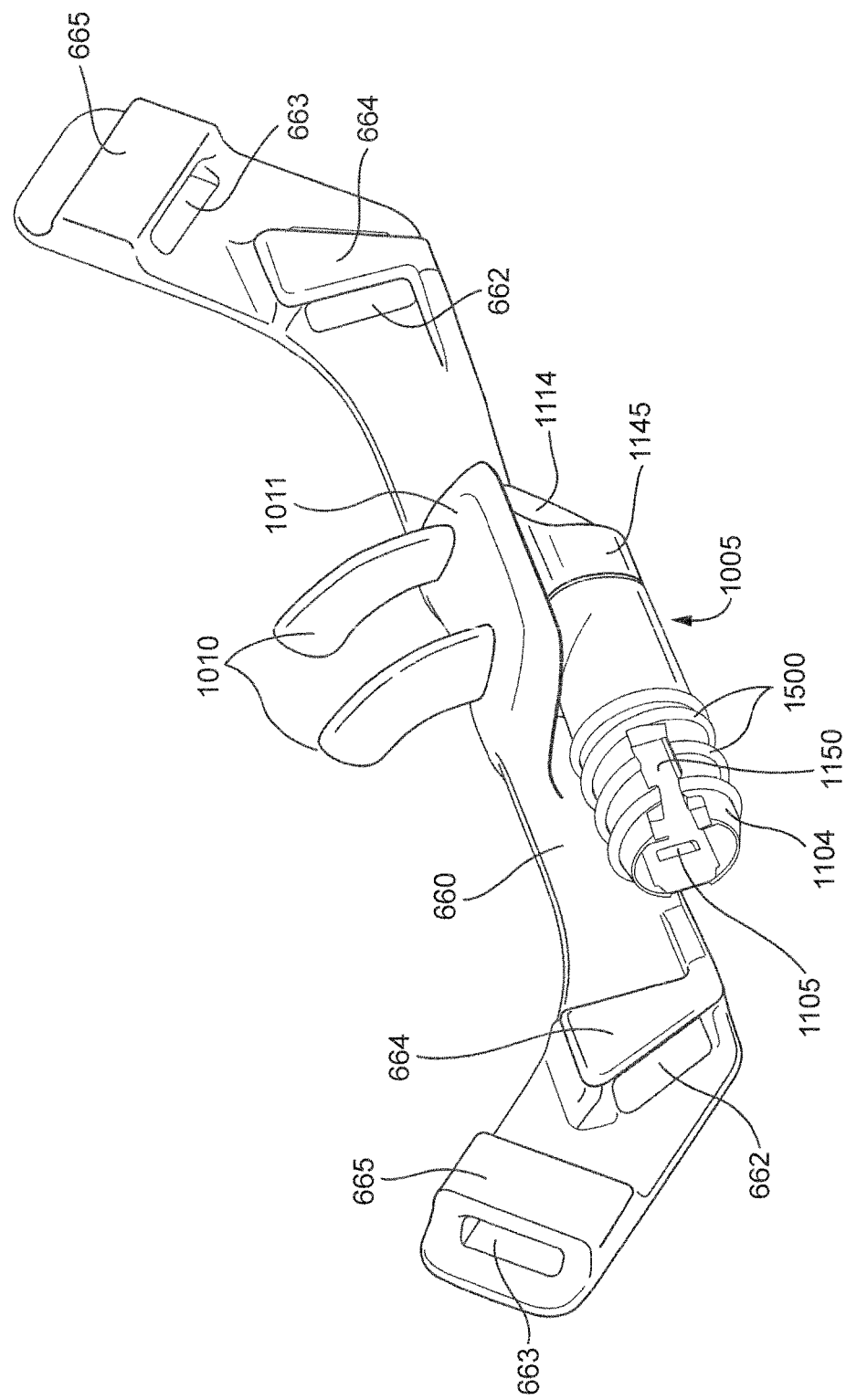
Figure 85D:
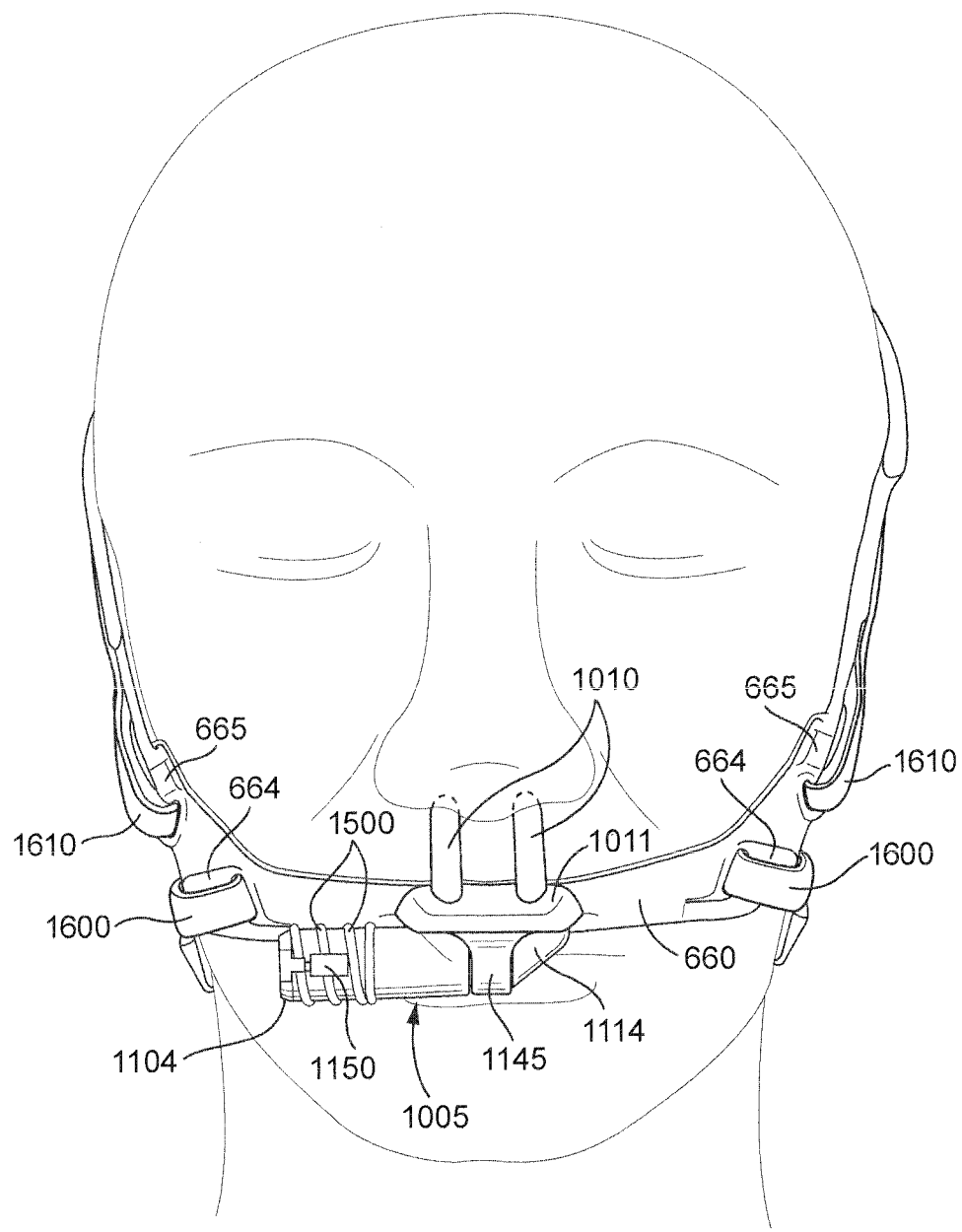
Figure 85E:
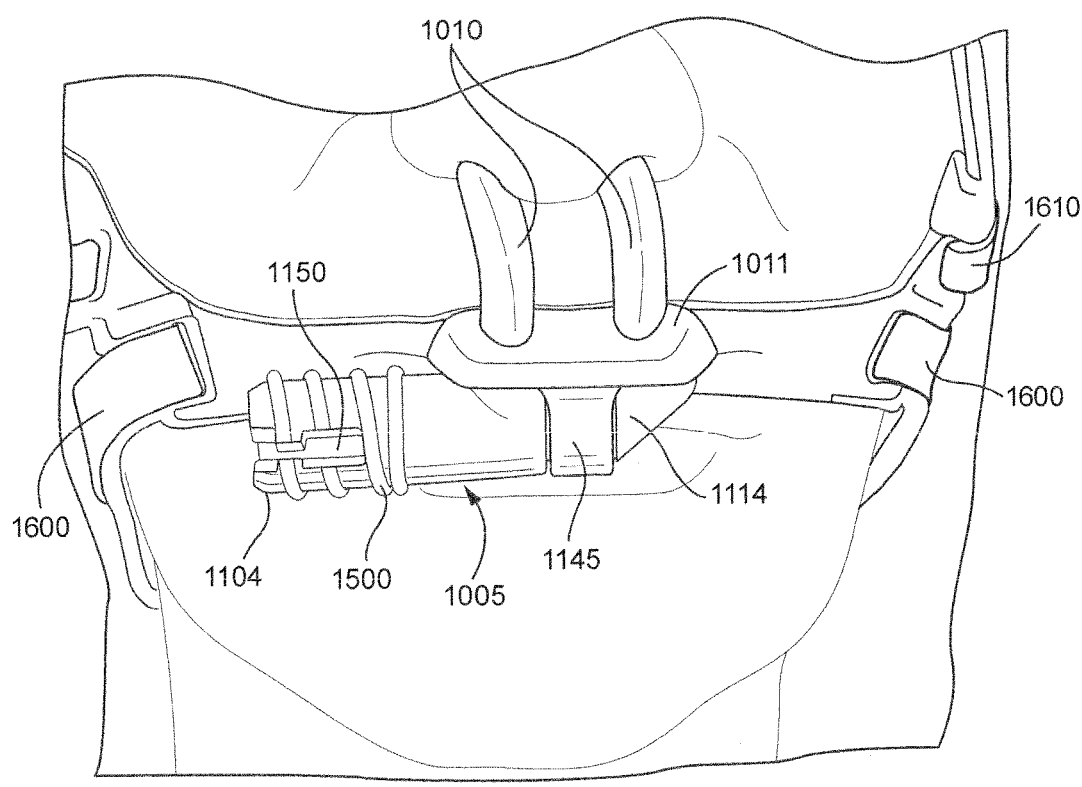
Figure 85F:
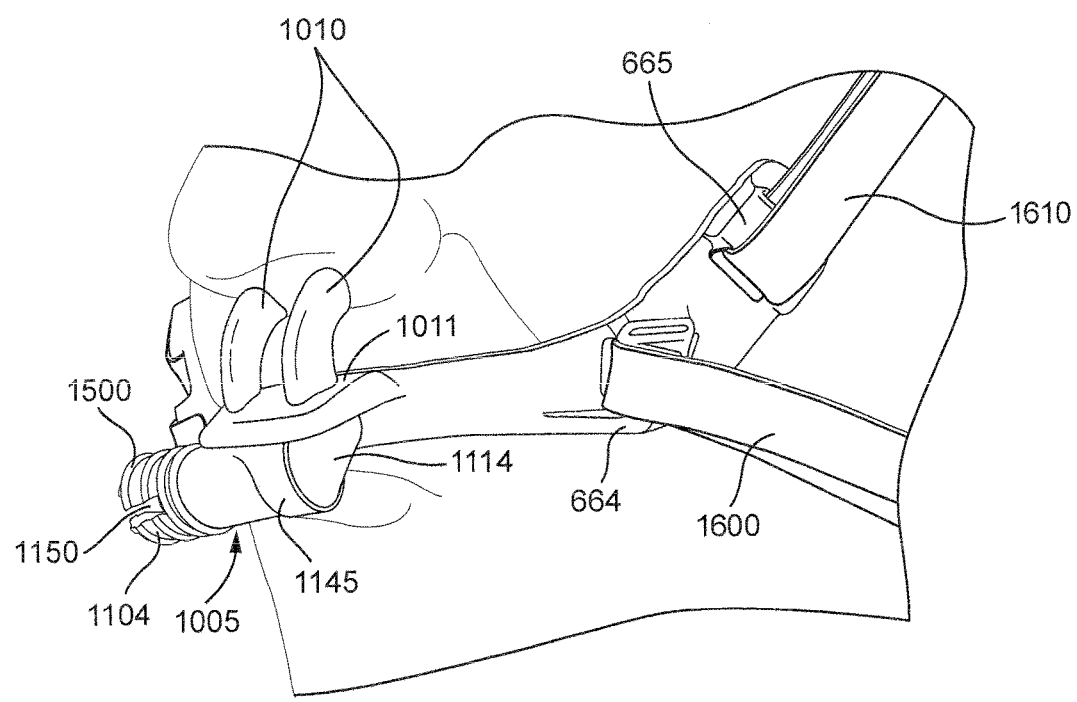

Referring to FIGS. 85a-85c, an interface system according to another sample embodiment comprises a frame 660 comprising slots 662, 663 and strap guides, or connectors, 664, 665, respectively, configured to connect straps to the frame 660. As shown in FIGS. 85a-85c, the frame 660 includes a mounting boss 1145 configured to mount a barrel 1005 of the patient interface. The barrel 1005 comprises a barrel first portion 1011 provided on the frame 660 and a barrel second portion 1114 configured to be sealingly connected to the barrel first portion 1011 when supported by the mounting boss 1145. A pair of nasal prongs 1010 are provided on the barrel first portion 1011 and are configured to engage the nares of the patient, for example as shown in FIGS. 85d-85h. It should be appreciated that the nasal prongs 1010 may be integrally formed with the barrel first portion 1011, or may be separately attachable to the barrel first portion 1011 as a pair or as individual prongs, as described above.

A tube connector 1104 may be provided to the barrel 1005 for connection of a tube or cannula that delivers a flow of breathable gas. The tube connector 1104 may be formed integrally with the barrel second portion 1114 as shown in the drawings, or may be separately formed and connectable to the barrel second portion 1114. The tube connector 1104 may comprise a cutout 1105 for a heating wire and a loom channel 1150 for the loom, i.e. the heating ribbon or wire and the sensor cable(s) bundle. The tube connector 1104 may also comprise circumferential ribs 1500 configured to engage the end of the tube or cannula that delivers the flow of breathable gas. The ribs 1500 are shown in the drawings as helical, but it should be appreciated that they may not be helical. The loom channel allows the tube connector 1104 to be compressed such that its diameter is reduced, for example by squeezing the tube connector 1104 between the fingers of the patient or a clinician, thus allowing the tube or cannula to be more easily inserted over the tube connector. Upon insertion of the tube or cannula over the tube connector, the tube connector may be released and resume its uncompressed diameter. The circumferential ribs 1500 will engage the inner diameter of the tube or cannula and form a friction fit.

1.4.1 Stepped Concentric Air Inlet

Figure 6:
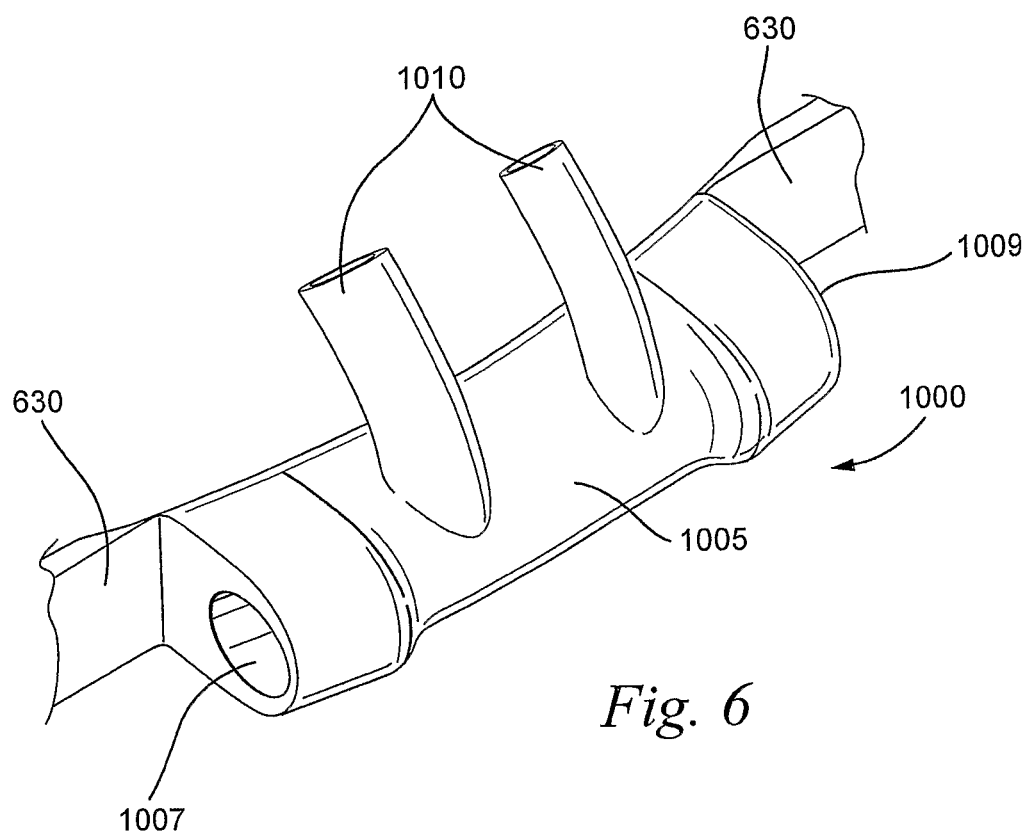
FIGS. 6 and 7 schematically illustrate a patient interface according to another sample embodiment.

Referring to FIG. 6, a patient interface 1000 in accordance with another sample embodiment comprises a barrel 1005 having a first end 1007 and a second end 1009. A pair of nasal prongs 1010 extend from the barrel 1005 for insertion into the nares of the patient. The patient interface 1000 may be connected to a headgear 630, for example the patient interface 1000 may be integrally formed with the headgear 630. Barrel 1005 may be sloped, as shown in FIG. 6, to improve equalized flow to each of the nasal prongs 1010.

Figure 7:
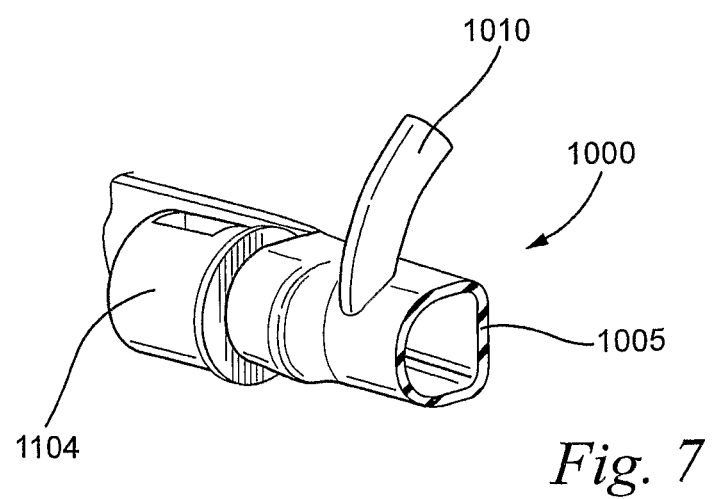

As shown in FIG. 7, a tube connector 1104 may be connected to the first end 1007 of the barrel 1005 of the patient interface such that the longitudinal axis of the tube connector 1104 is collinear with the longitudinal axis of the first end 1007 of the barrel 1005. In other words, the tube connector 1104 and the first end 1007 are concentric. This arrangement presents the lowest impedance to airflow, but increases the size of the patient interface 1000 outward from the patient's face.

The barrel 1005 may have a thickness of about 0.75 mm-2 mm, for example about 1 mm. The barrel 1005 may be thicker at the first and second ends 1007, 1009 where the barrel 1005 is connected to a tube connector or plug.

The barrel 1005 may have a length of about 10 mm-80 mm, for example about 10-40 mm. A barrel length in this range presents a reduced area of interface to exhaled air. The exhaled air may pass down the sides of the barrel 1005 without hitting the portion of the barrel 1005 beneath the patient's nares.

1.4.2. Stepped Offset Air Inlet

Figure 8:
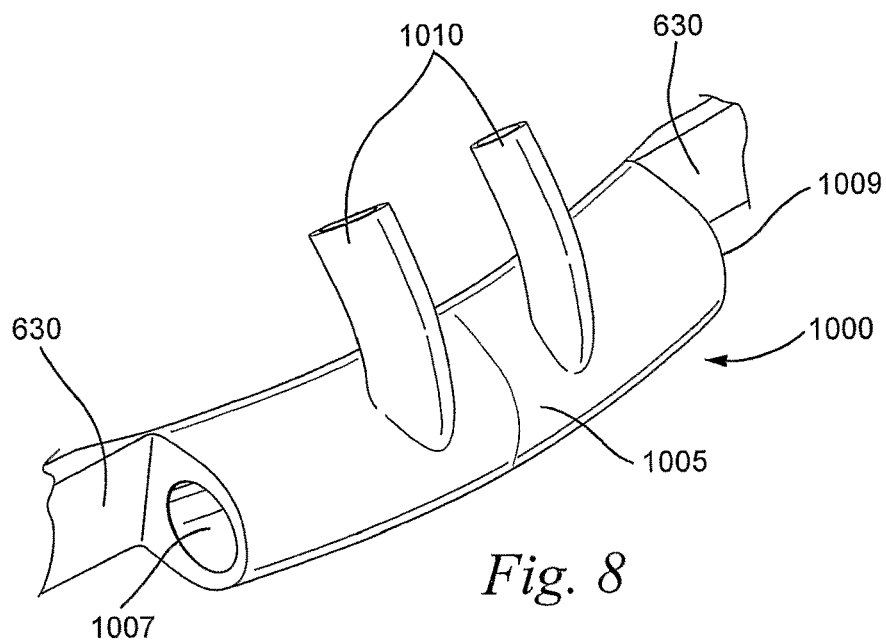
FIGS. 8 and 9 schematically illustrate a patient interface according to another sample embodiment.
Figure 9:
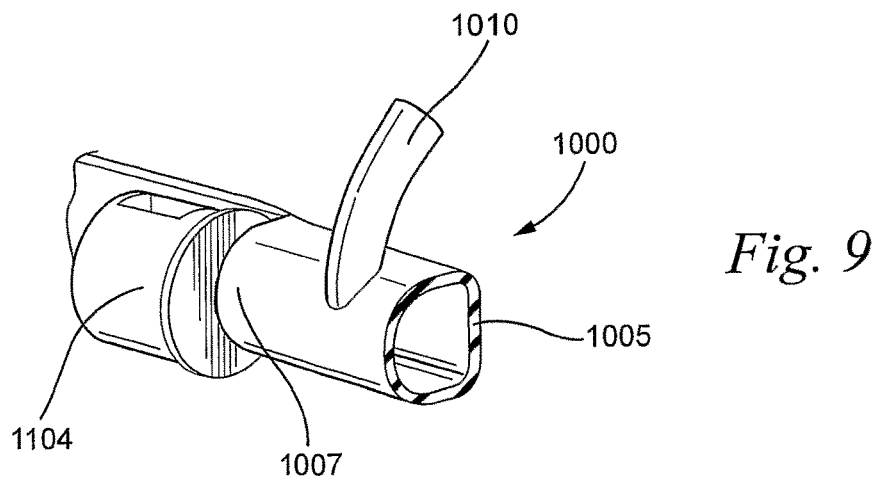

Referring to FIGS. 8 and 9, a patient interface 1000 in accordance with another sample embodiment comprises a barrel 1005 and a pair of nasal prongs 1010. The tube connector 1104 may be connected to the first end 1007 of the barrel 1005 such that the longitudinal axis of the tube connector 1104 is offset from the longitudinal axis of the first end 1007 of the barrel 1005. This arrangement serves to minimize the projection of the patient interface outward from the patient's face and is less intrusive than the concentric arrangement shown in FIGS. 8 and 9. The offset arrangement of FIGS. 8 and 9 also helps to lower the noise as the surface area of the exhaled air path is smaller.

The barrel 1005 may have a thickness of about 0.75-2 mm, for example about 1 mm, and may have a larger thickness at the ends 1007, 1009 where the barrel 1005 is connected to the tube connector and/or a plug. The barrel 1005 may have a length as described above to reduce the area of interface presented to exhaled air.

1.4.3 Oblique Surface

Figure 10:
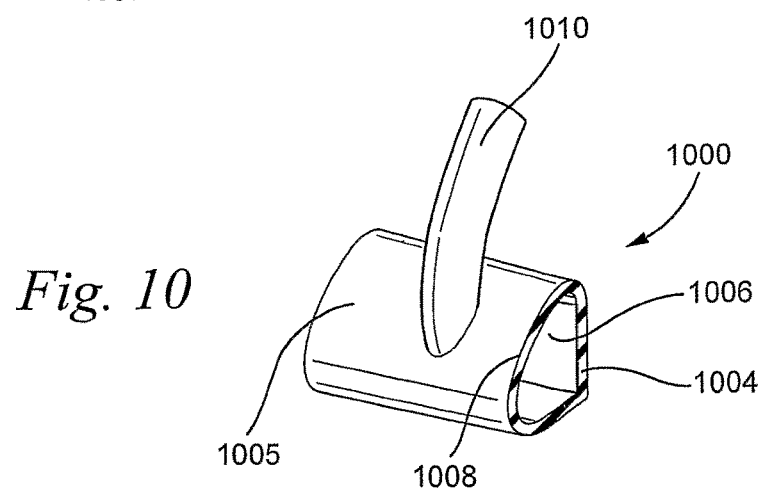
FIG. 10 schematically illustrates a patient interface according to another sample embodiment.

Referring to FIG. 10, a patient interface 1000 according to another sample embodiment includes a cross section 1006 that has an oblique impact angle for the exhaled air from the patient's nares. The oblique surface 1008 of the patient interface 1000 is streamlined to reduce the impact of the patient's exhaled air and thus reduce noise on exhalation. Such an arrangement may increase noise of inhaled air from the air delivery apparatus or flow generator. Therefore, a balance must be struck between minimizing noise of exhaled air and increasing noise of inhaled air. Oblique surface 1008 may form an angle with the rear wall 1004 of about 30°-80°, for example about 45°-75°. This arrangement may also more evenly distribute the flow of air to each of the nasal prongs (only one shown, although it should be appreciated that more than one is typically used for patient treatment).

As shown in FIG. 10, the prongs 1010 are longer than in the previously described embodiments as the prongs 1010 are connected to the barrel 1005 on the oblique surface 1008 at a point that is lower down on the patient interface than in the previously described embodiments.

1.5 Cannula(e) and Prong(s)

The diameter of the nasal cannula or prongs may be designed to have an individual anthropometric fit. For example, the nasal cannula may be made to have an external surface area that conforms to the internal surface area of the nares of the patient. Alternatively, the nasal cannula may be made to have an external surface area that is slightly less than the internal surface area of the nares of the patient.

The diameter of the nasal cannula(e) or prong(s) may be manually or automatically adjustable to have a customizable anthropometric fit. By adjusting the diameter of the prongs, it can vary the resistance to ambient airflow around the prongs (either inspiratory air flow or expiratory air flow) by expanding or reducing a gap between the prongs and the nares. The gap between the prongs and nares will typically be wider when the prong has been contracted to permit more ambient air exchange (i.e., less nasal resistance) and narrower when the prong has been expanded to permit less ambient air exchange (i.e., more nasal resistance). With such adjustable prongs, the flow generator may more easily maintain pressurization of the upper airway of the patient at the desired level.

In another form, such expansion and contraction may be timed to coincide with patient inspiration and expiration as detected from a flow signal determined by the device. For example, the prongs may contract for expiration and expand for inspiration or vice versa. Thus, by adjusting the prongs, a flow generator may implement an end expiratory pressure level that may be appropriate for different patients depending on their condition.

2 Positioning and Stabilizing Structure

2.1 Clip-on

2.1.1 Clip-on First Embodiment

Figure 11A:
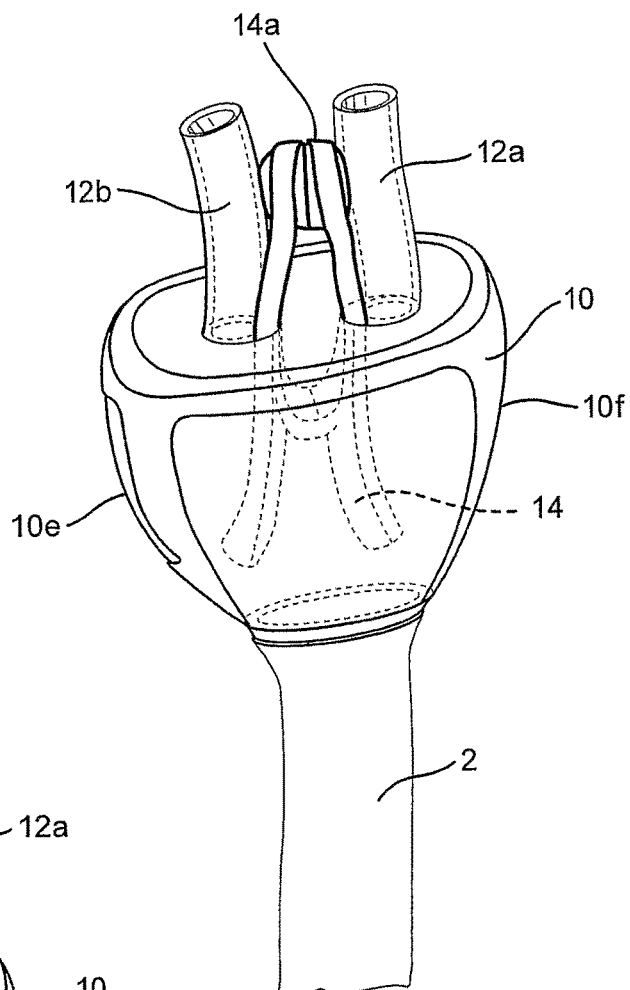
FIGS. 11*a* and 11*b* schematically illustrate a patient interface according to another sample embodiment.
Figure 11B:
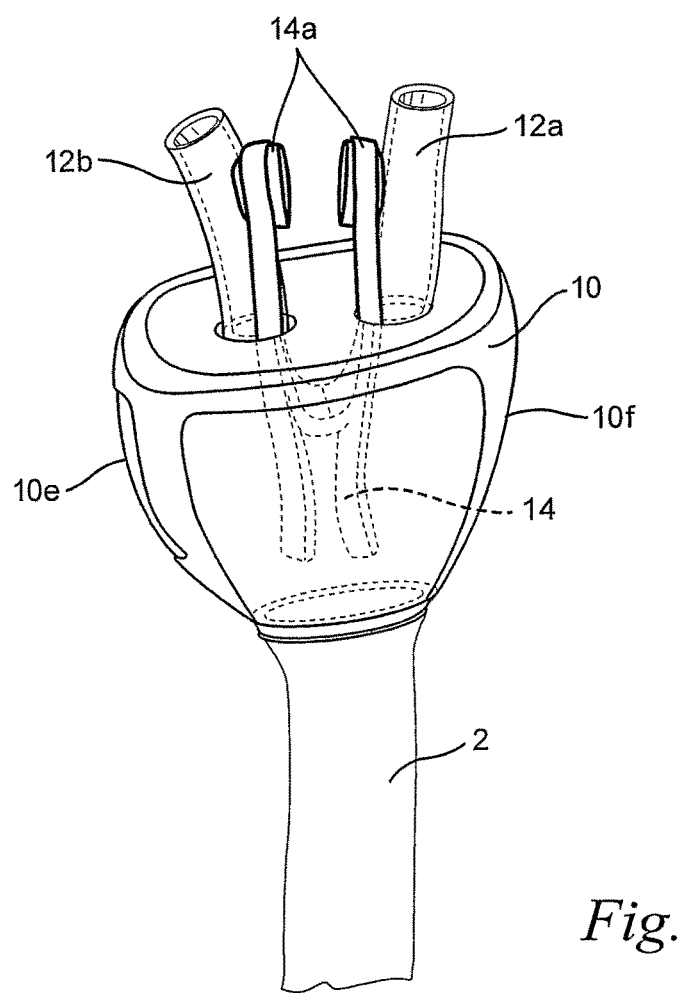

Referring to FIGS. 11*a* and 11*b*, a patient interface 10 is provided at the end of a cannula 2 for delivering a flow of breathable gas. Nasal prongs 12*a*, 12*b* are provided on the patient interface 10 for delivering the flow of breathable gas to the nares of the patient. A clip 14 is provided on the patient interface to attach the patient interface 10 to the septum of the nose of the patient 1.

The patient interface 10 may be formed of a soft material, for example, silicone. In order to open the clip 14, the patient squeezes the sides 10*e*, 10*f* of the patient interface 10 to open the tops 14*a* of the clip 14 (shown in FIG. 11*b*) and allow insertion of the nasal prongs 12*a*, 12*b* into the nares of the patient. By releasing sides 10*e*, 10*f* the tops 14*a* move the nasal prongs 12*a*, 12*b* together, thereby attaching the patient interface 10 to the septum of the nose.

2.1.2 Clip-on Second Embodiment

Figure 12:
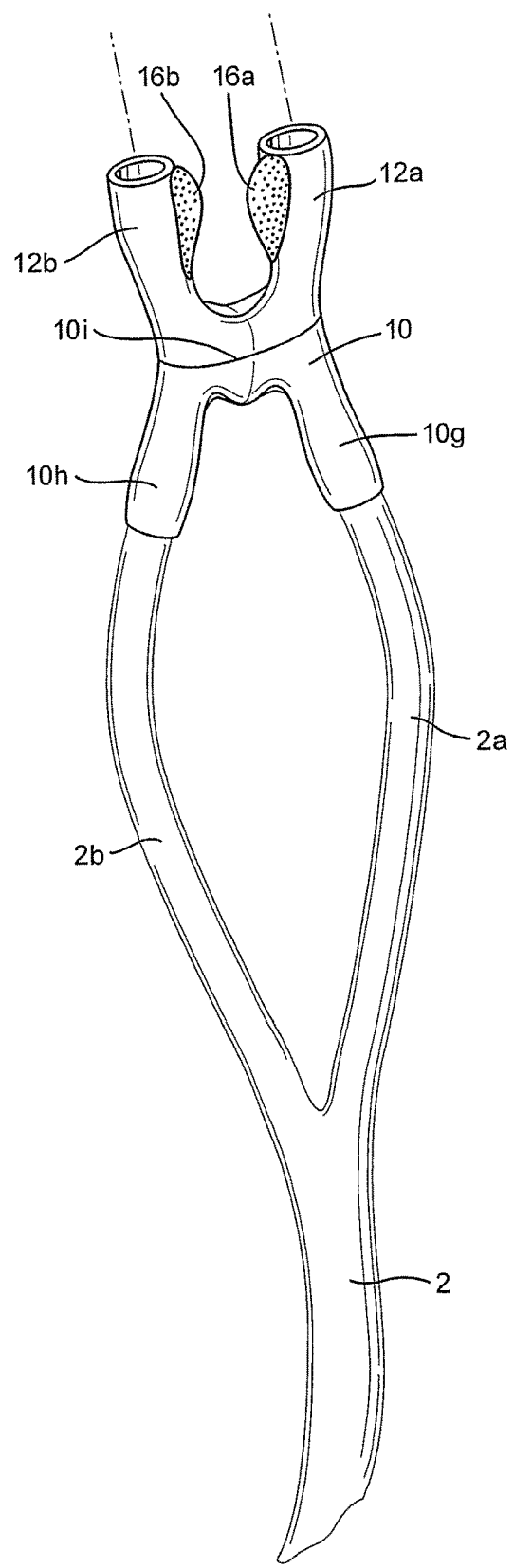
FIG. 12 schematically illustrates a patient interface according to another sample embodiment.

Referring to FIG. 12, a cannula 2 is divided into a first cannula branch 2*a* and a second cannula branch 2*b* to deliver a flow of breathable gas to a patient. A patient interface 10 is provided in fluid communication with the first and second cannula branches 2*a*, 2*b* to deliver the flow of breathable gas to nasal prongs 12*a*, 12*b* provided on the patient interface 10. The nasal prongs 12*a*, 12*b* each include a pad 16*a*, 16*b* and are configured to engage opposite sides of the septum of the nose of the patient. The pad material may comprise a soft and/or low durometer material, such as silicone, with a Shore A hardness of less than about 20, for example silicone with a Shore A hardness of 7. The patient interface 10 may be formed so that in a relaxed state nasal prongs are spaced apart a distance that is less than the thickness of the septum of the patient's nose. In the relaxed state, the pads 16a, 16b may be in contact with one another. In order to separate the nasal prongs 12a, 12b, and the pads 16a, 16b, opposed leg portions 10g, 10h may be squeezed towards one another to separate the pads 16a, 16b and allow insertion of the nasal prongs 12a, 12b into respective nares of the nose of the patient.

As shown in FIG. 12, the patient interface 10 is attached to the ends of the first and second cannula branches 2a, 2b of the cannula 2. It should be appreciated, however, that the cannula 2, the patient interface 10, and the nasal prongs 12a, 12b may all be formed as a single piece. In addition, it should also be appreciated that the pads 16a, 16b may be formed as a single piece with the nasal prongs, the patient interface 10 and the cannula(e).

The middle portion 10i of the interface 10, i.e. the portion between the opposed leg portions 10g, 10h and the nasal prongs 12a, 12b, may be hollow to allow the pressure delivered to each nasal prong 12a, 12b to equalize, for example in the event that flow through one of the cannula branches 2a, 2b is obstructed, or blocked. It should also be appreciated that the middle portion 10i of the patient interface 10 may be solid.

2.1.3 Clip-on Third Embodiment

Figure 13:
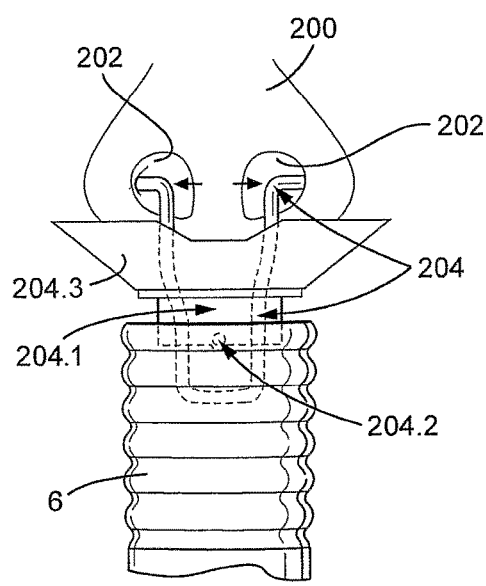
FIG. 13 schematically illustrates a patient interface according to another sample embodiment.

Referring to FIG. 13, a retractable tube 6 provides a flow of breathable gas to the patient's nose 200. The retractable tube may be a retractable tube as disclosed, for example, in U.S. application Ser. No. 12/211,896, filed Sep. 17, 2008, the entire contents of which are incorporated herein by reference. The retractable tube 6 may be secured to the patient's nose 200 by a tube anchor 204 that is configured to be anchored in the nares 202 of the nose 200 of the patient. The retractable tube 6 delivers a flow of breathable gas directly to the nares 202 of the patient. The tube anchor 204 is configured to anchor the patient interface 4 and is configured to open the nares 202 of the nose 200 of the patient.

The tube anchor 204 is secured to the retractable tube 6 via a plug, or connector, 204.1. The plug 204.1 sealingly engages with the retractable tube 6. The plug 204.1 is hollow to allow the flow of breathable gas from the retractable tube 6 to the nares of the patient. The plug 204.1 may comprise a hinge 204.2 that connects to the tube anchor 204. The hinge 204.2 allows the retractable tube 6 to move freely without disrupting the tube anchor 204. The plug 204.1 may comprise a cushion 204.3, for example a foam contacting portion, to sealingly engage with the nares of the patient.

2.1.4 Clip-on Fourth Embodiment

Figure 14:
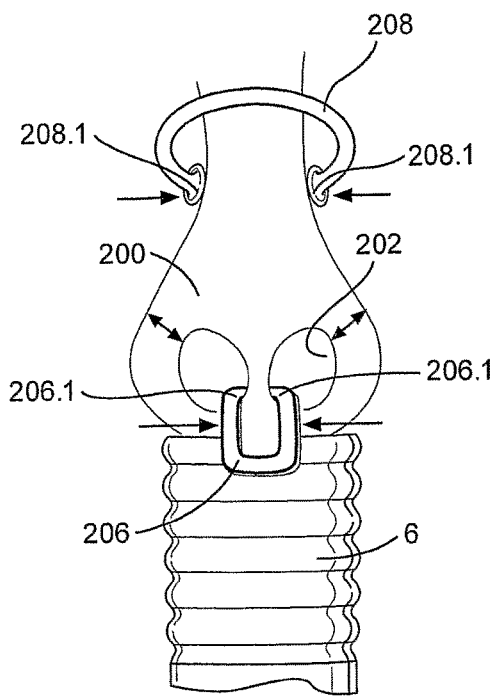
FIG. 14 schematically illustrates a patent interface according to another sample embodiment.

According to another embodiment shown in FIG. 14, a septum clip 206 may be provided for securing the retractable tube 6. A nose bridge clip 208 may be provided in place of, or in addition to, the septum clip 206 for securing the retractable tube 6 and the patient interface 4. The septum clip 206 may have magnets at ends 206.1 and the nose bridge clip 208 may also have magnets at ends 208.1. When in position, as shown in FIG. 14, there is an attraction between the magnets on the septum clip 206 and the nose bridge clip 208 that maintains the interface system in position. The septum clip 206 may be shaped as shown in the FIG. 14. Alternatively, the septum clip 206 may be shaped similarly to tube anchor 204 as shown in FIG. 13. The septum clip 206 may be connected to the retractable tube 6 in a manner similar to that described for the tube anchor 204, i.e. with a plug and hinge as shown in FIG. 13. Similar to the plug 204.1, a cushion may be provided to the septum clip 206, for example a foam contacting portion, to engage with the nares of the patient.

2.1.5 Clip-on Fifth Embodiment

Figure 15:
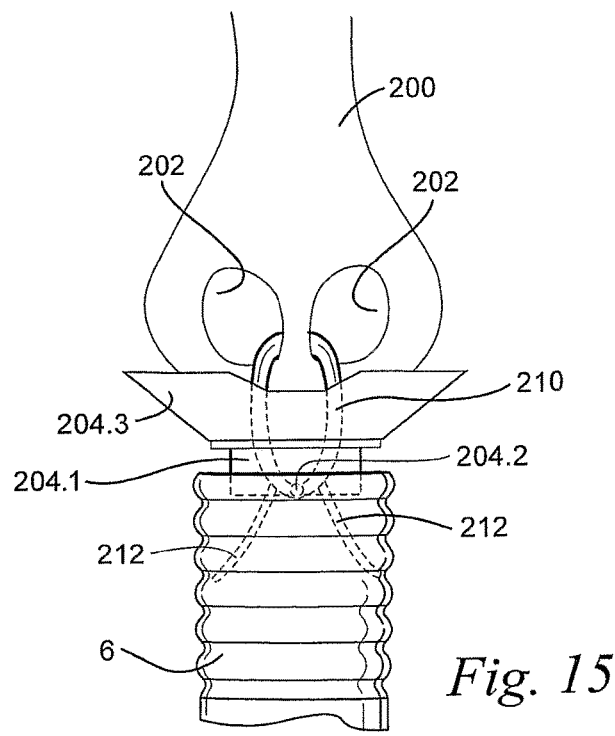
FIG. 15 schematically illustrates a patient interface according to another sample embodiment.

Referring to FIG. 15, the retractable tube 6 may be secured by a septum clip 210 that includes a pair of resilient septum clip legs 212. The septum clip 210 may be opened by squeezing or pressing the septum clip legs 212 towards one another. Upon releasing the septum clip legs 212, the septum clip 210 will close and grab the septum of the patient. As shown in FIG. 15, the septum clip 210 may be connected to the retractable tube 6 in a manner similar to that described with respect to the tube anchor 204, i.e. a plug and hinge, in FIG. 13.

2.2.5.1 Nasal Dilation First Embodiment

Figure 16A:
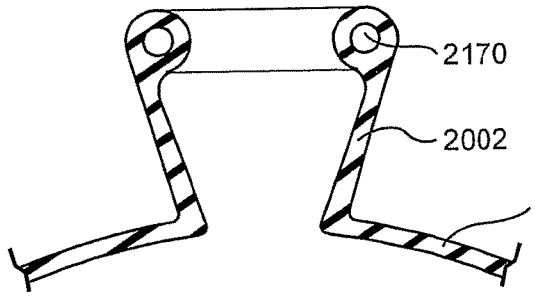
FIGS. 16*a* and 16*b* schematically illustrate an interface system according to another sample embodiment.
Figure 16B:
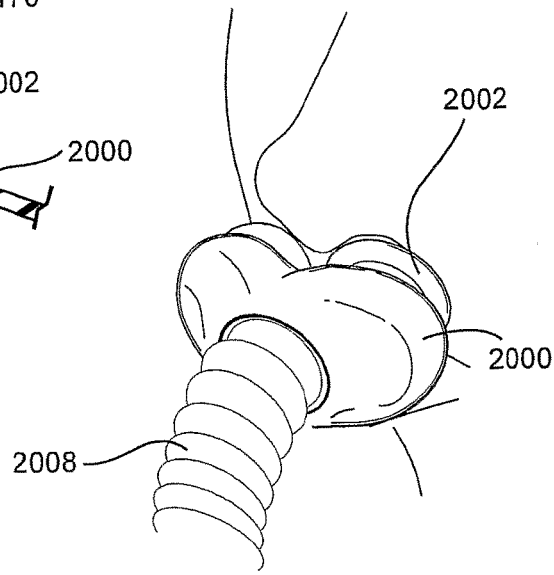

Referring to FIGS. 16a and 16b, the cushion 2000 includes nasal prongs or pillows 2002 that may comprise a ring 2170 that biases the nasal prongs or pillows 2002 to expand. The nasal prongs or pillows 2002 are placed within the patient's nares and during insertion the ring is compressed. Upon full insertion of the nasal prongs or pillows 2002 into the nares, the ring 2170 forces the nares to expand thereby dilating the nasal passageways of the patient's nose. Nasal dilation expands the nares thereby enabling more gas intake and more effective treatment. The cushion 2000 may then be secured to the patient, for example according to any of the methods disclosed herein.

2.2.5.2 Nasal Dilation Second Embodiment

Figure 17A:
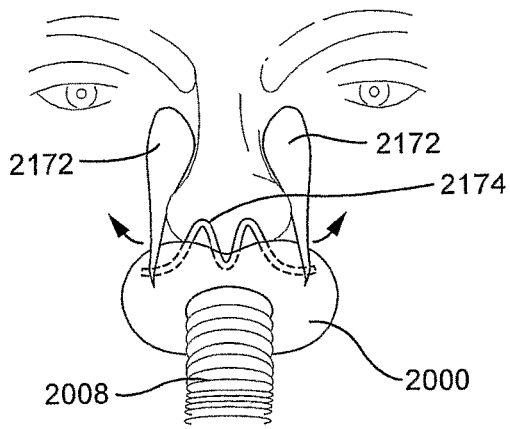
FIGS. 17*a* and 17*b* schematically illustrate an interface system according to another sample embodiment.
Figure 17B:
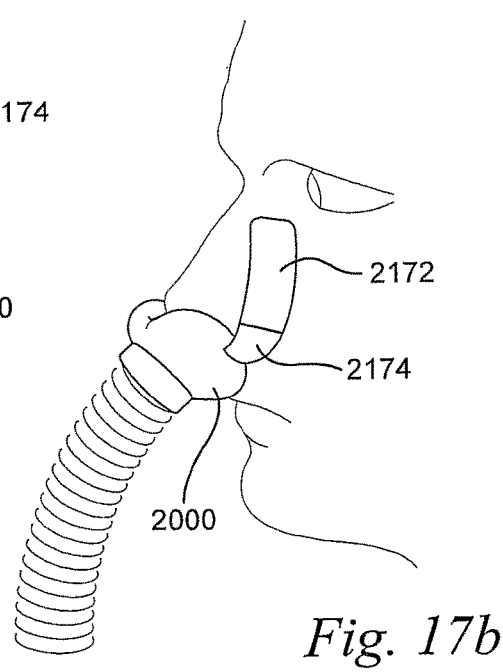

Referring to FIGS. 17a and 17b, the cushion 2000 may comprise a spring 2174 that is configured to engage the nares of the patient's nose. The spring 2174 may be attached at opposite ends to adhesive strips 2172. The spring 2174 is configured to bias the bottom of the nasal prongs or pillows 2002 to a dilated position. The adhesive strips 2174 are configured to be attached to the sides of the patient's nose to secure the cushion 2000 in sealing engagement with the patient's nares.

2.2.5.3 Nasal Dilation Third Embodiment

Figure 18:
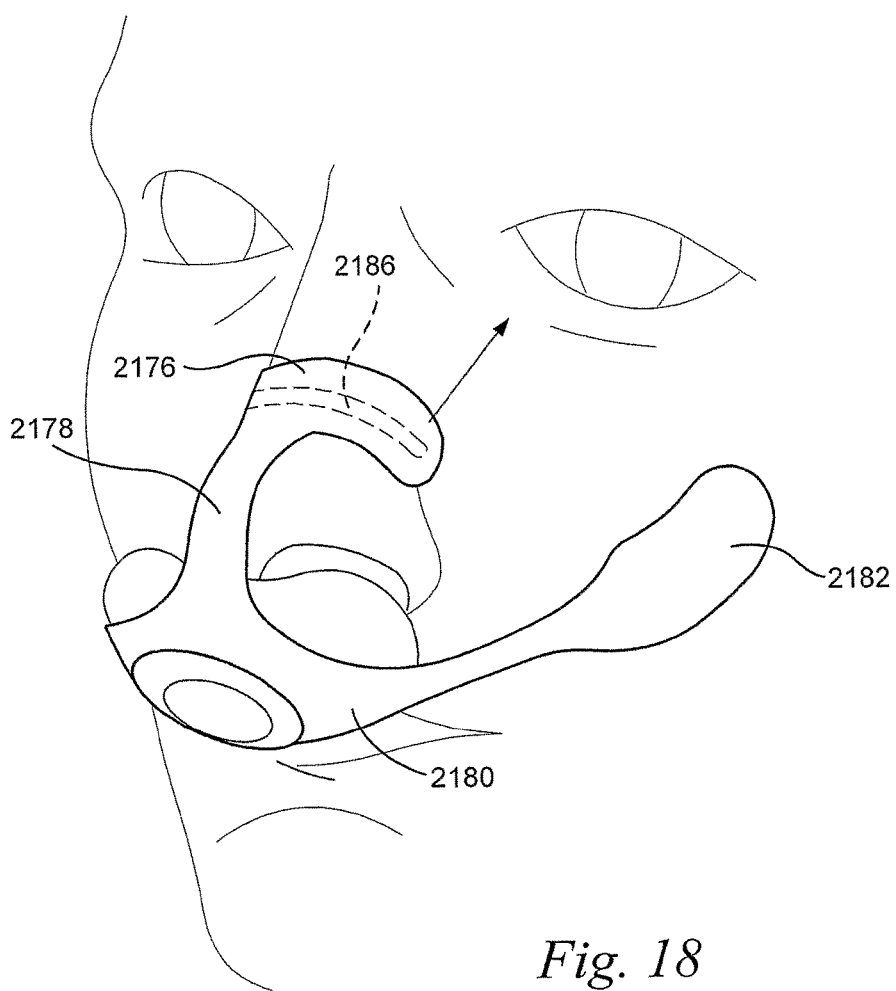
FIGS. 18 and 19 schematically illustrate an interface system according to another sample embodiment.

Referring to FIG. 18, the patient interface system may comprise a lateral nasal bridge adhesive strip 2176 configured to extend across the bridge of the patient's nose. The lateral strip 2176 may also be configured to dilate the nasal passages, e.g., as done by Breathe Right Strips™. The lateral strip 2176 may be integrated with a longitudinal nasal bridge adhesive strip 2178 which is incorporated with a looped adhesive strip 2180 that is configured to adhesively engage the cushion and lateral adhesive strips 2182 that are configured to adhesively engage the sides of the patient's face, e.g. the cheeks.

Figure 19:
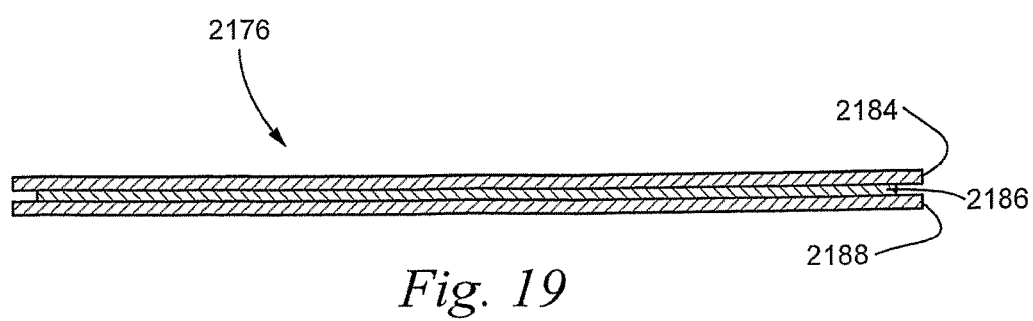

As shown in FIG. 19, the lateral strip 2176 may comprise an outer strip 2184 and an adhesive strip 2188 configured to be adhered to the patient, e.g. across the nasal bridge. A dilation strip 2186 may be provided between the strips 2184, 2188.

Figure 20:
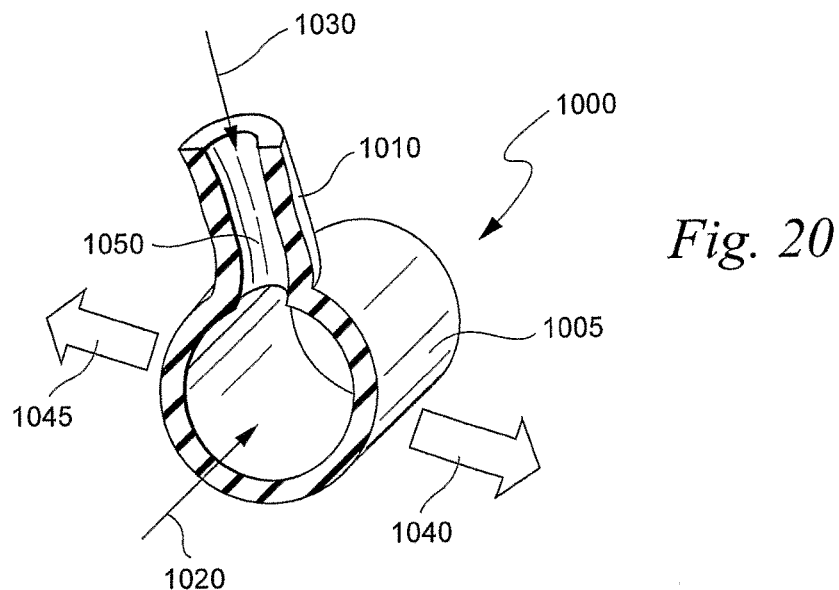
FIG. 20 schematically illustrates an interface system according to another sample embodiment.

2.3 Nasal Prongs and Barrel Connection 2.3.1 Nasal Prongs and Barrel Connection First Embodiment Referring to FIG. 20, a patient interface 1000 comprises a barrel 1005 and a pair of nasal prongs 1010 (only one shown in FIG. 20). The patient interface is formed of a one piece construction to reduce the number of parts necessary for assembly of an interface utilizing the patient interface 1000. The one piece construction also reduces the number of possible leakage sites from the patient interface 1000.

The patient interface 1000 may be formed by molding, for example, silicone, by placing a core 1020 into a mold to form the barrel 1005 of the patient interface 1000. Cores 1030 (only one shown in FIG. 20) may be provided to the mold to form the pair of nasal prongs 1010. The molding tool may be drawn in opposite directions as shown by arrows 1040 and 1045 to form the patient interface 1000. A flash site 1050 may be formed at the junction of the nasal prongs 1010 and the barrel 1005. A flash site at this junction may be the most aesthetically acceptable. In another form, flash at this junction may aid in the diffusion of expired air from the patient thereby reducing the jetting effect on to bed partner, bed clothes, etc.

2.3.2 Nasal Prongs and Barrel Connection Second Embodiment

Figure 21:
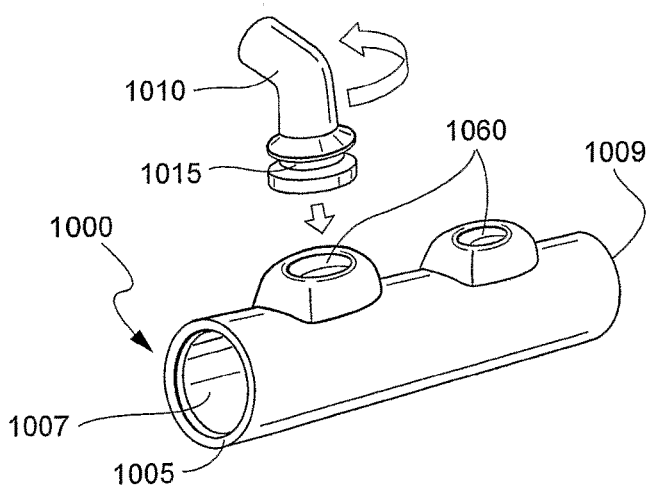
FIGS. 21 and 22 schematically illustrates a patient interface according another sample embodiment.
Figure 22:
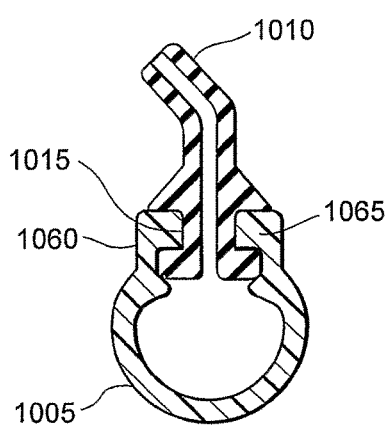

Referring to FIG. 21, the patient interface 1000 may comprise a barrel 1005 and a pair of nasal prongs 1010 (only one shown) that are each selectively attachable and detachable from the barrel 1005. The patient interface 1000 is thus a two piece structure, which may be easier to mold than the one piece construction of the patient interface of the first embodiment shown FIG. 20. As shown in FIG. 21, the barrel 1005 has a pair of nasal prong receptacles 1060 provided between a first end 1007 and a second end 1009 of the barrel 1005. As shown in FIG. 22, the nasal prong receptacles 1060 may have a projecting rim 1065 that is configured to receive a groove, or channel, 1015 formed in the nasal prongs 1010. As also shown in FIG. 21, in the embodiment of the patient interface in which the nasal prongs 1010 are separately formed, each nasal prong 1010 is rotatable with respect to the barrel 1005 of the patient interface to permit further customization of the fit of the patient interface to a particular patient. The selection of particular nasal prongs and/or the rotation of each individual nasal prong may assist in providing greater comfort to the patient.

2.3.3 Nasal Prongs and Barrel Connection Third Embodiment

Figure 23:
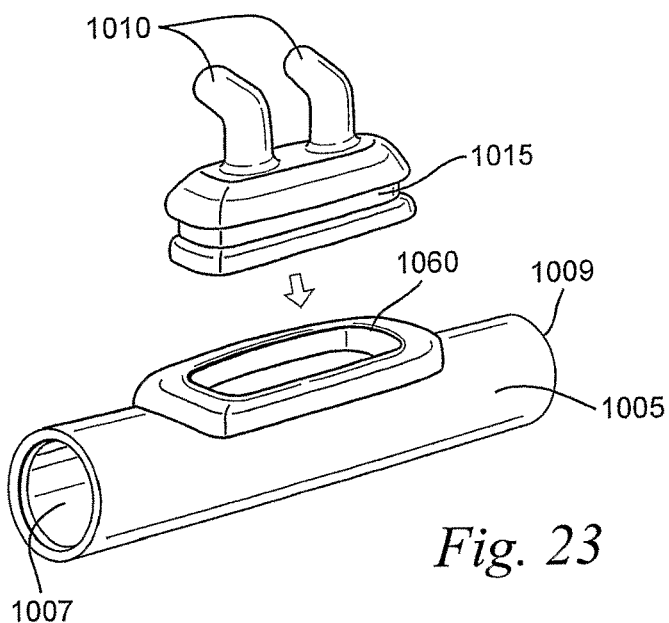
FIG. 23 schematically illustrates a patient interface according to another sample embodiment.

Referring to FIG. 23, the patient interface 1000 may comprise a pair of nasal prongs 1010 that are formed as a one piece construction that is insertable into a single nasal prong receptacle 1060 formed between the first end 1007 and the second end 1009 of the barrel 1005. The nasal prong one piece construction may also comprise a groove, or channel, 1015 that receives a projecting rim 1065 of the barrel 1005 (also shown in FIG. 22).

The provision of separately attachable and detachable nasal prongs, as shown in FIGS. 21-23, permits the customization of the patient interface by selection of nasal prongs 1010 of a height that are particularly suited to an individual patient.

2.3.4 Nasal Prongs and Barrel Connection Fourth Embodiment

Figure 24A:
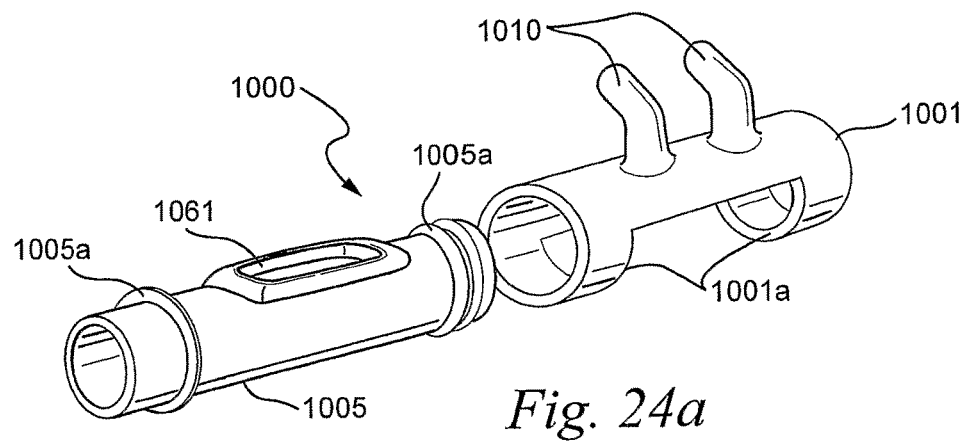
FIGS. 24*a* and 24*b* schematically illustrate a patient interface according to another sample embodiment.
Figure 24B:
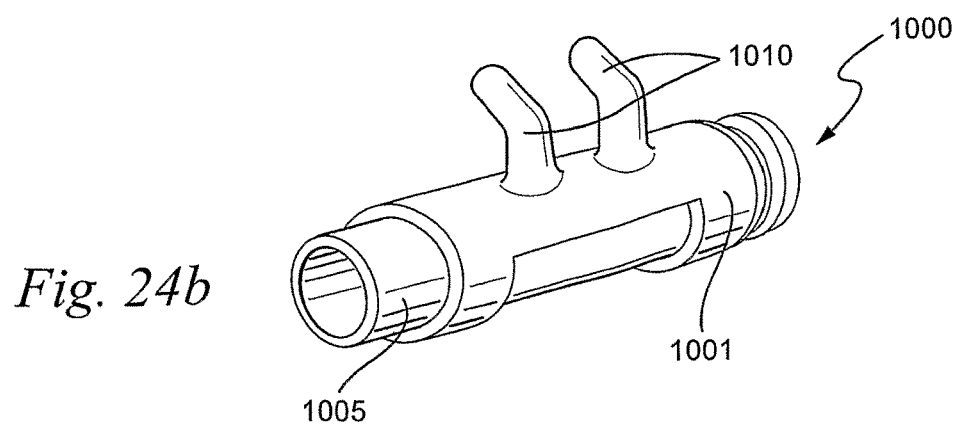

Referring to FIGS. 24a and 24b, a patient interface 1000 may comprise a barrel 1005 that is configured to be inserted into a sleeve 1001. The barrel 1005 may be rotatably supported with respect to the sleeve 1001. The sleeve 1001 comprises a pair of nasal prongs 1010, for example, which may be integrally formed in one piece with the sleeve 1001.

The barrel 1005 comprises an aperture 1061 that is configured to be aligned with the nasal prongs 1010 of the sleeve 1001 when the barrel 1005 is inserted into the sleeve 1001. The sleeve 1001 may comprise edges 1001a that are configured to contact flanges 1005a formed on the barrel 1005 to assist in aligning the aperture 1061 with the nasal prongs 1010.

2.3.5 Nasal Prongs and Barrel Connection Fifth Embodiment

Referring to FIGS. 25-28, a patient interface according to another sample embodiment includes a frame 640 configured for connection to straps of a headgear. The frame 640 comprises slots 642 for receiving the end of a strap of the headgear that is looped through the slots 642.

A mounting boss 645 extends from the frame and includes an aperture 647 that is configured to receive the second portion 1114 of a barrel 1005 that may be integrally formed with a tube connector 1104. It should appreciated, however, that the tube connector may be provided separately.

A first portion 1011 of the barrel 1005 may be connected to the mounting boss 645 and the pair of nasal prongs 1010 may extend from the first portion 1011 of the barrel. The second portion 1114 of the barrel is inserted through the aperture 647 of the mounting boss 645 and a barrel connector portion 1116 of the barrel first portion 1114 is sealingly connected to the barrel first portion 1011.

Figure 25:
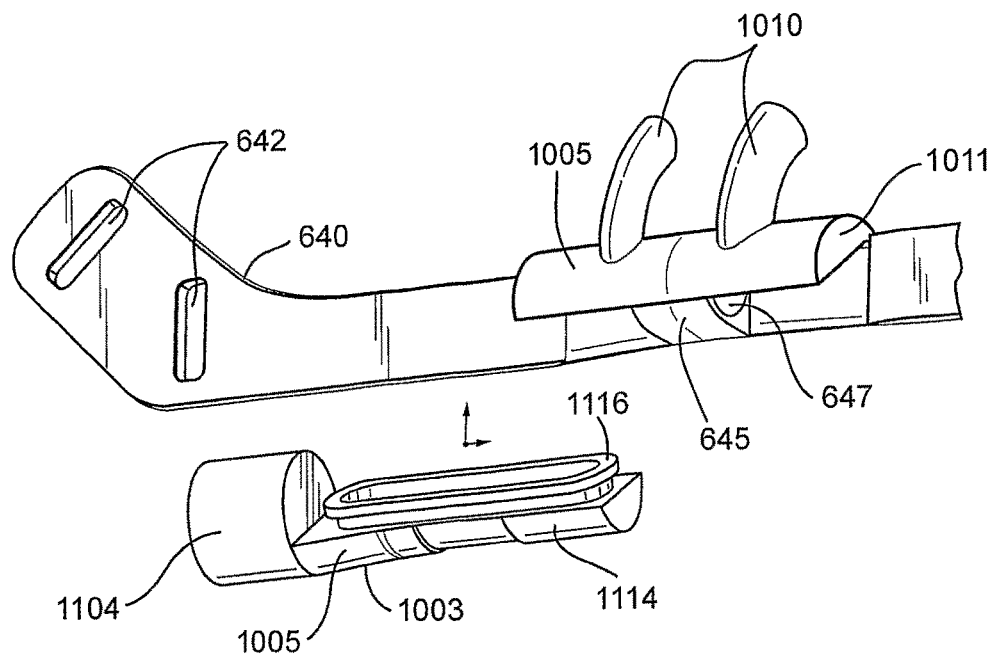
FIGS. 25 and 26 schematically illustrates a patient interface according to another sample embodiment.
Figure 26:
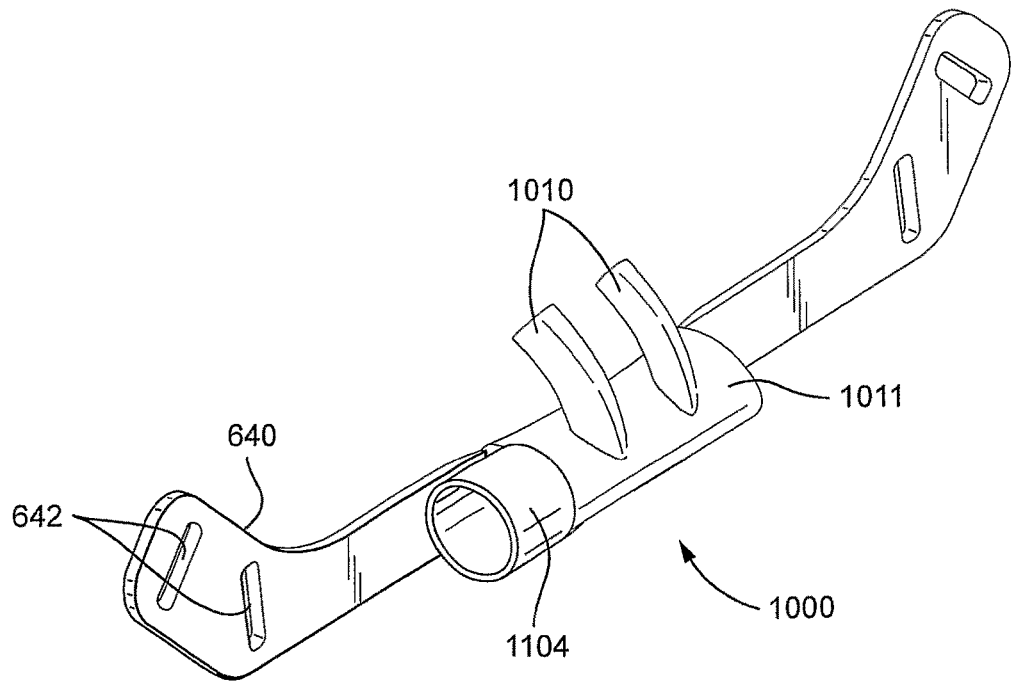
Figure 27:
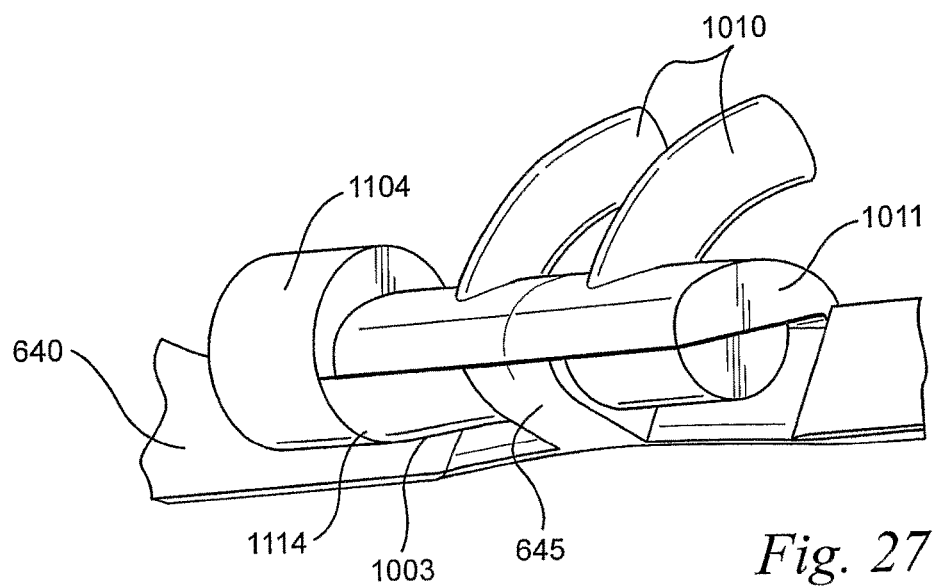
FIGS. 27 and 28 schematically illustrate an interface system according to another sample embodiment.
Figure 28:
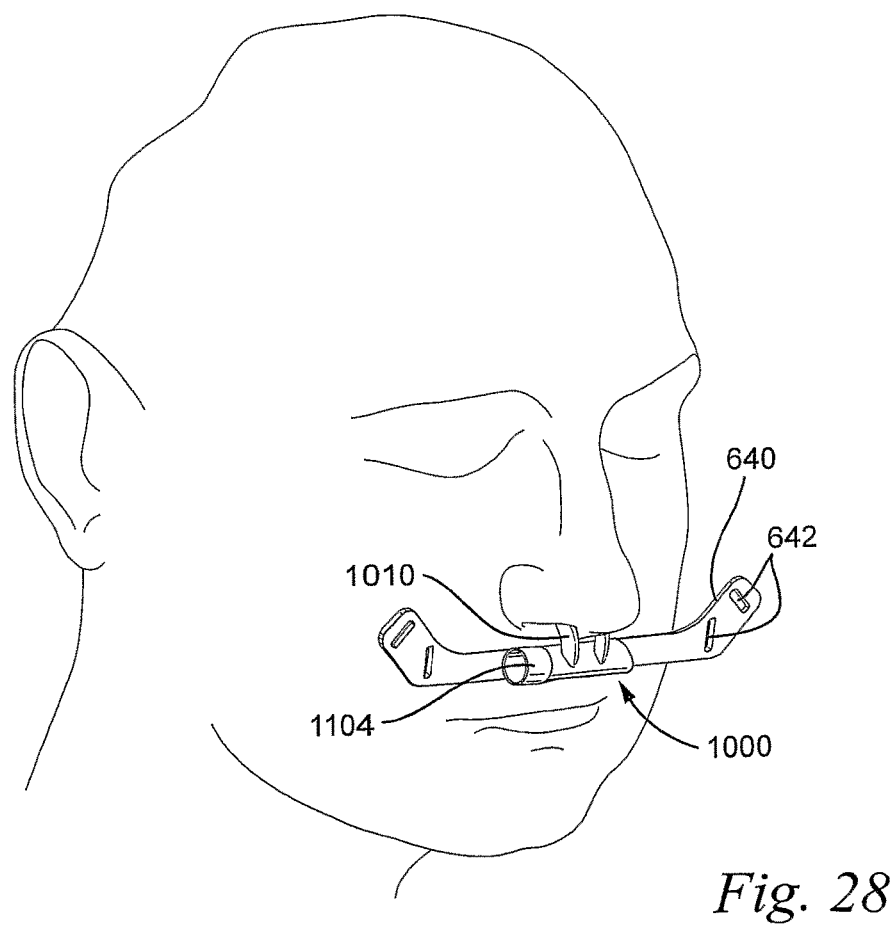

As shown in FIG. 25, the barrel 1005 includes a sloped surface, or ramp, 1003 from a first end of the barrel adjacent the tube connector 1104 to a second end opposite the first end. The ramp 1003 acts to equalize the flow between the nasal prongs 1010.

2.4 Tube Rotation 2.4.1 Tube Rotation First Embodiment

Figure 29:
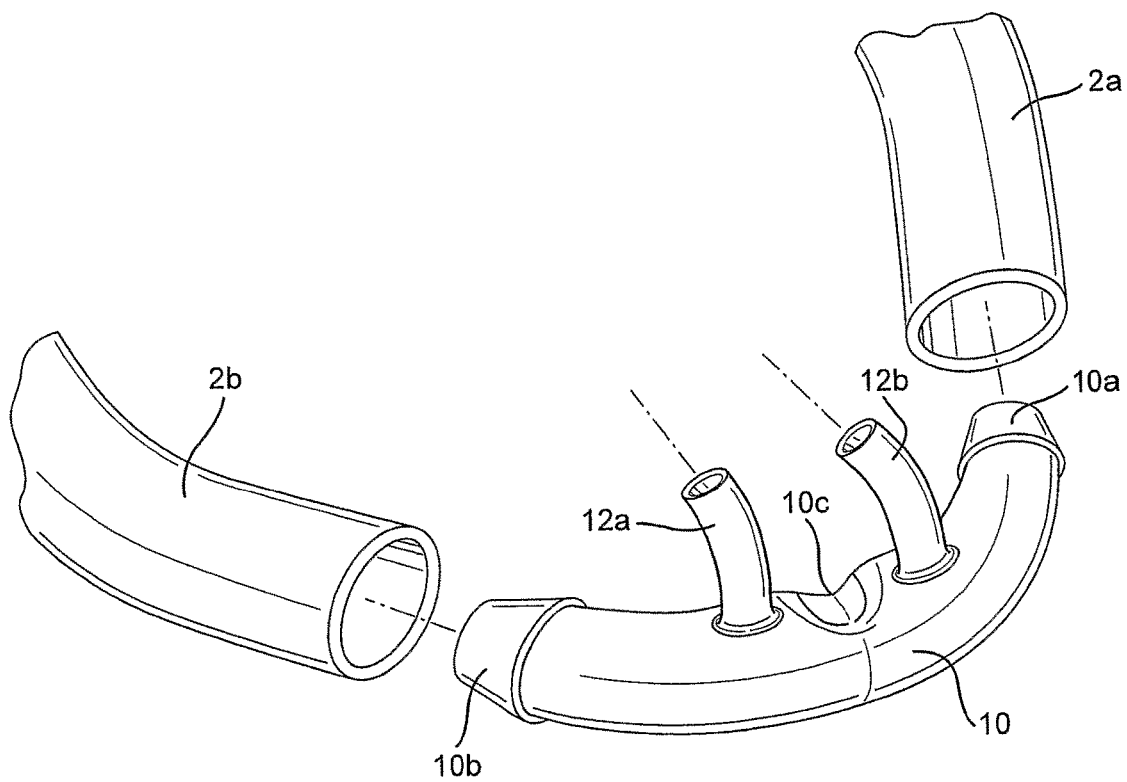
FIG. 29 schematically illustrates an interface system according to another sample embodiment.

Referring to FIG. 29, another sample embodiment comprises a patient interface 10 that is configured to be attached to the cannulae 2a, 2b at ends 10a, 10b of the interface 10. The interface 10 comprises a hollow member, for example in the shape of a barrel, and the flow of breathable gas delivered from the cannulae 2a, 2b is delivered to the patient 1 through nasal prongs 12a, 12b provided on the patient interface 10.

As shown in FIG. 29, the ends 10a, 10b of the patient interface are generally conical. The patient interface may be made of a material, for example, silicone, that allows the interface 10 to be adjustably rotated with respect to the cannulae 2a, 2b when the ends 10a, 10b are inserted into the cannulae 2a, 2b. The adjustable rotation of the patient interface 10 allows the patient 1 to achieve a more comfortable fit and allows the patient interface 10 to be customized to a patient's particular facial contour.

The patient interface 10 may also be configured to have a streamlined aerodynamic low profile to minimize expiration noise caused by the jetting effect of air exiting the nasal prongs 12a, 12b. The patient interface 10 may include a septum dip or notch 10c in an outer surface of the patient interface to accommodate the septum of the upper lip of the patient. As also shown in FIG. 29, the patient interface may have a generally curved contour to follow the curvature of the upper lip of the patient. Each of these features may permit the patient interface 10 to achieve a more comfortable fit, and to make fitting of the patient interface 10 more intuitive.

2.4.2 Tube Rotation Second Embodiment

Figure 30:
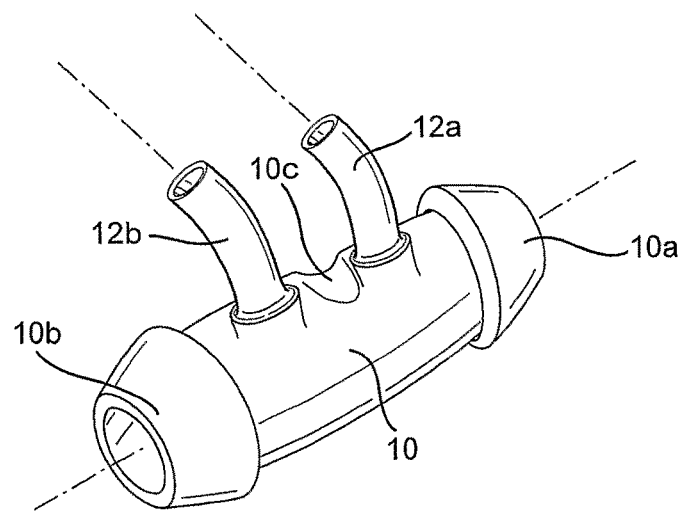
FIG. 30 schematically illustrates an interface system according to another sample embodiment.

Referring to FIG. 30, according to another sample embodiment, the patient interface 10 may be configured as a generally cylindrical member to allow for somewhat easier rotation of the patient interface within the ends of the cannulae 2a, 2b.

2.4.3 Tube Rotation Third Embodiment

Figure 31:
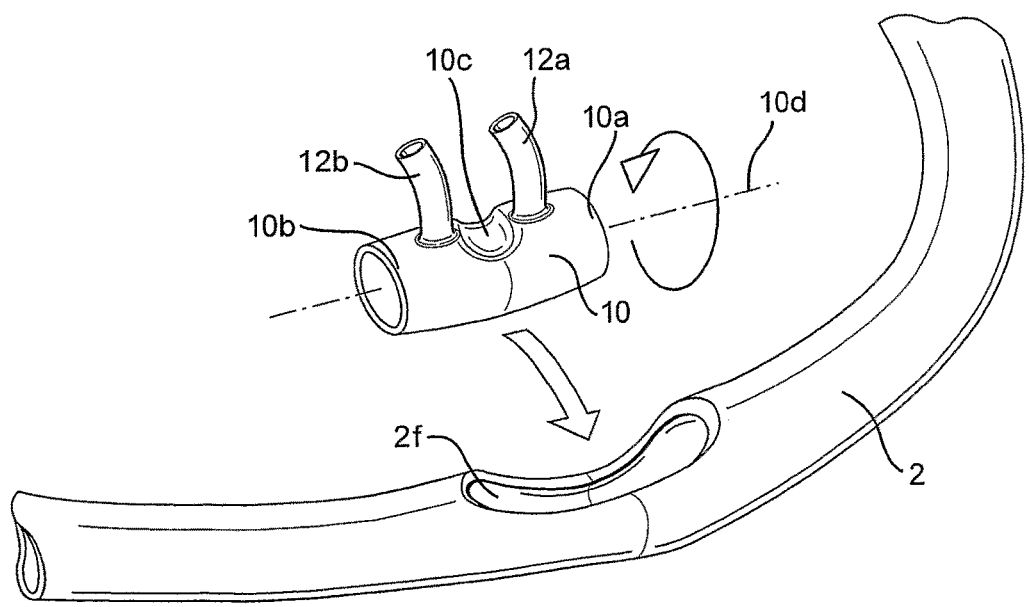
FIG. 31 schematically illustrates an interface system according to another sample embodiment.

According to another sample embodiment shown in FIG. 31, a cannula 2 for delivering a flow of breathable gas may include a recess 2f. A patient interface 10 may be inserted into the recess 2f to deliver the flow of breathable gas to the patient 1 through nasal prongs 12a, 12b extending from an outer surface of the patient interface 10.

The patient interface 10 is inserted into the recess 2f in a substantially leak proof manner. Patient interface 10 can be deformed or squeezed into aperture 2f of cannula 2, and resiliently expand to its original cylindrical shape once adjusted to form a seal with the cannula 2 so that the gas passes through the nasal prongs 12a, 12b. The ends 10a, 10b of the patient interface 10 are inserted into the recess 2f and the cannula 2 is stretched over the patient interface 10 to achieve the substantially leak proof seal. The patient interface 10 is rotatable about its longitudinal axis 10d to permit the patient to adjust the position of the nasal prongs 12a, 12b to achieve the most comfortable fit.

2.4.4 Tube Rotation Fourth Embodiment

Referring to FIG. 32, the tube 1100 may be connected to the patient interface by a tube connector 1104. The tube 1100 may comprise circumferential ribs 1111 at end portion that is configured for connection to the tube connector 1104. The end of the tube 1100 is inserted over the end of the tube connector 1104 and the circumferential ribs 1111 improve the user's grip on the end of the tube 1100. A heating wire 1102 may be provided through the tube 1100 and connected to the tube connector 1104 through a cut out 1105 provided in the tube connector 1104. The end of the heating wire 1102 may be looped through the cut out 1105 to maintain the connection of the tube 1100, the tube connector 1104 and the heating wire 1102. The tube connector 1104 may be formed, for example, of plastic or silicone. The connection of the heating wire 1102 to the tube connector 1104 permits the heating element to run close to the nasal prongs 1010 of the patient interface which reduces the possibility of condensation, or "rain out," in the tube, tube connector, and patient interface.

The tube connector 1104 may also comprise a sensor pocket 1106. A temperature sensor and/or a pressure sensor and/or a humidity sensor may be provided in the sensor pocket 1106. The temperature and/or pressure and/or humidity sensor(s) generates a signal(s) indicative of the measurement(s) of temperature and/or pressure and/or humidity at its particular location. Such a signal(s) can be utilized in settings or calculations of the flow generator. See, for example, U.S. Applications 61/034,318, filed Mar. 6, 2008, 61/042,112, filed Apr. 3, 2008, and 61/084,366, filed Jul. 29, 2008, the entire contents of each being incorporated herein by reference.

It should also be appreciated that other configurations and other components may be implemented to measure the temperature and/or pressure and/or humidity associated with the patient interface.

The tube connector 1104 also comprises a first end 1107 for connection to the tube 1100 and a second end 1108 for connection to the patient interface. A connector flange 1109 may be circumferentially provided around the tube connector 1104 between the first end 1107 and the second end 1108.

Loom channels may be provided in the tube connector 1104 to prevent interference with the tube 1100 and the connection between the tube 1100 and the tube connector 1104 may be sealed with silicone if required. The loom channels are the wiring routing channels for the "loom" which may comprise a heating ribbon, or wire, and a sensor cable bundle passing through the flow generator or humidifier tube connector, or cuff. Such a cuff is disclosed in, for example, U.S. application Ser. No. 11/936,822, filed Nov. 8, 2007, the entire contents of which are incorporated herein by reference.

2.4.5 Tube Rotation Fifth Embodiment

Referring to FIG. 33, rigidizers 614 provide connection points for the patient interface 1000. As shown in FIG. 34, the rigidizers 614 are received in channels at the first end 1007 and the second end 1009 of the barrel 1005 of the patient interface 1000. As also shown in FIG. 34, the second end 1108 of the tube connector 1104 is inserted into an end, for example the first end 1007, of the barrel 1005 and the rigidizers 614 serves to maintain the connection between the tube connector 1104 and the barrel 1005 and to provide a substantially leak proof connection. The other end of the barrel 1005, i.e. second end 1009 as shown in FIG. 34, may be provided with a plug 1115 to seal the patient interface 1000. The use of the plug 1115 allows the patient, or user, to select the entry side of the flow of breathable gas. The rigidizers 614 on the second end 1009 of the barrel 1005 also serve to maintain the connection between the plug 1115 and the second end 1009 of the barrel 1005.

As shown in FIG. 33, the connection of the patient interface 1000 to the rigidizers 614 and the side strap 602 permits the patient interface 1000 to pivot relative to the headgear so that the nasal prongs 1010 may be adjusted to fit the particular patient's facial features.

2.4.6 Tube Rotation Sixth Embodiment

In another embodiment shown in FIG. 35, the second end 1007 of the barrel 1005 of the patient interface 1000 is formed for connection directly to the tube 1100. The second end 1007 of the barrel 1005 may include a sensor pocket 1007a and a cut out 1007b to receive the heating wire 1102. As also shown in FIG. 35, the second end 1009 of the barrel 1005 may be formed as a closed end, thus eliminating the requirement for a plug.

2.4.7 Tube Rotation Seventh Embodiment

Figure 36:
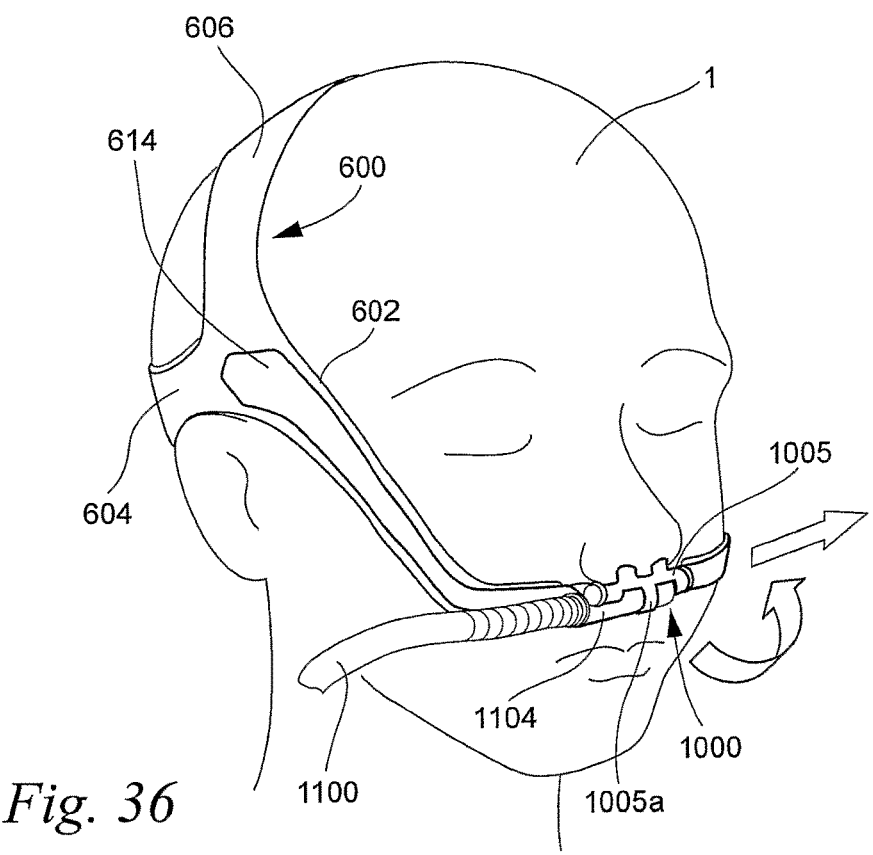
FIGS. 36 and 37 schematically illustrate an interface system according to another sample embodiment.
Figure 37:
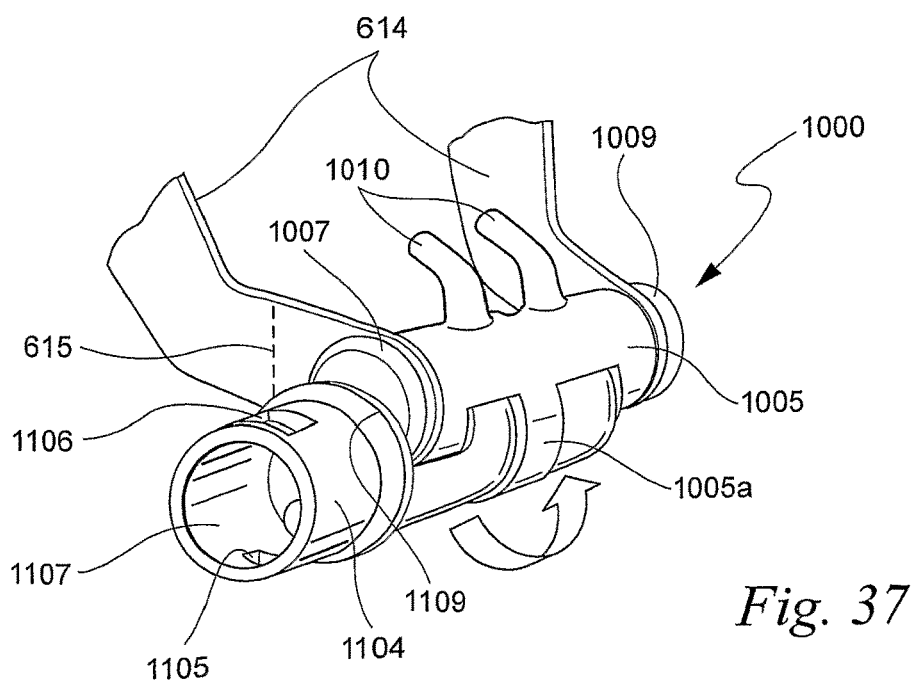
Figure 38:
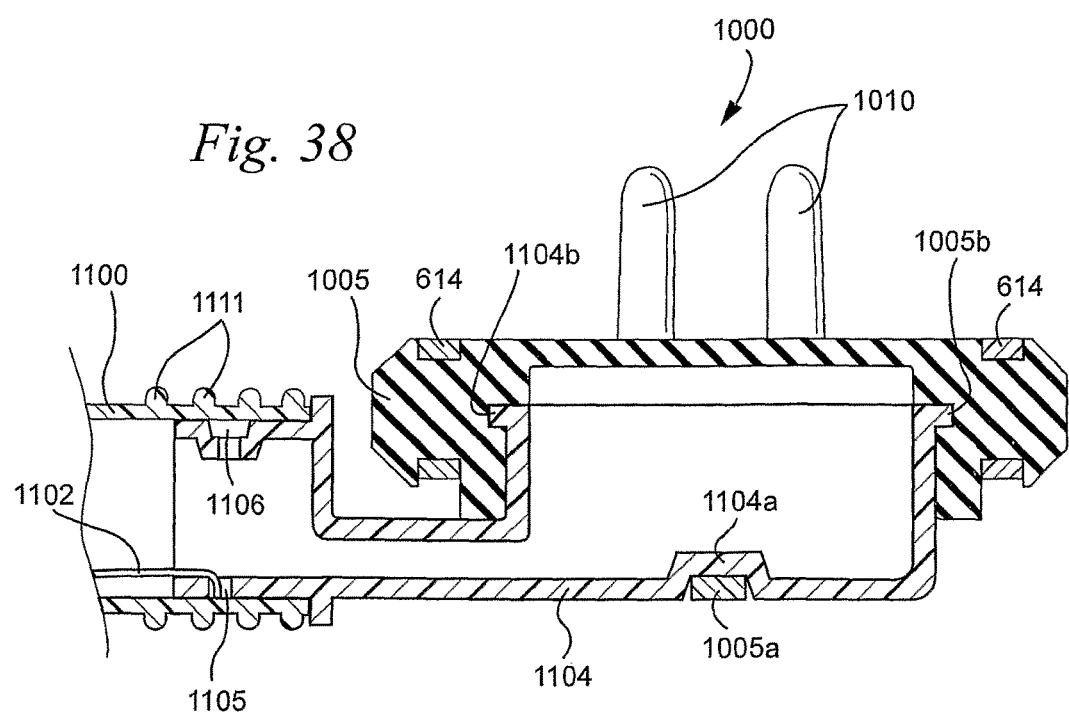
FIG. 38 schematically illustrates a tube and patient interface connection according to a sample embodiment.

Referring to FIGS. 36-38, a patient interface 1000 is connected to a tube 1100 on a side of the patient's face and the patient interface 1000 is held in contact with the face of the patient by a headgear 600. The headgear comprises side straps 602, a lower back strap 604 and an upper back strap 606. Stiffening elements, or rigidizers, 614 are provided to each of the side straps 602.

The barrel 1005 of the patient interface 1000 is connected at the first end 1007 to one rigidizer 614 and at the second end 1009 to the other rigidizer 614. The rigidizers 614 are configured to flex along a plane 615 to allow the headgear to conform to the patient's face.

As shown in FIG. 38, the tube connector 1104 includes a recessed circumferential area 1104a that receives an intermediate circumferential portion 1005a of the barrel 1005. The tube connector 1104 also includes a rim, or flange, 1104b that is accepted in a groove, or channel, 1005b in the barrel 1005. The tube connector 1104 and the barrel 1005 may be formed of materials of different durometers to assist in assembly of the tube connector 1104 into the barrel 1005. The engagement of the flange 1104b in the channel 1005b provides a substantially leak proof connection between the tube connector 1104 and the barrel 1005 of the patient interface 1000. The barrel 1005 may be formed of, for example, silicone, to provide a more robust connection between the tube connector 1104 and the barrel 1005.

As shown in FIG. 37, the tube connector 1104, and the associated tube 1100, may rotate with respect to the barrel 1005 of the patient interface 1000 to allow adjustment and fitting of the nasal prongs 1010 into the nares of the patient.

2.4.8 Tube Rotation Eighth Embodiment

Figure 39:
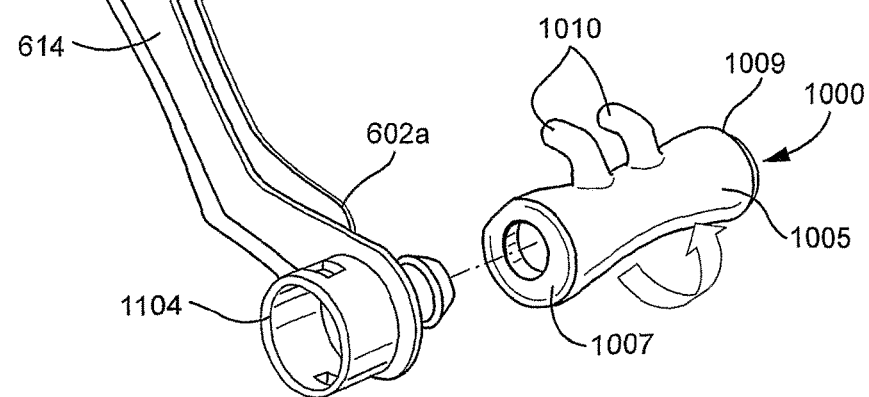
FIGS. 39 and 40 schematically illustrate an interface system according to another sample embodiment.
Figure 40:
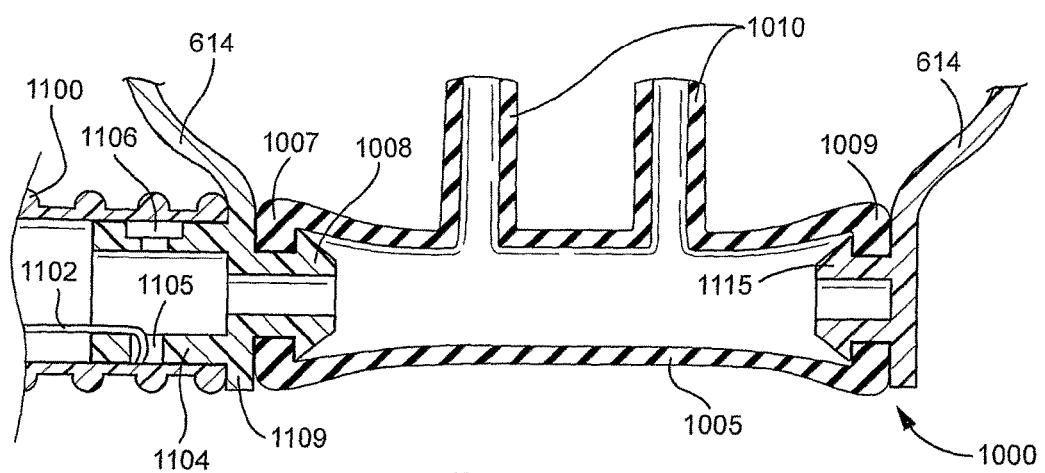

Referring to FIGS. 39 and 40, the tube connector 1104 may be integrally formed with the rigidizer 614 of the headgear 600. The second end 1108 of the tube connector 1104 may be inserted into the first end 1007 of the barrel 1005 of the patient interface 1000. It should be appreciated that the tube connector 1104 may also be inserted into the second side 1009 of the barrel 1005. As shown in FIG. 40, the rigidizer 614 connected to the second end 1009 of the barrel 1005 may have a plug 1115 integrally formed therewith to seal the second end 1009 of the barrel 1005. As shown in FIG. 39, the connection of the barrel 1005 to the rigidizer 614 of the headgear 600 permits the patient interface 1000 to pivot with respect to the headgear to permit the fitting of the nasal prongs 1010 into the nares of the patient. The rigidizers 614 are flexible, but guide the headgear on the patient's face and improve the stability of the interface.

The material of the rigidizer 614 and the integrally formed tube connector 1104 may be a different durometer than the material of the patient interface 1000 to permit easier assembly and to aid pivoting of the patient interface 1000 with respect to the headgear 600. The integrally formed rigidizer 614 and tube connector 1104 may be formed, for example, of silicone. The tube connector 1104 and the barrel 1005 may also have different finishes to assist in assembly and rotation between the tube connector 1104 and the barrel 1005. As shown in FIG. 39, the ends 602a of the side straps 602 may be adjusted, e.g. rounded, to allow the connection and engagement of the tube connector 1104 to the barrel 1005.

2.4.9 Tube Rotation Ninth Embodiment

Figure 41:
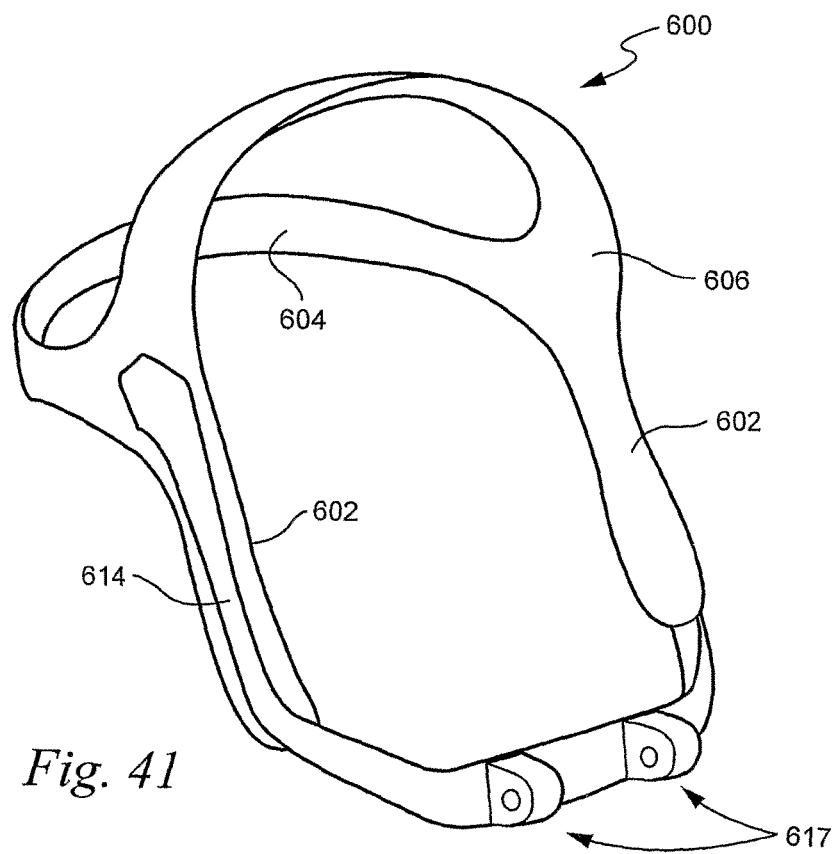
FIGS. 41 and 42 schematically illustrate an interface system according to another sample embodiment.
Figure 42:
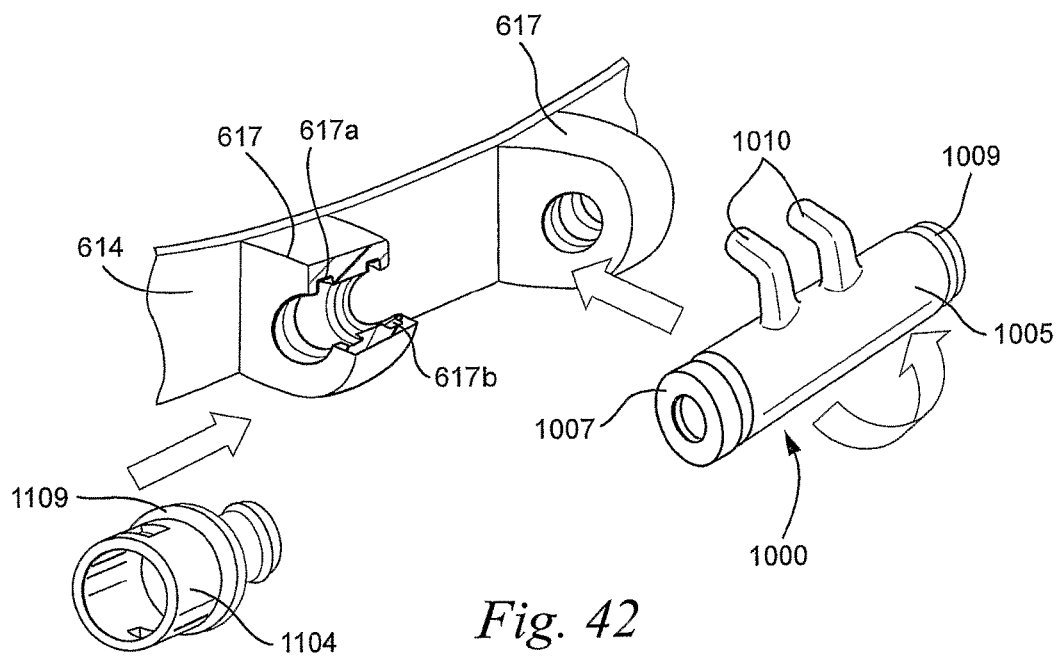

Referring to FIGS. 41 and 42, the rigidizers 614 of the headgear 600 may be formed as a single piece and include mounting bosses 617 that include a first circumferential channel or groove 617a for receipt of the flange 1109 of the tube connector 1104. The mounting bosses 617 also comprise second circumferential channels or grooves 617b to receive the first end 1007 and the second end 1009 of the barrel 1005 of the patient interface 1000. As shown in FIG. 42, upon insertion of the patient interface 1000 into the mounting bosses 617 of the one piece rigidizer 614, the patient interface 1000 may pivot with respect to the headgear 600 to permit fitting of the nasal prongs 1010 into the nares of the patient. The rigidizer 614 may be formed of, for example, silicone. The patient interface 1000 may also be formed, for example, of silicone. The silicone material is generally soft and provides a comfortable fit for the patient. The silicone is also flexible and allows the interface to conform to the patient's facial profile. The patient interface also presents a small component surface air in the path of the patient's exhalation. The tube connector 1104 may also be interchangeably connected at either end of the patient interface.

2.4.10 Tube Rotation Tenth Embodiment

Figure 43:
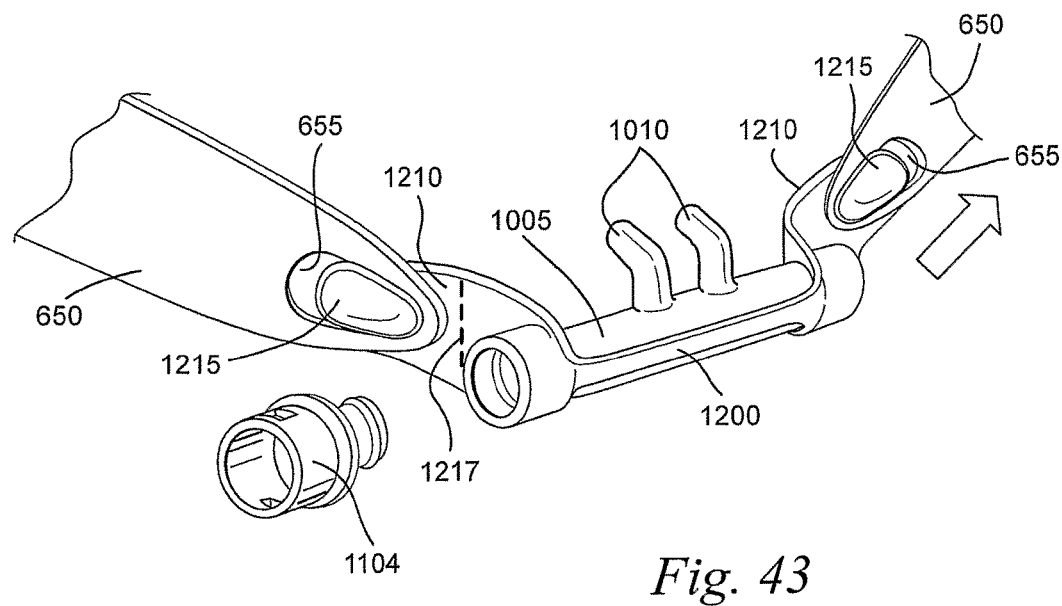
FIGS. 43 and 44 schematically illustrate an interface system according to another sample embodiment.
Figure 44:
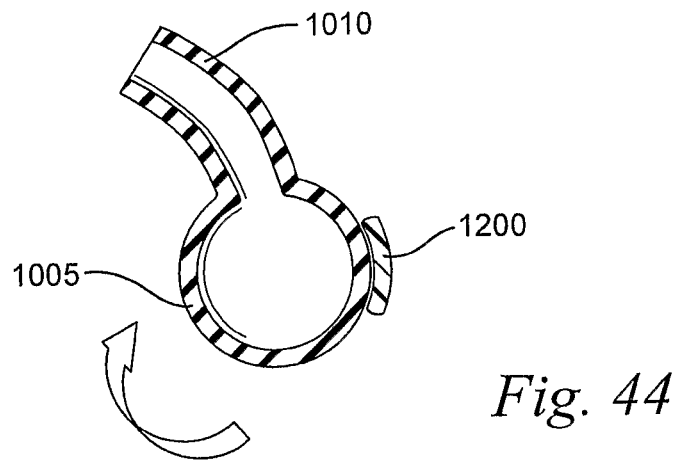

Referring to FIGS. 43 and 44, the patient interface may comprise a frame 1200 that pivotally receives the barrel 1005. The frame 1200 may comprise flexible extending members 1210 that each comprise connectors 1215 formed on an end thereof. The flexible members 1210 are each flexible generally about a plane 1217. A headgear 650 may comprise apertures 655 that each hook on to a respective connector 1215 of the flexible members 1210. In an alternative form, connectors 1215 may be provided to the headgear 650 and apertures 655 may be provided to the flexible members 1210 so that a reverse hook connection is possible. As shown in FIG. 44, the connection of the frame 1200 to the headgear 650 holds the frame 1200 in a stationary position while the barrel 1005 of the patient interface is pivotable with respect to the frame 1200 to permit adjustment of the nasal prongs 1010. The tension of the straps of the headgear 650 is not transmitted through the frame 1200 to the barrel 1005 of the patient interface.

The headgear 650 may be formed of fabric and plastic, for example, a laminate of fabric and plastic. The tube connector 1104 may also be formed, for example, of plastic as well as the frame 1200. The barrel 1005 and the nasal prongs 1010 may be formed, for example, of silicone.

The interface may be donned, or removed, by the patient by pulling the connected headgear and patient interface over, or off, the patient's head. The interface may also be donned, or removed, by connecting, or disconnecting, a connector 1215 with, or from, an aperture 655 of the headgear 650.

2.5 Top Lip Stabilization 2.5.1 Top Lip Stabilization First Embodiment

Figure 45:
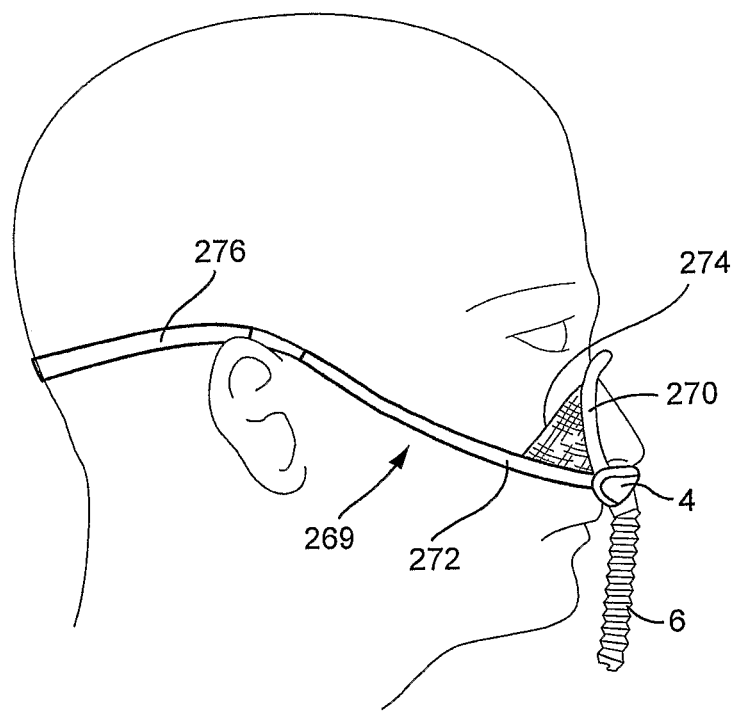
FIG. 45 schematically illustrates an interface system according to another sample embodiment.

Referring to FIG. 45, the patient interface 4 is connected to the retractable tube 6 and held in contact with the nose of the patient by a headgear system 269. The headgear system 269 includes a first rigid member 270 which extends over the bridge of the nose of the patient. Second rigid members 272 are connected to the patient interface 4 on each side of the patient's face at a region between the upper lip of the patient and the bottom of the nose of the patient. A soft member 274 is provided between the first rigid member 270 and the second rigid members 272 to engage the crease between the sides of the nose of the patient and the patient's face. The soft member 274 may be a flexible member, for example a fabric member. A back strap 276 is connected to the second rigid member and extends over the ears of the patient and around the back of the patient's head to maintain the patient interface 4 in engagement with the nose of the patient. The back strap may be formed, for example, of elastic, silicone, cloth, or some combination thereof.

2.5.2 Top Lip Stabilization Second Embodiment

Figure 46A:
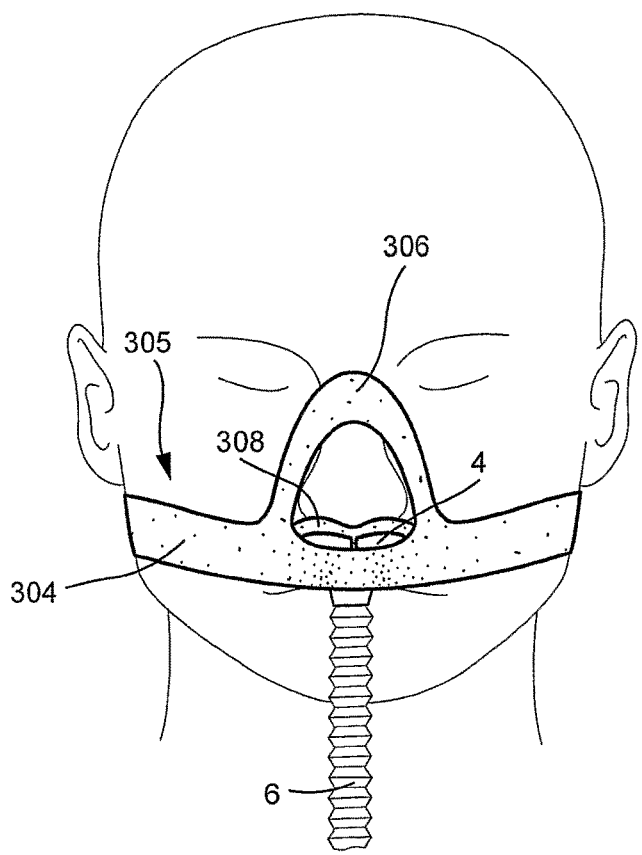
FIGS. 46*a* and 46*b* schematically illustrate an interface system according to another sample embodiment.
Figure 46B:
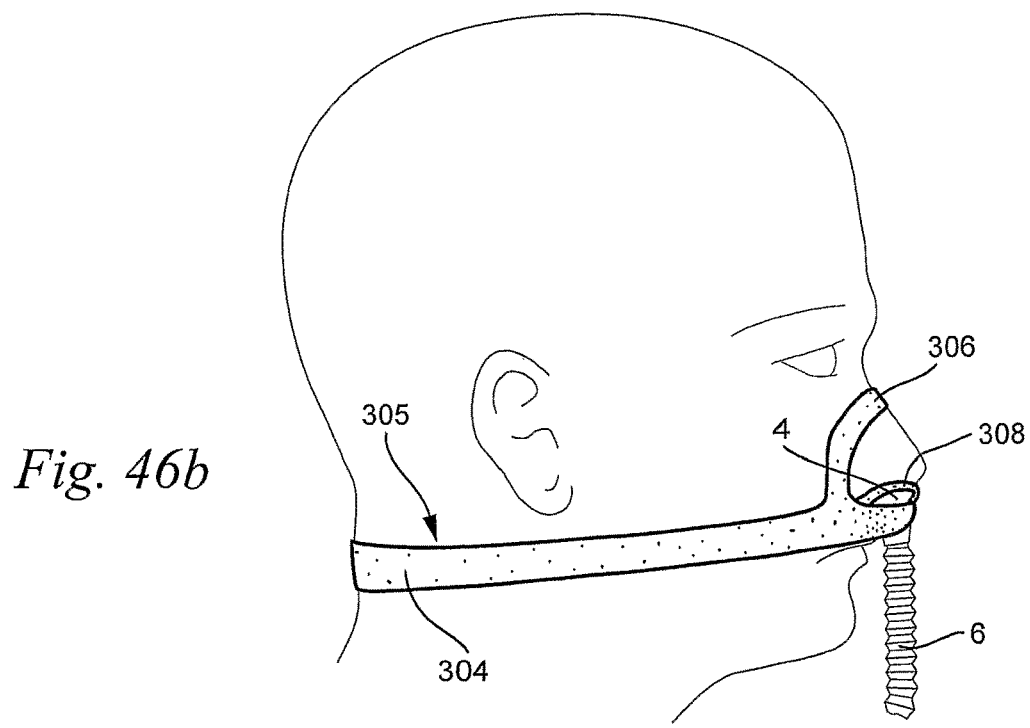

Referring to FIGS. 46a and 46b, the patient interface 4 is held against the patient's upper lip in sealing engagement with the nares of the patient's nose by a headgear 305 that may comprise a strap 304 that is configured to encircle the head of the patient and extend below the patient's ears. The strap 304 may also comprise a nose bridging strap 306 that extends over the bridge of the nose of the patient. The headgear 305 may also include an upper lip bridging strap 308 that is configured to engage the patient interface 4 and hold the patient interface 4 in sealing engagement with the nares of the patient's nose.

The straps 304, 306, 308 may be formed, for example, of elastic, silicone, fabric, TPE, or combinations thereof.

2.5.3 Top Lip Stabilization Third Embodiment

Figure 47A:
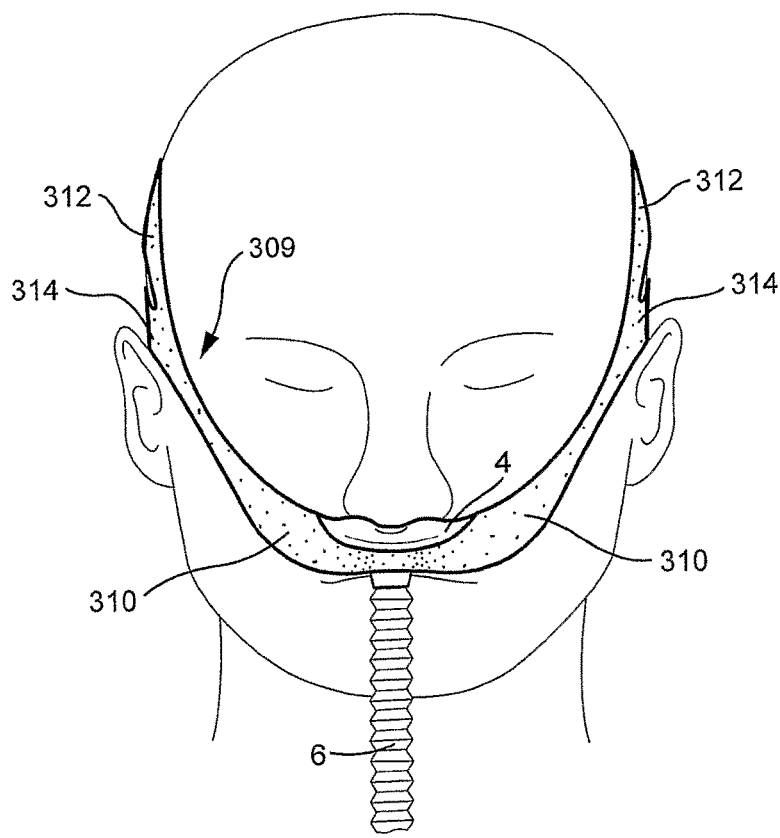
FIGS. 47*a* and 47*b* schematically illustrate an interface system according to another sample embodiment.
Figure 47B:
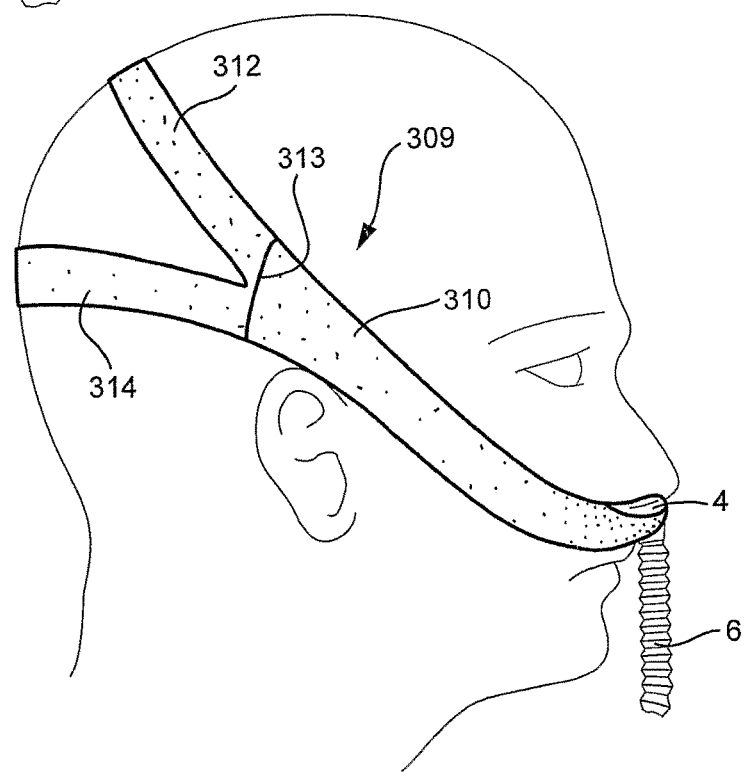

As shown in FIGS. 47a and 47b, the patient interface 4 may be held against the patient's top lip in sealing engagement with the nares of the nose of the patient by a headgear 309 that may comprise side straps 310 extending along each side of the patient's face and over the patient's ears. The side straps 310 may be connected to an upper rear strap 312 and a lower rear strap 314 at a connection 313. It should also be appreciated, however, that the straps 310, 312, 314 may be integrally formed as a single strap. The angle between the upper rear strap 312 and the lower rear strap 314 may be adjusted to provide a stable seal between the patient interface 4 and the nares of the patient's nose. Generally speaking, the larger the angle between the upper rear strap 312 and the lower rear strap 314, the greater the stability of the seal of the patient interface 4 with the nares of the nose of the patient.

2.5.4 Top Lip Stabilization Fourth Embodiment

Figure 48A:
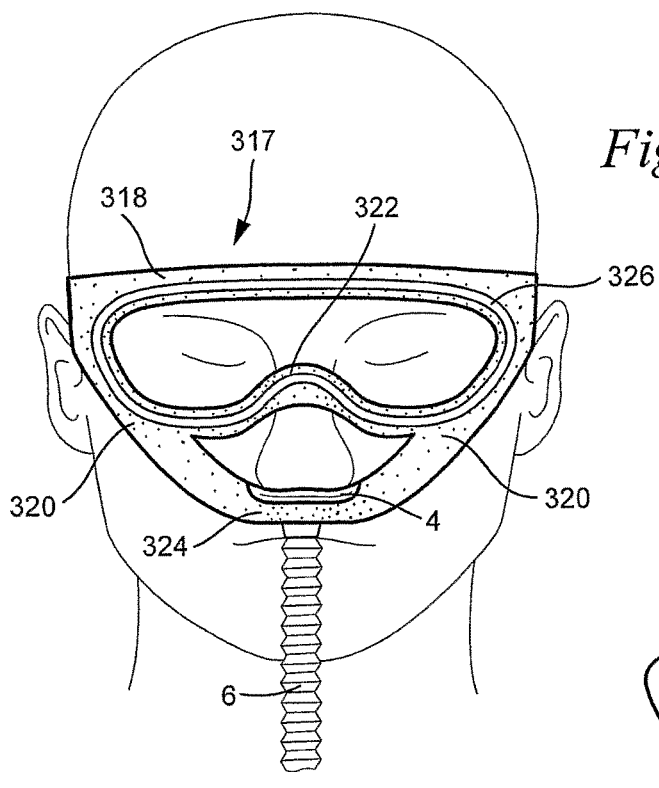
FIGS. 48*a*-48*c* schematically illustrate an interface system according to another sample embodiment.
Figure 48C:
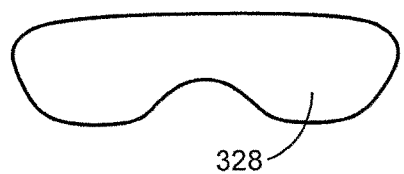
Figure 48B:
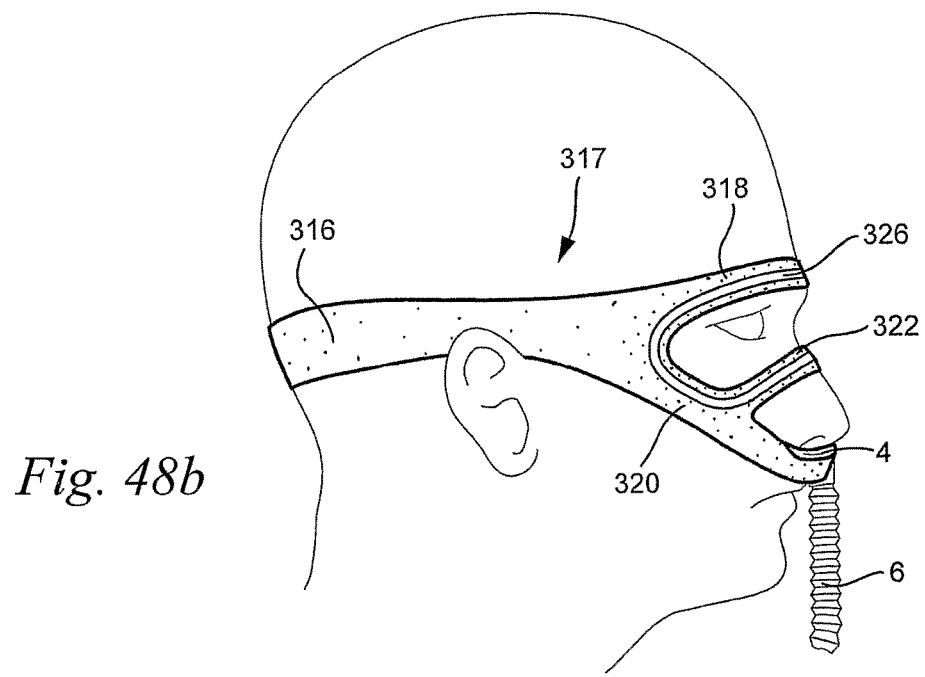

Referring to FIGS. 48a-48c, an interface 4 according to another sample embodiment comprises a headgear 317 comprising a strap 316 that is configured to extend around the patient's head over the patient's ears. The strap 316 may comprise an upper front strap 318 and a lower front strap 320. The upper front strap 318 is configured to extend across the patient's forehead above the patient's eyes and the lower front straps 320 are configured to extend along the side of the patient's face from the upper front strap 318 toward the nose of the patient. The lower front straps 320 may comprise an upper lip bridging strap 324 that is configured to engage the patient interface 4 and maintain the patient interface 4 in a sealing engagement with the nares of the nose of the patient.

As shown in FIGS. 48a and 48b, a stiffening element, or rigidizer, 326 may be provided on the front of the headgear 2, for example extending along the upper front strap 318 and along portions of the lower front straps 320. The stiffening element 326 may extend over the bridge of the patient's nose along with a nose bridging strap 322 that extends between the lower front straps 320. The stiffening element 326 may be attached to the straps by, for example, stitching or adhesive. It should also be appreciated that the stiffening element 326 may be laminated with the straps of the headgear.

Referring to FIG. 48c, an eye mask or screen 328 may be provided that is connectable to the headgear 317. For example, the eye mask or screen 328 may be insertable under the straps 318, 319, 322 of the headgear 317, for example, along the edges of the eye mask or screen 328. As another example, the eye mask or screen 328 may be attachable to the stiffening element 326 by, for example, hook and loop fasteners or by mechanical fasteners, for example, clips. It should also be appreciated that the stiffening element 326 may include magnetic portions and the eye mask or screen 328 may include corresponding magnetically attracted portions to attach the eye mask or screen 328 to the headgear 317.

The straps 316, 318, 319 320, 322, 324 may be formed of fabric, elastic, TPE, silicone, and/or combinations thereof.

2.5.5 Top Lip Stabilization Fifth Embodiment

Figure 49A:
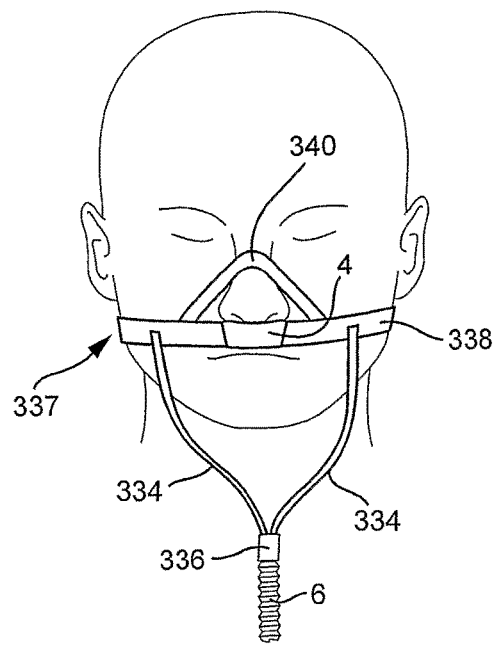
FIGS. 49*a* and 49*b* schematically illustrate an interface system according to another sample embodiment.
Figure 49B:
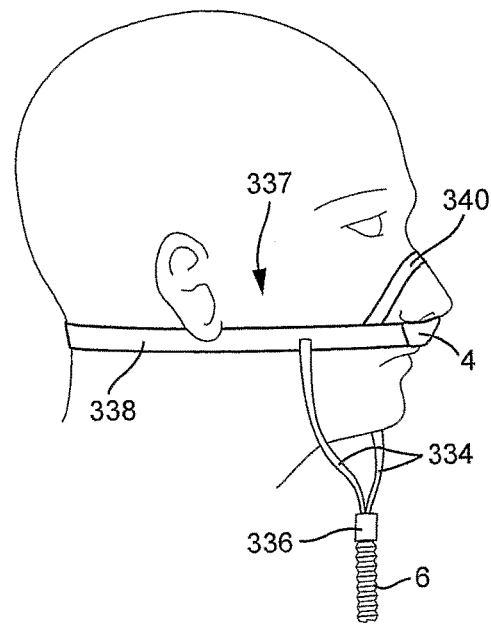

Referring to FIGS. 49a and 49b, a patient interface 4 is held against the patient's top lip and in contact with the nose of the patient by a headgear system 337. The headgear system 337 may comprise a strap 338 that extends around the head of the patient, and below the patient's ears. A nose bridging strap 340 may extend across the bridge of the patient's nose and be connected at opposite ends to the strap 338.

The strap 338 may be configured as a tube or conduit for delivery of the flow of breathable gas to the patient interface 4. The flow of breathable gas is delivered by a retractable tube 6 and a connector 336 is configured to connect the retractable tube 6 to air delivery hoses 334 that are connected to the strap 338 to deliver the flow of breathable gas to the patient interface 4.

2.5.6 Top Lip Stabilization Sixth Embodiment

Figure 50A:
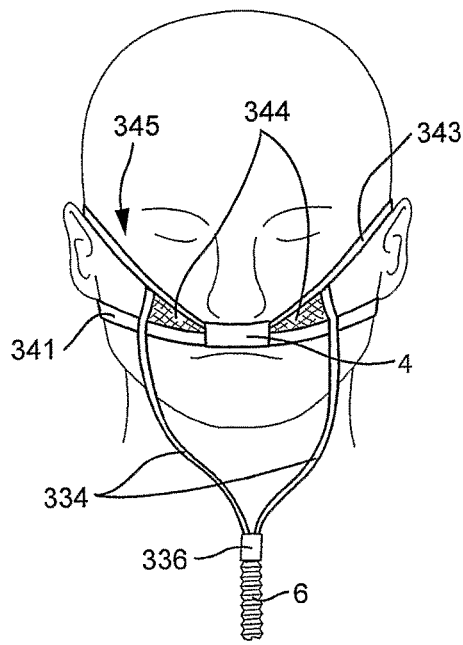
FIGS. 50*a* and 50*b* schematically illustrate an interface system according to another sample embodiment.
Figure 50B:
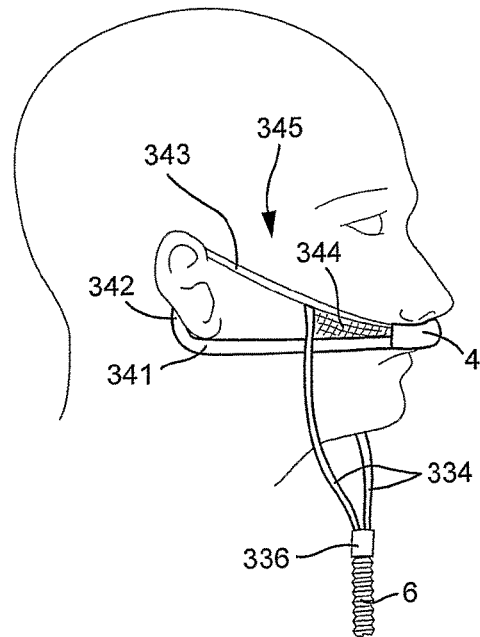

As shown in FIGS. 50a and 50b, a patient interface 4 is held in engagement with the top lip and nose of the patient by a headgear system 345 that may comprise lower straps 341 that are configured to extend below the ears of the patient. Upper straps 343 may also be configured to be connected to the patient interface 4 and connect with the lower straps 341 by straps 342 that extend around the ears of the patient. Fabric 344 is provided between the upper straps 343 and the lower straps 341 to conform to the sides of the patient's face. The flow of breathable gas may be delivered by a retractable tube 6 which is connected to air delivery hoses 334 by a connector 336. The air delivery hoses 334 are connected to the upper straps 343 which are configured as hoses or tubes for delivery of the flow of breathable gas to the patient interface 4.

2.5.7 Top Lip Stabilization Seventh Embodiment

Referring to FIGS. 51a and 51b, the patient interface 4 may be connected to a strap 347 that is configured to hold the patient interface 4 against the top lip and nose of the patient. The strap 347 may include slots 349 that are configured to receive an adjustable strap end 348 of an ear engaging strap 346. The adjustable strap end 348 may be fastened to the ear engaging strap 346 by hook and loop fastener material 350. For example, the adjustable strap end 348 may include hooks and the fastener material 350 may comprise loops for permitting attachment, detachment and adjustment of the position of the adjustable strap end 348 with respect to the ear engaging strap 346.

2.5.8 Top Lip Stabilization Eighth Embodiment

Referring to FIG. 52, the tube 1100 may be connected to the patient interface 1000 along a side of the patient's face. A headgear 600, comprising side straps 602, a lower back strap 604, and an upper back strap 606, may be provided to maintain the patient interface 1000 in contact with the top lip and nose of the patient. The side straps 602 (only one shown) may be provided with stiffening elements, or rigidizers, 614. The rigidizers 614 may be formed of plastic or silicone and act to guide the headgear through the correct area of the patient's face. The rigidizers 614 also prevent twisting and/or buckling of the side straps 602 when adjusting the patient interface 1000 and/or the tube 1100. The rigidizers 614 may also be thinner than rigidizers currently used in CPAP apparatus in which a seal is formed with the patient's airways. In the embodiment shown in FIG. 52, in which the patient interface 1000 may include nasal prongs 1010 that do not form a seal with the patient's nares, the headgear, and the rigidizers, are not required to direct strap tension vectors for forming a seal.

2.5.9 Top Lip Stabilization Ninth Embodiment

Figure 53:
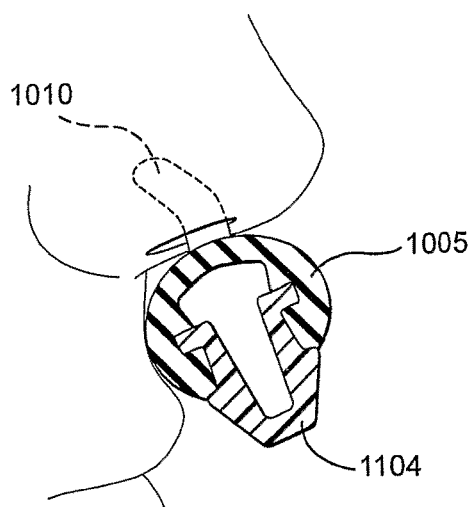
FIG. 53 schematically illustrates an interface system according to a sample embodiment.

Referring to FIG. 53, the barrel 1005 of the patient interface may be connected to a tube connector 1104. The barrel 1005 and the tube connector 104 may be formed of different material. As shown in FIG. 53, the barrel 1005 may contact the upper lip of the patient and have a hardness of about 70-80 on the Shore A durometer scale.

2.5.10 Top Lip Stabilization Tenth Embodiment

Figure 54:
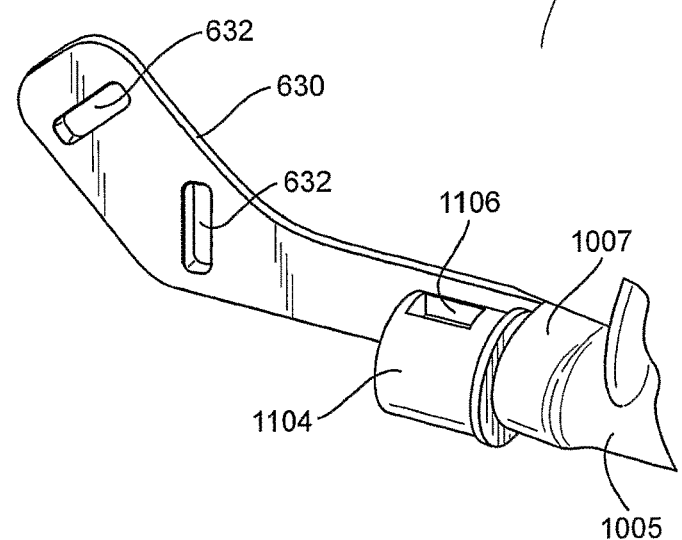
FIG. 54 schematically illustrates an interface system according to another sample embodiment.

Referring to FIG. 54, the barrel 1005 may be connected to a frame 630 on the first side 1007 and on the second side 1009. The frame 630 may comprise two slots 632 configured to receive the end of a strap, such as a side strap. For example, the strap may be provided with hook and loop type fasteners at the end of the strap and may be threaded through the slots 632 so that the strap is positioned from the frame 630 to the patient's face.

The frame 630 may be formed of, for example, silicone and engage the patient's face in the region of the top lip to hold the barrel in position under the patient's nares. The slots 632 receive the end of straps and the ends of the straps will be in contact with sides of the patient's face. The frame 630 thus presents a less obtrusive appearance than frames in which the headgear straps are connected to an outer surface of the frame.

2.5.11 Top Lip Stabilization Eleventh Embodiment

Figure 55:
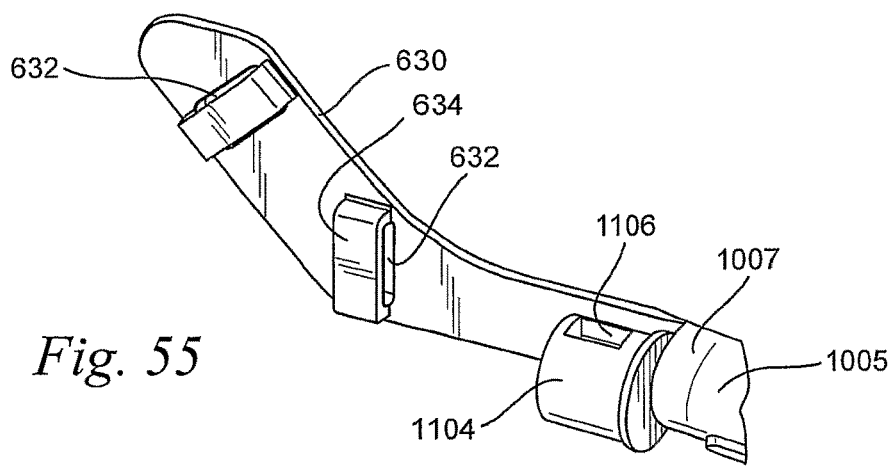
FIG. 55 schematically illustrates an interface system according to another sample embodiment.
Figure 56:
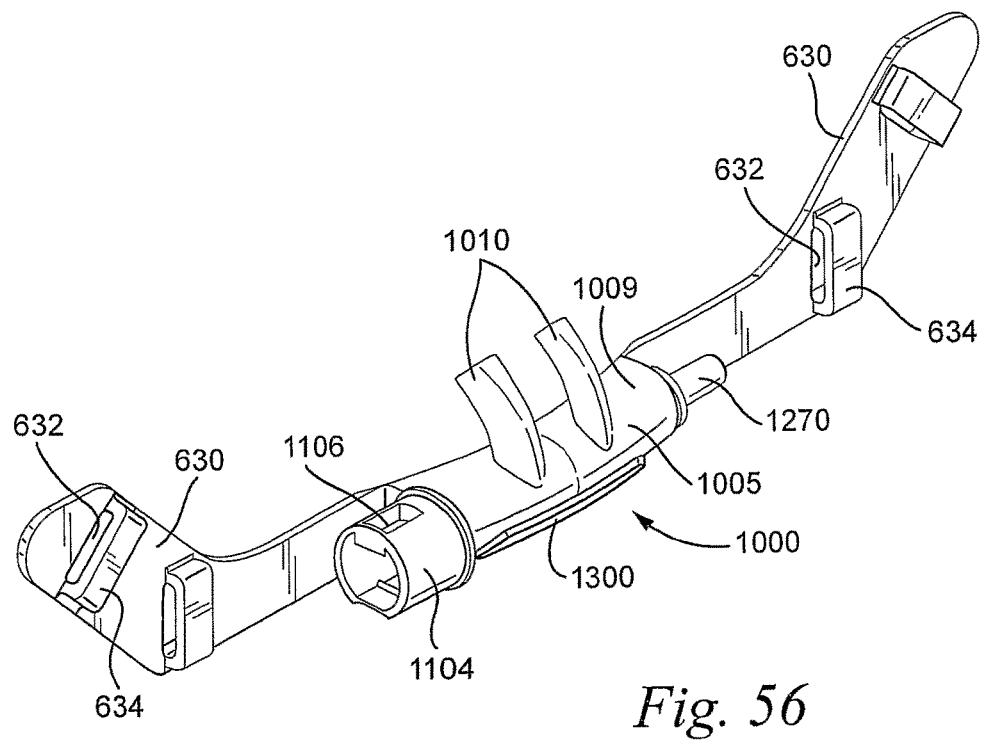
FIGS. 56-59 schematically illustrate an interface system according to another sample embodiment.
Figure 57:
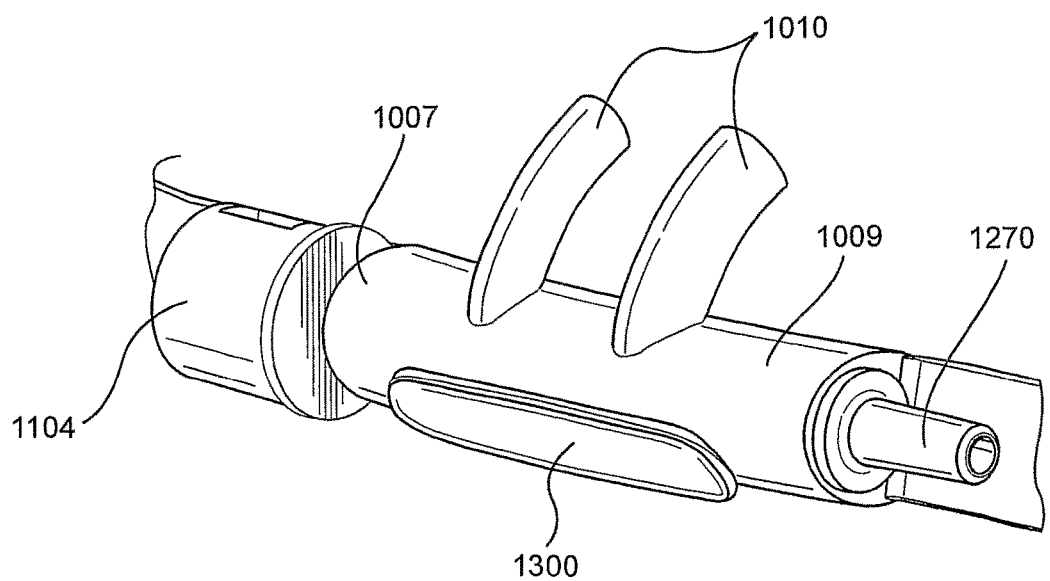

Referring to FIG. 55, the frame 630 may also comprise strap guides 634 placed over the slots 632. The straps may then be connected to the strap guides so that the headgear 630 is provided between the straps and the patient's face. The raised strap guides 634 provide a more robust connection with the straps and allow more of the frame 630 to be in contact with the patient's face than the previous embodiment as the headgear straps are not in contact with the patient's face. The frame 630 may be formed, for example, of silicone, and be in contact with, the patient's face to provide stability to the headgear.

2.5.12 Top Lip Stabilization Twelfth Embodiment

Figure 58:
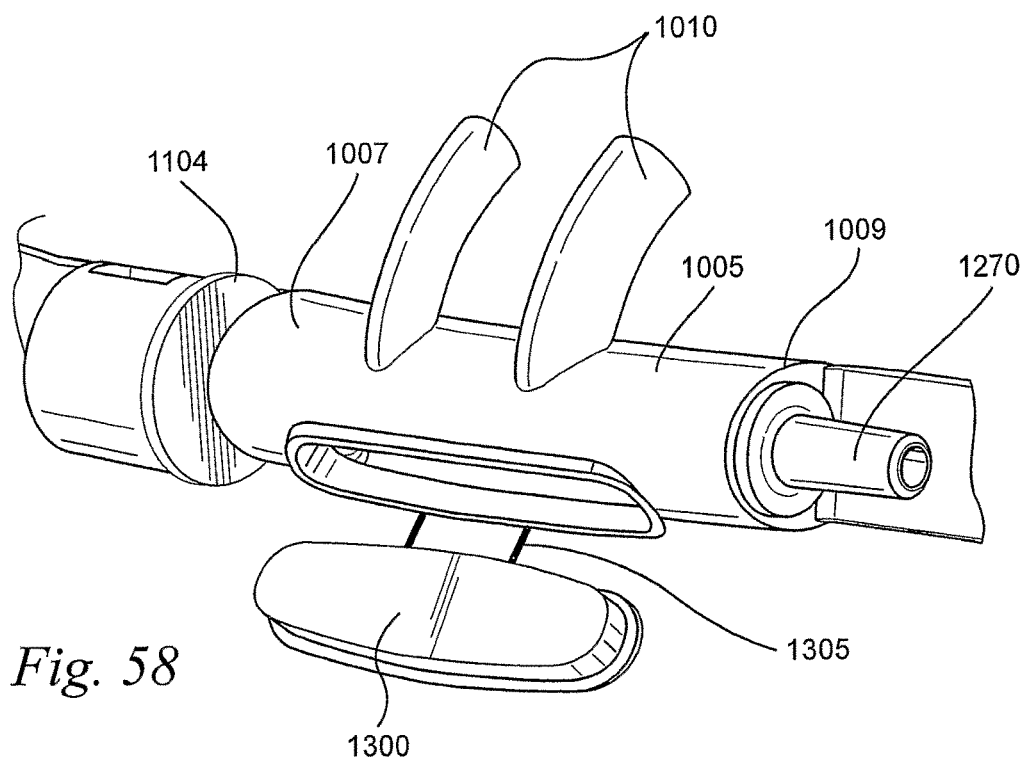
Figure 59:
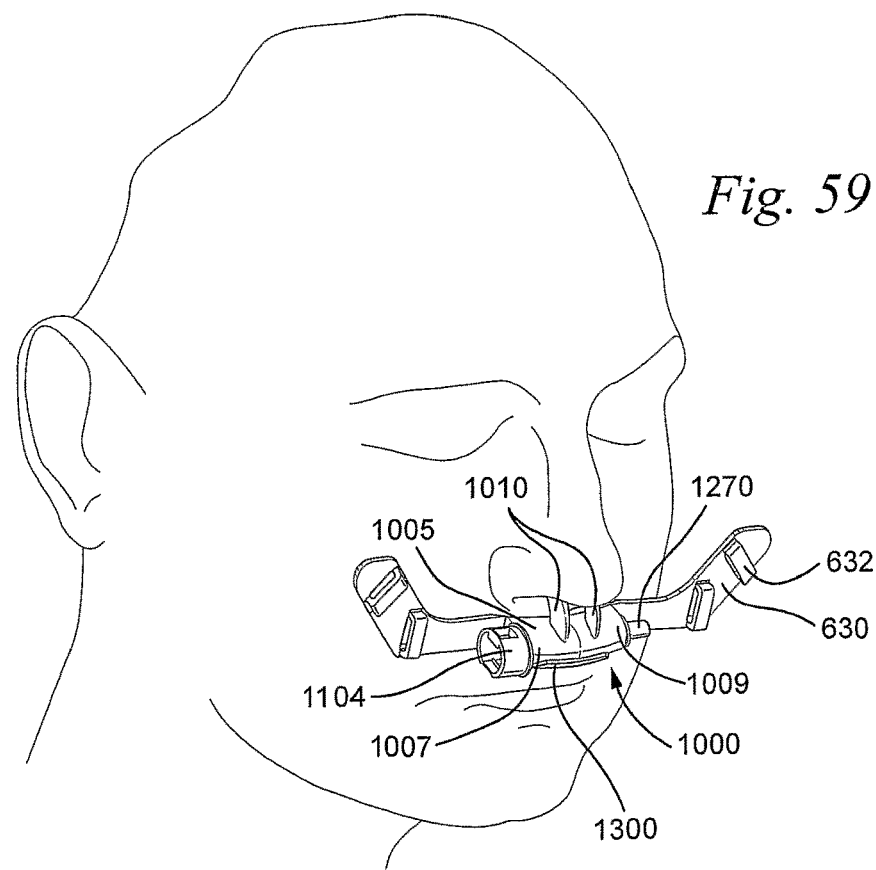

Referring to FIGS. 56-59, the patient interface 1000 may comprise a body plug 1300 that is connected to the barrel 1005 of the patient interface by tethers 1305, shown in FIG. 58. The body plug 1300 covers an opening in the barrel 1005 that allows de-molding of the nasal prongs 1010. The body plug 1300 seals and completes the patient interface and may be formed, for example, of silicone or rigid plastic. The body plug 1300 has a planar sealing rim to generate compression in the aperture of the barrel 1005 and seal the patient interface. It should also be appreciated, however, that the body plug 1300 may be permanently fastened to the barrel 1005, for example, by adhesive.

As shown in FIGS. 56-59, the tube connector 1104 may be connected to the barrel 1005 at the first end 1007. A pressure port 1270 may be provided to the second end 1009 of the barrel 1005 to allow for reading a pressure in the patient interface 1000, for example, during the use of the patient interface in a sleep laboratory. The pressure port 1270 may be replaced with a plug, such as one previously described, for use by the patient at home.

2.6 Ear Comfort
2.6.1 Ear Comfort First Embodiment

Referring to FIGS. 60a-60d, the patient interface 4 is connected to the retractable tube 6 and is maintained in contact with the nose of the patient by ear straps 298 which extend around the ears of the patient. A semi-rigid, deformable ear profile 300 is engaged by each ear strap 298 and each profile 300 is configured to engage the back of the patient's ears. As shown in FIGS. 60a and 60b, the ear profiles 300 keep the ear straps 298 away from the earlobes of the patient and prevent the ear straps 298 from digging into the ears of the patient. As shown in FIGS. 60c and 60d, the semi-rigid deformable ear profiles 300 have a U-shaped cross-section and are conformable to the shape of the patient's ears.

2.6.2 Ear Comfort Second Embodiment

Figure 61:
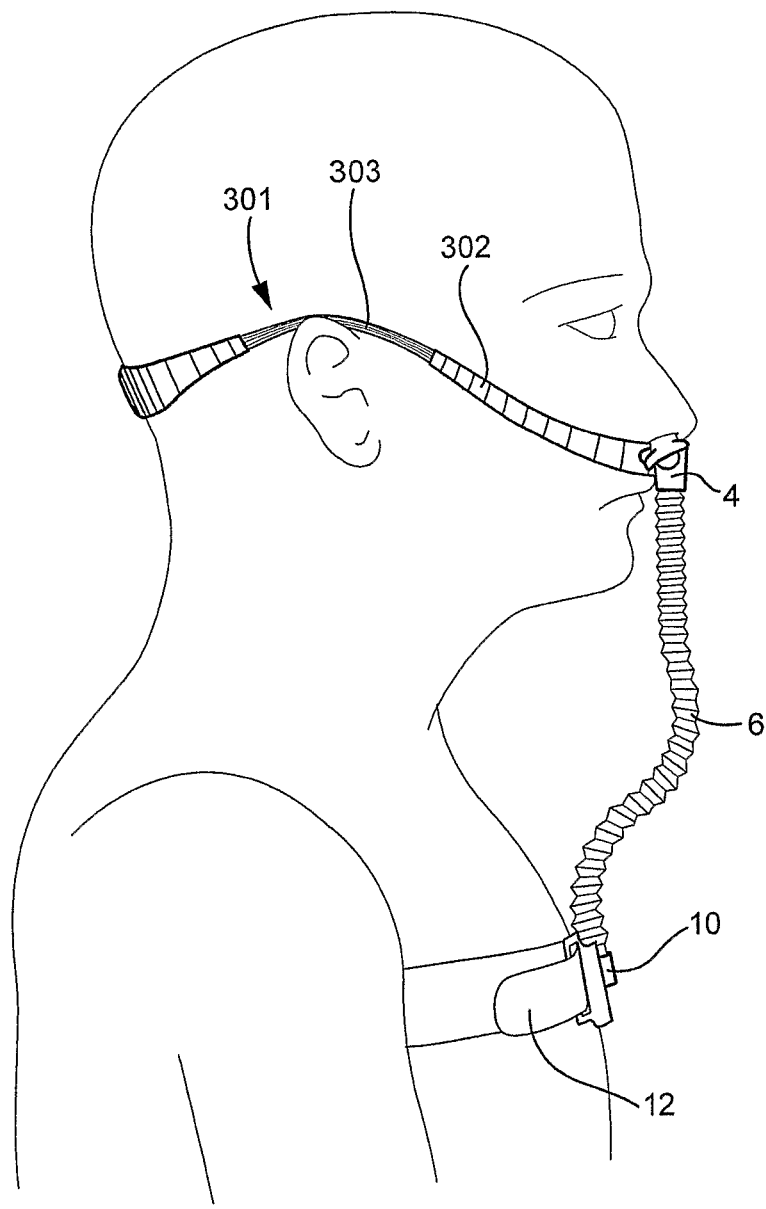
FIG. 61 schematically illustrates an interface system according to another sample embodiment.

Referring to FIG. 61, the patient interface is connected to the retractable tube 6 and maintained in contact with the nose of the patient by a headgear system 301 including a strap 302 that extends along the sides of the patient's face, over the ears of the patient, and around the back of the patient's head. The strap 302 may comprise an elastic portion 303, or two elastic portions, one on each side of the patient's head in the region of the patient's ears, or any other number of elastic portions, to maintain the patient interface 4 in sealing engagement with the patient's airways and improve comfort. The retractable tube 6 is connected to a cuff, or connector, 10 that is attached to a strap 12 configured to extend around the chest of the patient. The cuff 10 allows the retractable tube 6 to be connected to an air delivery hose or conduit that may be retractable or non-retractable, for delivery of a flow of breathable gas from a flow generator. The strap, cuff, and hose or conduit may be as described, for example, in U.S. application Ser. No. 12/211,896, filed Sep. 17, 2008, the entire contents of which are incorporated herein by reference.

The headgear system 301 may be formed from any suitable material, for example silicone. In another form, the headgear system 301 may be formed of one or more materials with differing hardness, for example higher hardness at, or near, the cheeks. This may improve stability of the patient interface 4.

2.6.3 Ear Comfort Third Embodiment

Referring to FIGS. 62a-62d, the headgear system 365 for maintaining the patient interface 4 in engagement with the nose of the patient may comprise ear engaging straps 362 that are connected to the patient interface 4. The headgear system 2 may also comprise a strap 366 that is configured to extend above the patient's ears and around the back of the patient's head. A top strap 368 may be connected to the strap 366 to extend across the top of the back of the patient's head.

Figure 62A:
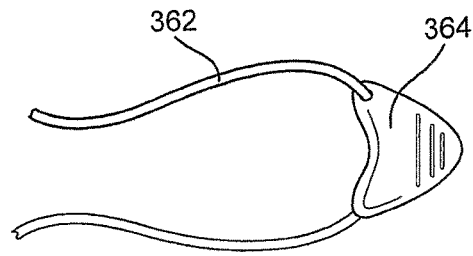
FIGS. 62*a*-62*d* schematically illustrate an interface system according to another sample embodiment.
Figure 62B:
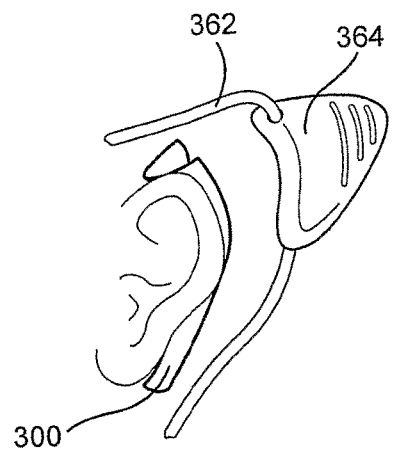
Figure 62C:
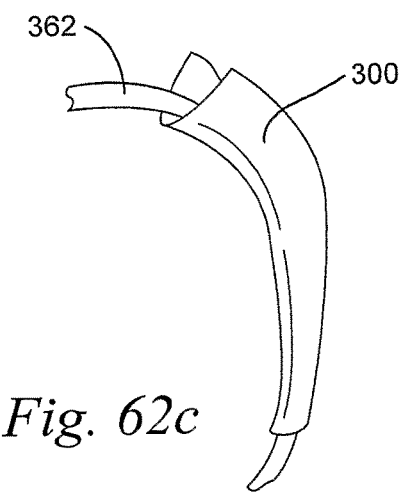
Figure 62D:
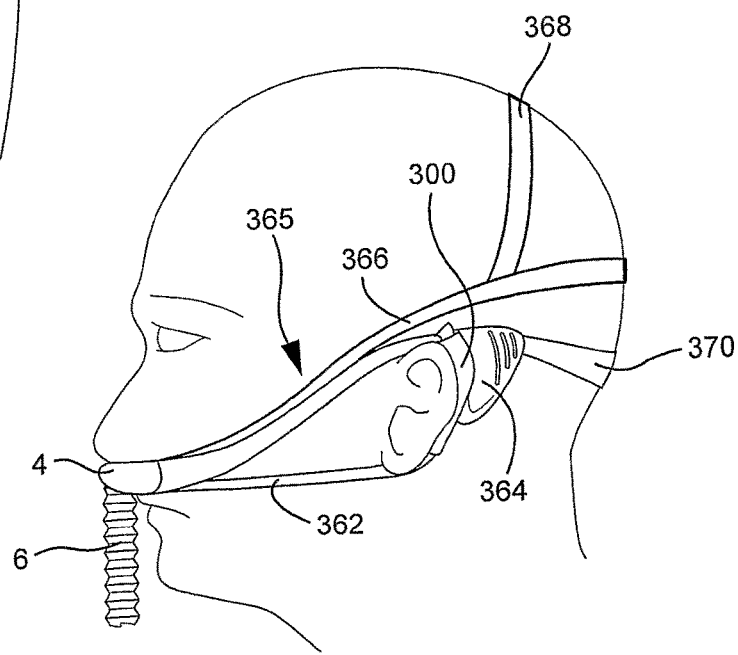

As shown in FIGS. 62b and 62c, the ear engaging straps 362 may be supported by ear engaging profiles 300 similar to those described above. In addition, the ear engaging straps 362 may each be threaded through a stiffening element, or rigidizer, 364 that are each attached to a rear strap 370 that extends around the back of the patient's head and connects the stiffening elements 364 provided on each side of the patient's head. The stiffening elements 364 are configured to be received by the ear profiles 300, as shown in FIGS. 62b and 62d. As also shown in FIG. 62d, the flow of breathable gas may be delivered to the patient interface 4 by connecting the retractable tube 6 to the patient interface 4.

Figure 63A:
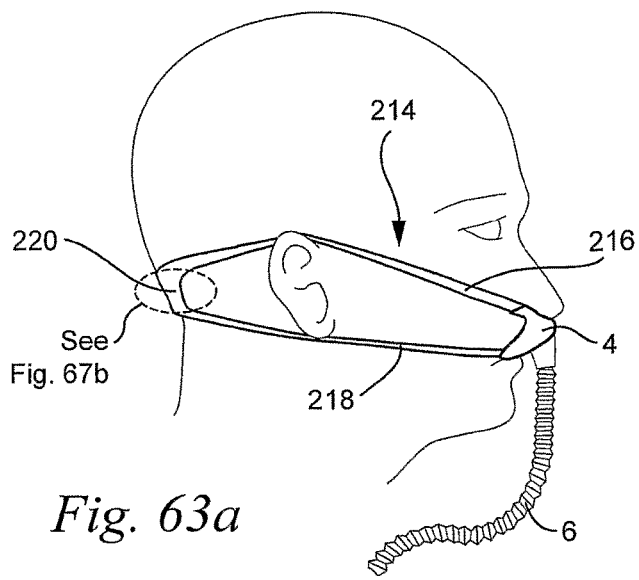
FIGS. 63*a* and 63*b* schematically illustrate an interface system according to another sample embodiment.
Figure 63B:
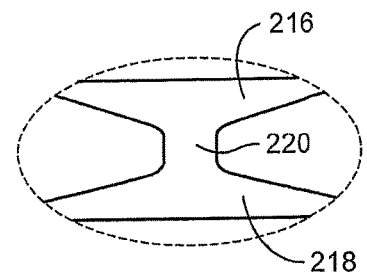

2.7 Headgear Configurations
2.7.1 Headgear Configuration First Embodiment Referring to FIGS. 63a and 63b, the retractable tube 6 is secured to a patient interface 4. The patient interface 4 may include a mask, nasal cannulae or prongs as described above. The nasal cannulae or prongs may be configured to provide the flow of breathable gas to the nares of the patient without sealing the against the patient's airways.

According to another variant, the patient interface may include a cushion including nasal pillows that are configured to sealingly engage the nares of the patient. Cushions and nasal pillows usable with the sample embodiments of the invention are described in, for example, U.S. Patent Application Publications 2007/0144525 A1 and 2006/0283461 A1, the entire contents of each being incorporated herein by reference. It should also be appreciated that the cushion and nasal pillows usable with the sample embodiments of the invention may be as described in, for example, U.S. Pat. No. 7,318,437, the entire contents of which are incorporated herein by reference.

The patient interface 4 is maintained in contact with the nose of the patient by a headgear 214. The headgear 214 includes a headgear top strap 216 and a headgear bottom strap 218. A headgear connector strap 220 may be provided between the top strap 216 and the bottom strap 218. As shown in FIGS. 63a and 63b, the connector strap 220 is provided to engage a back of the patient's head, although it should be appreciated that the connector strap may be provided at another location, or that multiple connector straps may be provided between the top strap 216 and the bottom strap 218 at a plurality of locations.

2.7.2 Headgear Configuration Second Embodiment

Figure 64:
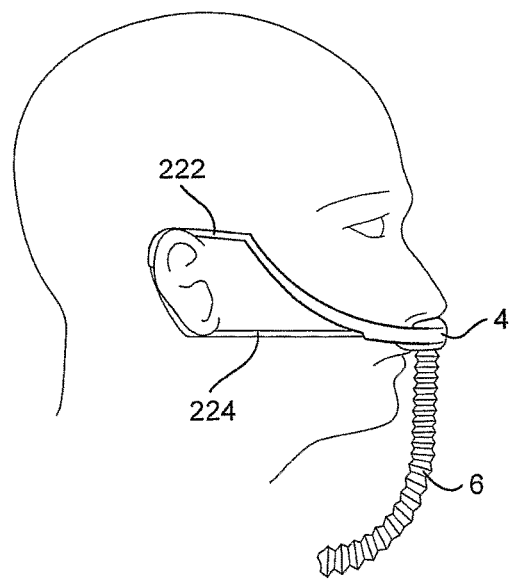
FIG. 64 schematically illustrates an interface system according to another sample embodiment.

As shown in FIG. 64, in another sample embodiment, the retractable tube 6 is connected to the patient interface 4 which is supported by a semi-rigid or rigid frame 222. It should be appreciated that the patient interface 4 and the rigid frame 222 may be formed as a one piece unitary structure.

The frame 222 is configured to extend on opposite sides of the patient's face and engage the patient's ears in a manner similar to a pair of eyeglasses. A flexible supporting strap 224 may be connected to one end of the frame 222 positioned generally at the top or behind the patient's ears and extend under the patient's ears to maintain the frame 222 in contact with the ears and to maintain the patient interface 4 in engagement with the nares of the patient's nose.

Flexible supporting strap 224 may be connected from the end of the frame 220 to the patient interface 4 to provide stability to the patient interface 4. Supporting strap 224 may also connect from the end of the frame 222 to another portion of the frame 222 (as shown in FIG. 64). Supporting strap 224 may be made from a flexible material such as elastic or silicone. Alternatively, supporting strap 224 could be made from any material desired, for example TPE.

2.7.3 Headgear Configuration Third Embodiment

Figure 65:
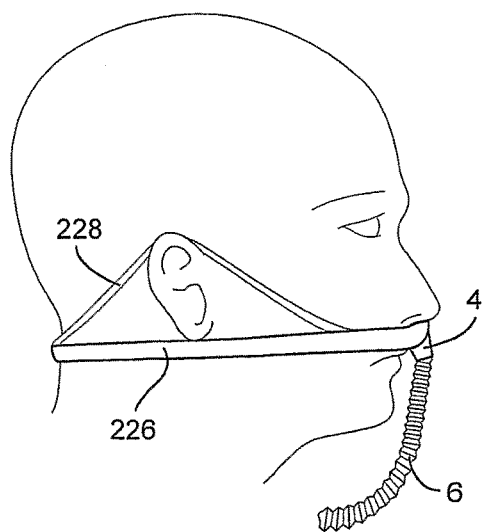
FIG. 65 schematically illustrates an interface system according to another sample embodiment.

According to another sample embodiment shown in FIG. 65, the retractable tube 6 is connected to the patient interface 4 and the patient interface 4 is maintained in contact with the nose of the patient by a flexible bottom strap 226 and a flexible top strap 228 that is configured to extend over the ears of the patient. The flexible bottom and top straps 226, 228 may comprise, for example, elastic. The straps may be formed of, for example, BREATHOPRENE®, manufactured by Accumed. The flexible bottom strap 226 may be similar to the strap used in ResMed's SWIFT™ mask. The flexible bottom strap 226 may have a similar strap length adjustment (i.e. with a buckle) as in ResMed's SWIFT™ mask.

2.7.4 Headgear Configuration Fourth Embodiment

Figure 66:
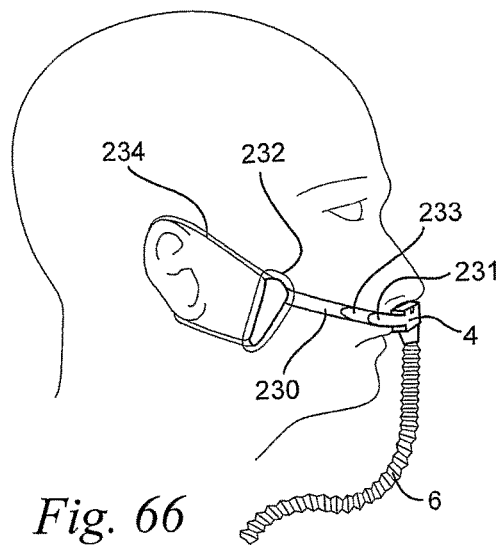
FIG. 66 schematically illustrates an interface system according to another sample embodiment.

Referring to FIG. 66, the retractable tube 6 is connected to the patient interface 4 for delivering the flow of breathable gas and the patient interface 4 is connected to a strap 230 to maintain the patient interface 4 in contact with the nares of the patient's nose. The strap 230 may be adjustable. The end 231 of the strap 230 may be threaded through a slot or tab on the patient interface 4 and adjustably fastened to itself. For example, a portion 233 of the strap 230 and the end 231 of the strap 230 may include hook and loop fasteners (e.g. VELCRO®). The end 231 of the strap 230 is fastened to the portion 233 of the strap 230 after being looped through the slot or tab provided on the patient interface 4. As another example, the end 231 of the strap 230 may be adjustably fastened to a buckle.

A stiffening element, or rigidizer, 232 may be provided at the end of the strap 230 on each side of the patient's face. The stiffening element 232 may be connected to ear engaging straps 234 which are configured to circle the ears of the patient.

The stiffening element 232 adds rigidity to support the patient interface 4. The stiffening element 232 is configured to prevent movement of the strap 230 and the patient interface 4 to prevent the patient interface 4 from disengaging the nares of the patient's nose. The stiffening element 232 also positions the ear engaging straps so as to prevent the ear engaging strap from "cutting" into the ears of the patient.

2.7.5 Headgear Configuration Fifth Embodiment

Figure 67:
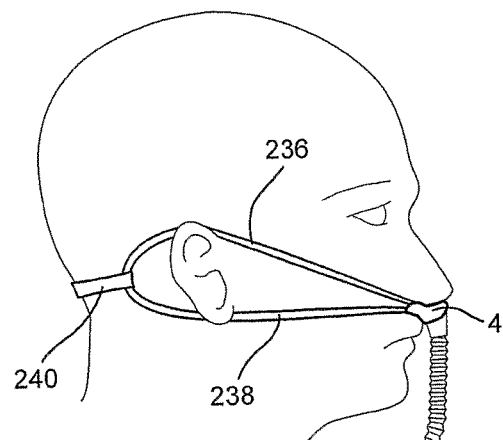
FIG. 67 schematically illustrates an interface system according to another sample embodiment.

Referring to FIG. 67, the patient interface 4 is connected to the retractable tube 6 and is maintained in contact with the nose of the patient by a top strap 236 and a bottom strap 238 which extend above and below, respectively, the ears of the patient. The top strap 236 and the bottom strap 238 are connected by a back strap 240 which is configured to extend around the back of the head of the patient. It should be appreciated that the back strap 240 may be fixed to the straps 236, 238, or may be connected to the straps 236, 238 so that the strap 240 is movable so that the position of the strap 240 with respect to the back of the patient's head may be adjusted. It should further be appreciated that the top strap 236 and the bottom strap 238 may be formed as a single strap, or may be formed as separate straps that are connected to each other at the back strap 240. For example, the straps 236, 238 may be formed of different materials, or formed of the same material but have different amounts of elasticity.

2.7.6 Headgear Configuration Sixth Embodiment

Figure 68:
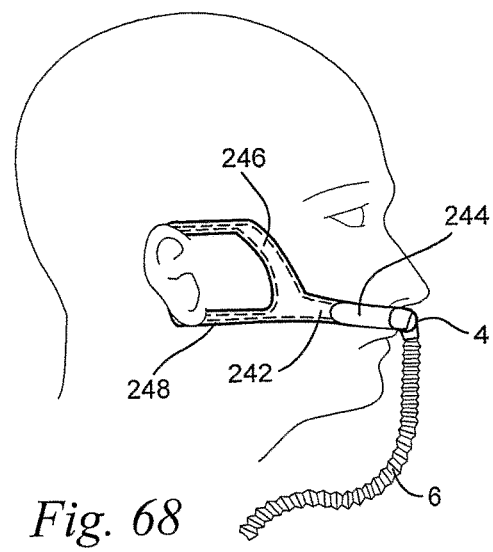
FIG. 68 schematically illustrates an interface system according to another sample embodiment.

As shown in FIG. 68, according to another embodiment, the patient interface 4 is connected to the retractable tube 6 and held in contact with the nose of the patient by straps 248 (one on each side of the patient's face, and only one shown in FIG. 68). Each strap 248 may be attached to a stiffening element, or rigidizer, 246. For example, the stiffening element 246 may be stitched to the strap 248, or adhered to the strap 248 by adhesives. The strap 248 and the stiffening element 246 may also be formed as a laminated composite.

The strap 248 may be configured to extend around the back of the patient's ears. The stiffening element 246 is configured to engage a top of the patient's ears in a manner similar to a pair of eyeglasses. The stiffening element 246 may not extend around the back of the patient's ears, although it should be appreciated that the stiffening element may be configured to do so.

The strap 248 may be made of a flexible material, for example, fabric, thermoplastic elastomer (TPE), rubber, elastic, or a combination thereof. The strap 248 may also include an end 244 that includes a fastening member, e.g. hook and loop type as described above, that is fastenable to a portion 242 of the strap 248 to permit adjustment of the fit of the headgear. It should also be appreciated that the strap end 244 may adjustable using, for example, a buckle.

2.7.7 Headgear Configuration Seventh Embodiment

Figure 69:
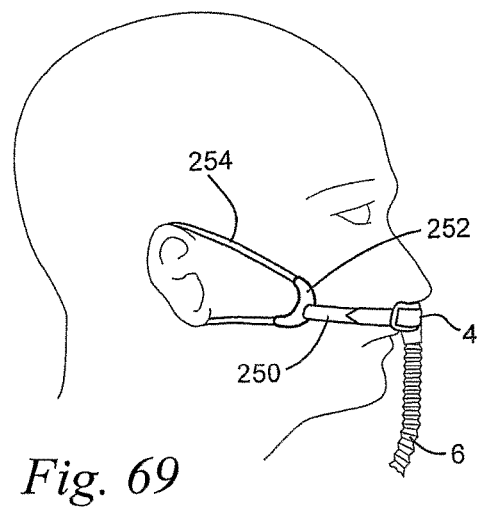
FIG. 69 schematically illustrates an interface system according to another sample embodiment.

Referring to FIG. 69, the patient interface 4 is connected to the retractable tube 6 and held in contact with the nose of the patient by a headgear including stiffening elements, or rigidizers, 252 (on each side, only one shown in FIG. 69). Each stiffening element 252 may be connected to a strap 250 that is connected to the patient interface 4, for example, by looping the flexible member 250 through a portion of the patient interface 4. Each stiffening element, or rigidizer, 252 may also be attached to an ear engaging strap 254 configured to extend around the ears of the patient to maintain the patient interface 4 in contact with the nose of the patient.

2.7.8 Headgear Configuration Eighth Embodiment

Figure 70:
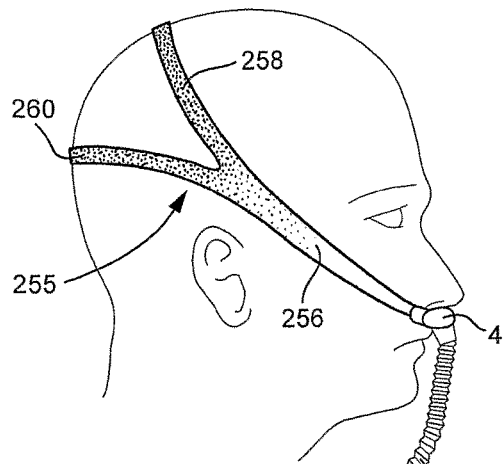
FIG. 70 schematically illustrates an interface system according to another sample embodiment.

Referring to FIG. 70, the patient interface 4 may be connected to the retractable tube 6 and held in contact with the nose of the patient by a headgear system 255 that includes a strap 256. The strap 256 extends from the patient interface 4 past and above the ears of the patient and is then bifurcated into an upper back strap 258 and a lower back strap 260.

The strap 256, including the upper back strap 258 and the lower back strap 260 may be formed of, for example, TPE, or a TPE/silicone blend. The headgear 255 may also have a varying color. As shown in FIG. 70, the upper back strap 258 and the lower back strap 260 may be formed of a darker color and gradually change color as the straps 256, 258, 260 approach the face of the patient to the point where the strap is clear. The clear portion of the strap 256 on the sides of the patient's face may provide a camouflage effect to the headgear system 2.

2.7.9 Headgear Configuration Ninth Embodiment

Figure 71:
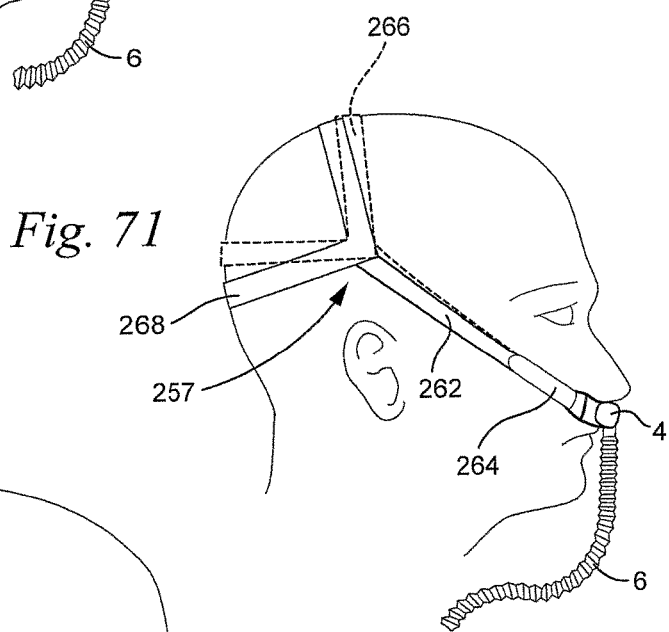
FIG. 71 schematically illustrates an interface system according to another sample embodiment.

As shown in FIG. 71, the patient interface 4 may be connected to the retractable tube 6 and held in contact with the nose of the patient by a headgear 257 comprising a strap 262 having an end 264 that is adjustably connected to the patient interface 4. The strap 262 is connected to an upper back strap 266 and a lower back strap 268 which are configured to engage the back of the patient's head to hold the patient interface 4 in contact with the nose of the patient. Although the strap 262 is shown as connected to the upper and lower back straps 266, 268, it should be appreciated that the straps 262, 266, 268 may be formed as a single one piece strap.

As shown in dashed lines, the positions of the straps 266, 268 may be adjusted to adjust the position of the strap 262. For example, adjusting the straps 266, 268 from the position shown in solid lines to the position shown in dashed lines causes the strap 262 to move upward along the side of the patient's face. The seal formed by the patient interface 4 with the nares of the patient's nose requires a component of upward force from the headgear. Adjusting the position of the strap 262 by adjusting the position of the straps 266, 268 allows the patient to achieve a comfortable fit while maintaining the seal between the patient interface 4 and the patient's nares.

2.7.10 Headgear Configuration Tenth Embodiment

Figure 72:
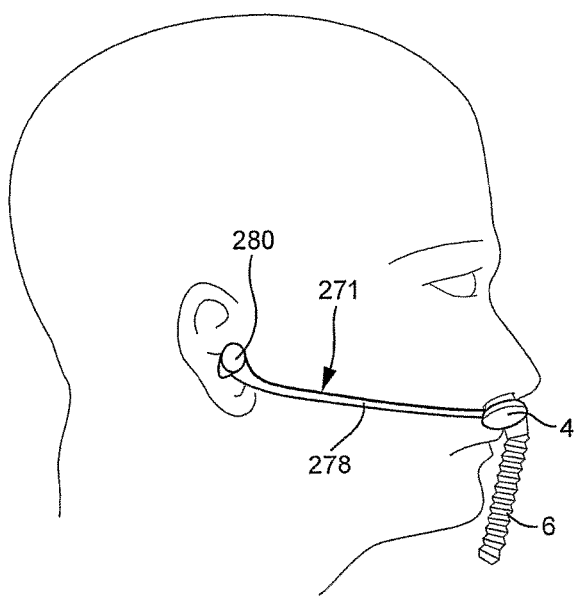
FIG. 72 schematically illustrates an interface system according to another sample embodiment.

As shown in FIG. 72, the patient interface 4 is connected to the retractable tube 6 and maintained in contact with the nose of the patient by headgear 271 comprising rigid or semi-rigid frame members 278 (only one shown) that each extend from the patient interface 4 along the sides of the patient's face. The frame member 278 may include an earplug 280 that is configured to engage in the ear of the patient to maintain the position of the frame member 278. The earplug 280 may be solid to block noise from entering the patient's ear, for example, to improve the patient's ability to fall asleep. It should also be appreciated, however, that the earplugs 280 may be hollow to allow the patient to hear while using the patient interface 4.

2.7.11 Headgear Configuration Eleventh Embodiment

Figure 73A:
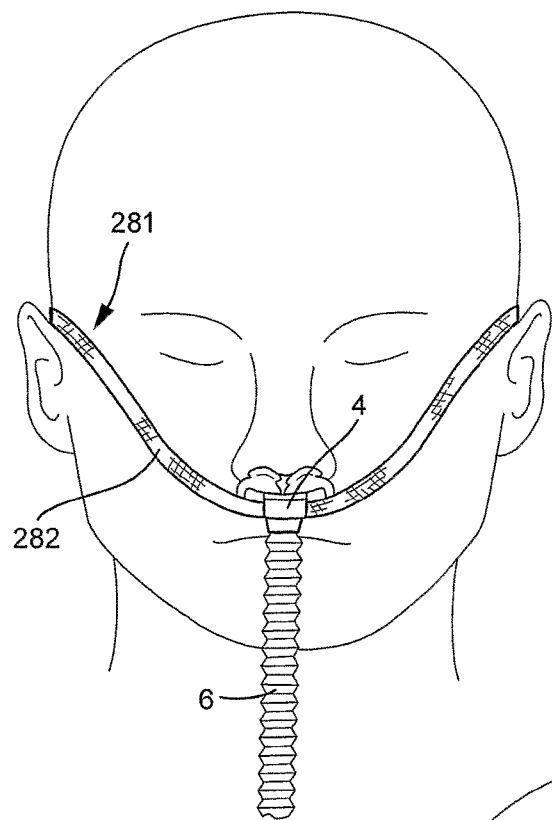
FIGS. 73*a* and 73*b* schematically illustrate an interface system according to another sample embodiment.
Figure 73B:
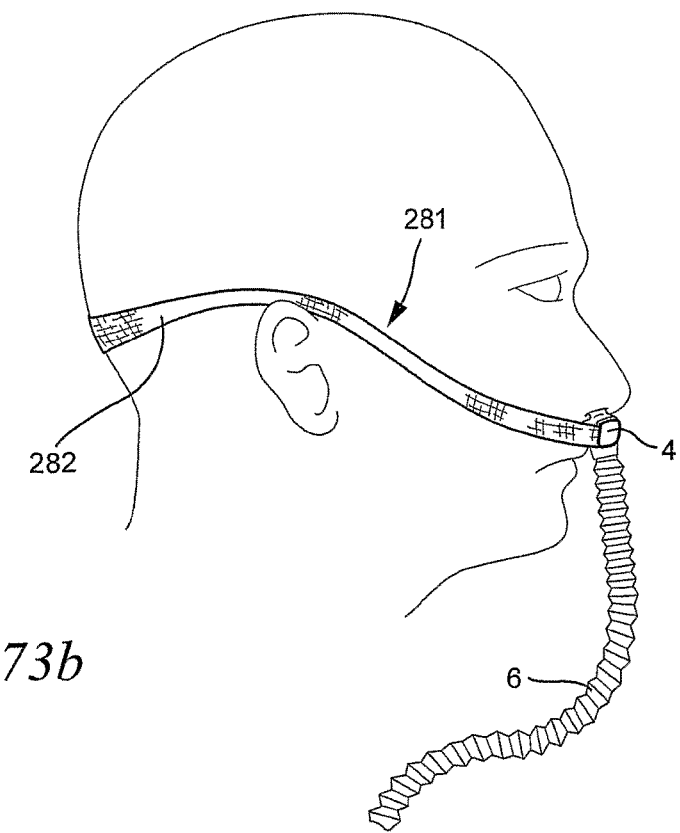

Referring to FIGS. 73a and 73b, the patient interface 4 may be connected to the retractable tube 6 and maintained in contact with the nose of the patient by headgear 281 comprising a fabric strap 282 that extends along the sides of the patient's face, over the ears of the patient, and around the back of the head of the patient. The strap may be formed of, for example, an elastic material, such as rubber, fabric, TPE, silicone or any combination thereof.

In one form of the sample embodiment, it may be desired that the headgear 281 be positioned at, or near, the occipital bone at the back of the patient's head. In this position, the patient interface 4 is not forced up into the nares, rather it is positioned at the opening of the nares and is therefore more comfortable.

Alternatively, the headgear 281 may be positioned at or near the parietal bone on the patient's head.

2.7.12 Headgear Configuration Twelfth Embodiment

Figure 74A:
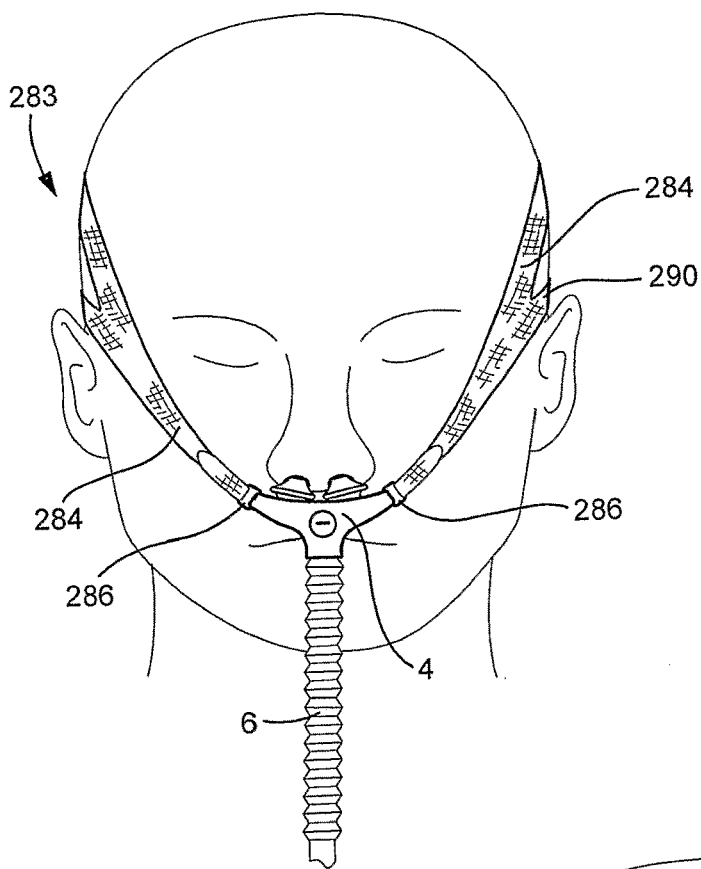
FIGS. 74*a* and 74*b* schematically illustrate an interface system according to another sample embodiment.
Figure 74B:
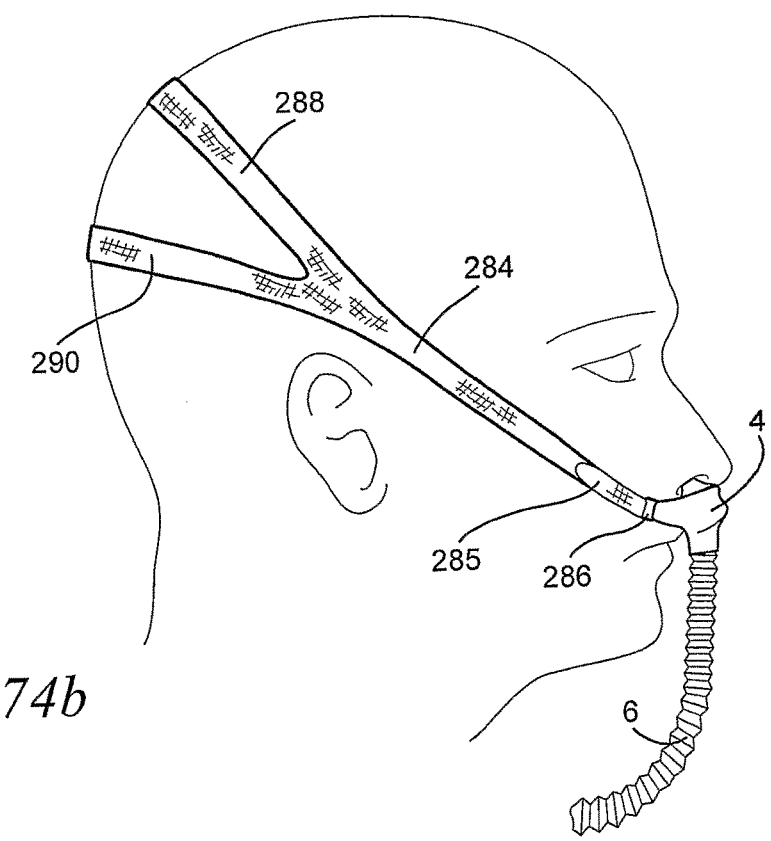

As shown in FIGS. 74a and 74b, the patient interface 4 may be connected to the retractable tube 6 and held in contact with the nose of the patient by a headgear system 283 to deliver a flow of breathable gas to the patient. The patient interface is supported by the headgear system 283 that includes a strap 284 that extends from the patient interface 4 along the sides of the patient's face above the ears of the patient. The end 285 of the strap 284 may be looped through a slot or tab 286 of the patient interface 4 and its length adjusted, for example, by hook and loop fasteners, such as VELCRO®, or a by a buckle. The strap 284 extends above and past the ears of the patient and is bifurcated into an upper back strap 288 and a lower back strap 290 that are configured to extend around the back of the patient's head.

The straps 284, 288, 290 may be formed as a one piece unitary strap, including a slot between the upper back strap 288 and the lower back strap 290, for example, as is provided on the strap of some swimming goggles. The straps 284, 288, 290 may be formed of either fabric, rubber, TPE, silicone, or combinations thereof.

The headgear 283 shown in FIGS. 74a and 74b does not include a stiffening member, or rigidizier, which permits the adjustment of the strap 284 on the patient interface 4, for example on a frame or shell, to provide a tighter, or looser, fit of the headgear than would be possible with the use of a stiffening member or rigidizer.

2.7.13 Headgear Configuration Thirteenth Embodiment

Figure 75A:
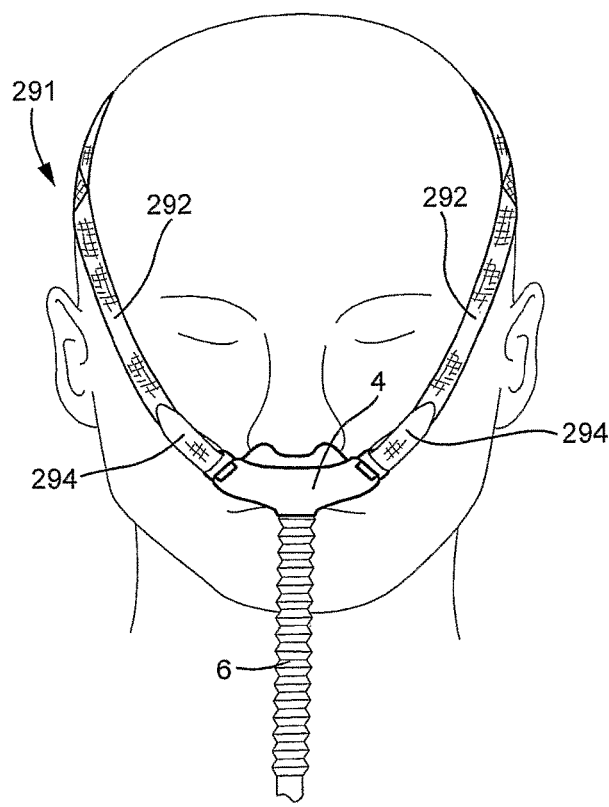
FIGS. 75*a* and 75*b* schematically illustrate an interface system according to another sample embodiment.
Figure 75B:
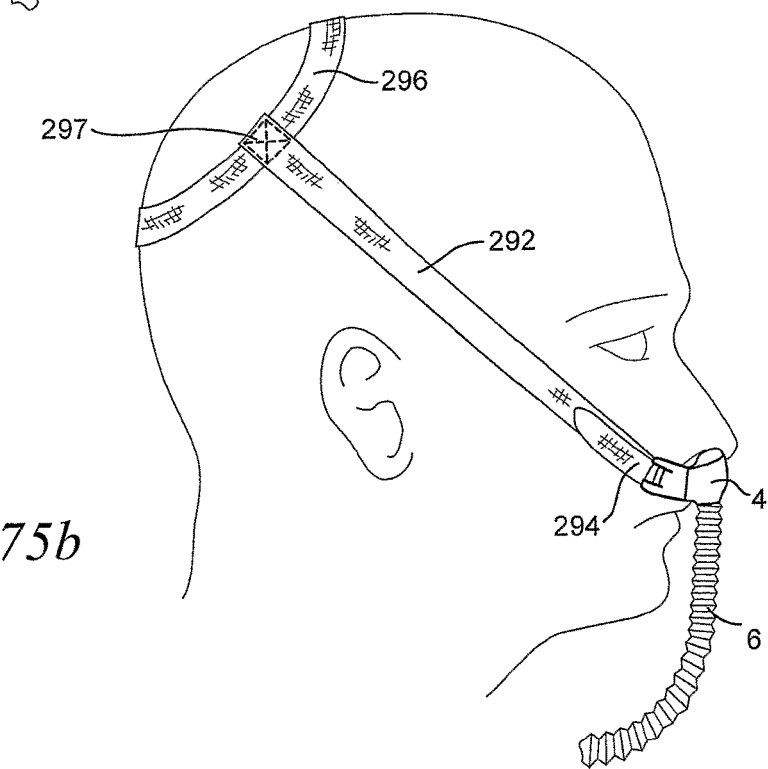

As shown in FIGS. 75a and 75b, the patient interface 4 may be connected to the retractable tube 6 and held in contact with the nose of the patient by a headgear 291 including a strap 292. The length of the strap 292 may be adjusted by adjusting the position of the end 294 of the strap 292 in a manner similar to that described above. The strap 292 extends along the sides of the patient's face above the patient's ears. A cradle 296 is connected to the strap 292 and configured to engage a back of the patient's head. The cradle 296 allows the headgear to be slid over the top of the patient's head and allows for adjustment of the straps 292 by moving the cradle 296 around the back of the patient's head for adjustment. The cradle 296 also serves as an anchoring point for the headgear. It should be appreciated that the cradle 296 may be connected to the straps 292 by, for example, stitching 297 as shown in FIG. 75b. It should also be appreciated that the cradle 296 may be connected to the straps 292 by a connector that permits adjustment of the position of the cradle 296 relative to the straps 292.

2.7.14 Headgear Configuration Fourteenth Embodiment

Figure 76A:
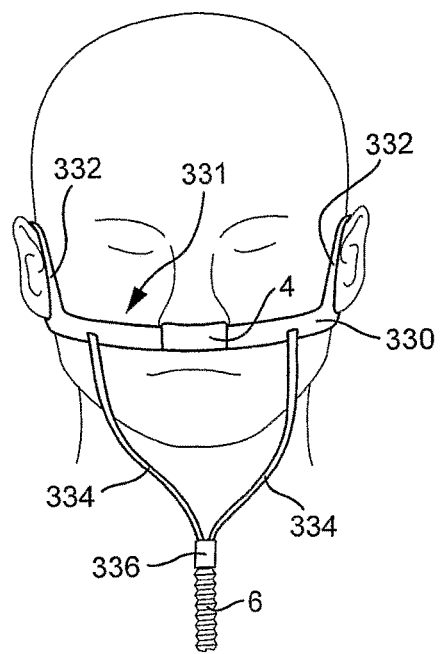
FIGS. 76*a* and 76*b* schematically illustrate an interface system according to another sample embodiment.
Figure 76B:
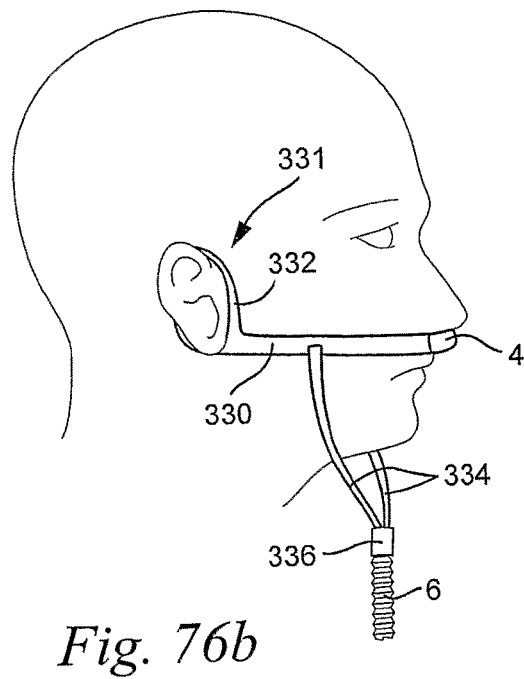

Referring to FIGS. 76a and 76b, a patient interface 4 is maintained in sealing contact with the nares of the nose of the patient by a headgear 331 that may comprise a strap 330 configured to extend across the front of the face of the patient. The strap 330 may be configured to extend across the upper lip of the patient. The strap 330 may be connected to or include ear engaging straps 332 that are configured to extend around the ears of the patient. The strap 330 may be configured as a conduit or tube and be connected to air delivery hoses, conduits or tubes 334 that are connected to a retractable tube 6 by a connector 336.

The flow of breathable gas is provided by the retractable tube 6 and the connector 336 is configured to bifurcate the flow of breathable gas into the two air delivery hoses 334 and the bifurcated flow is thereafter delivered to the front strap 330 and flows to the patient interface 4.

2.7.15 Headgear Configuration Fifteenth Embodiment

Figure 77A:
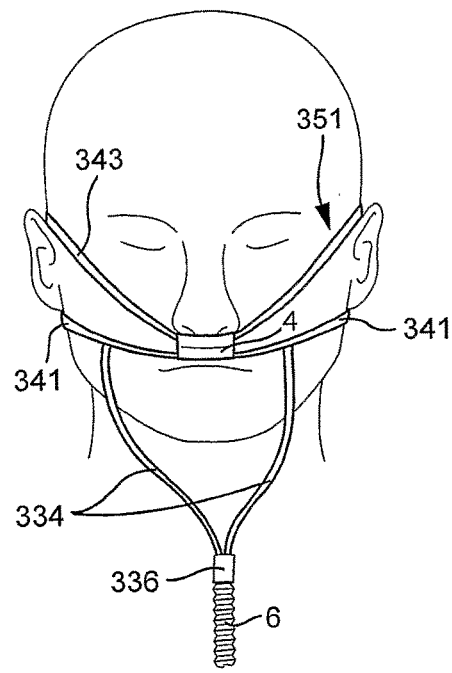
FIGS. 77*a* and 77*b* schematically illustrate an interface system according to another sample embodiment.
Figure 77B:
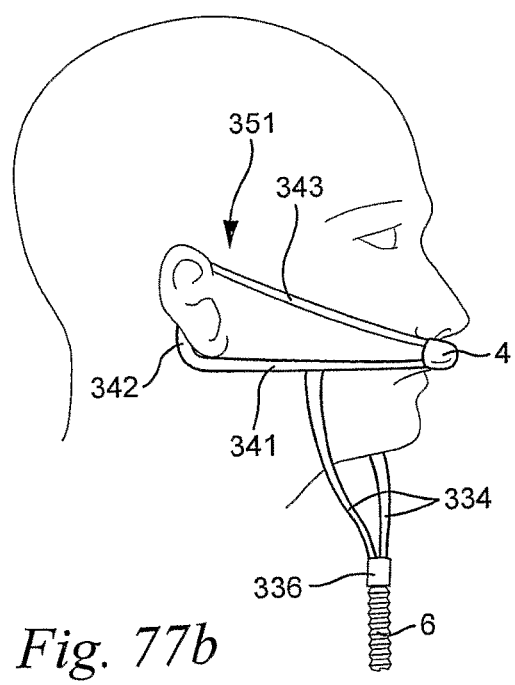

Referring to FIGS. 77a and 77b, the patient interface is held in engagement with the nose of the patient by a headgear system 351 that includes a lower strap 341 that extends below the ears of the patient and an upper strap 343 that extends above the ear of the patient. The lower strap 341 and the upper strap 343 are connected by an ear engaging strap 342.

The flow of breathable gas is delivered to the lower strap 341 which is configured as a tube or a conduit by air delivery hoses 334 that are connected by a connector 336 to a retractable tube 6 that delivers the flow of breathable gas.

2.7.16 Headgear Configuration Sixteenth Embodiment

Figure 78A:
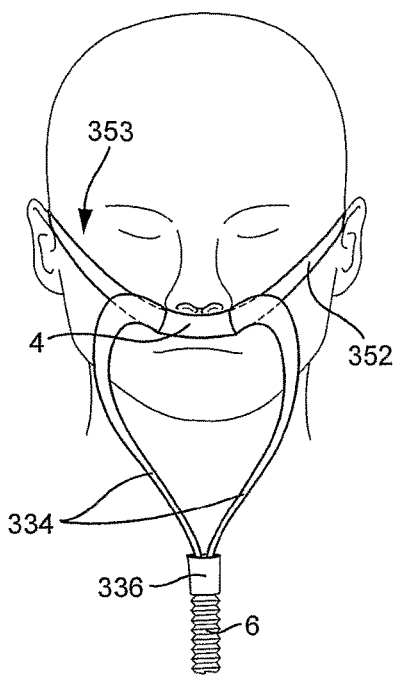
FIGS. 78*a* and 78*b* schematically illustrate an interface system according to another sample embodiment.
Figure 78B:
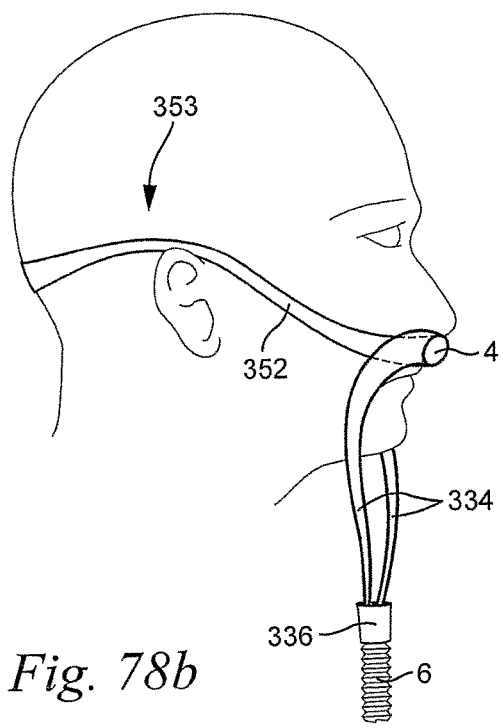

As shown in FIGS. 78a and 78b the patient interface 4 is maintained in engagement with the nose of the patient by a headgear system 353 that includes a strap 352 that is configured to extend around the head of the patient and over the ears of the patient. The flow of breathable gas is delivered to the patient interface by air delivery hoses 334 that are connected to the patient interface 4. The air delivery hoses 334 may be connected to a retractable tube 6 that delivers the flow of breathable gas by a connector 336.

2.7.17 Headgear Configuration Seventeenth Embodiment

Figure 79A:
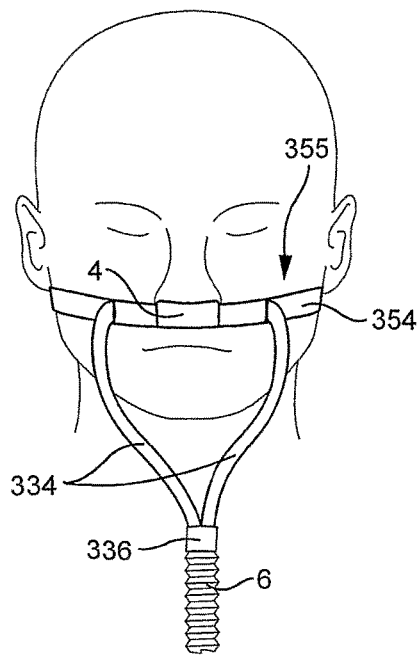
FIGS. 79*a* and 79*b* schematically illustrate an interface system according to another sample embodiment.
Figure 79B:
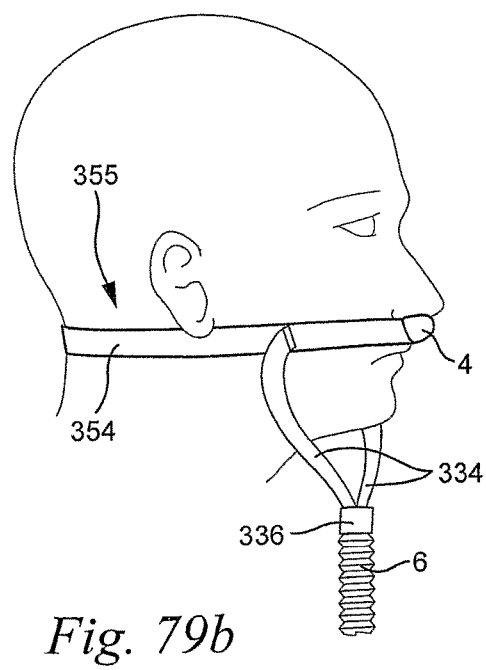

Referring to FIGS. 79*a* and 79*b*, the patient interface 4 is held in contact with the nose of the patient by a headgear system 355 that includes a strap 354 that is configured to extend around the head of the patient and below the patient's ears. The strap 354 is configured as a hose or conduit for delivering the flow of breathable gas from air delivery hoses 334 to the patient interface 4. The flow of breathable gas is delivered to the air delivery hoses 334 by a retractable tube 6 that is connected to the air delivery hoses 334 by a connector 336.

2.7.18 Headgear Configuration Eighteenth Embodiment

Figure 80:
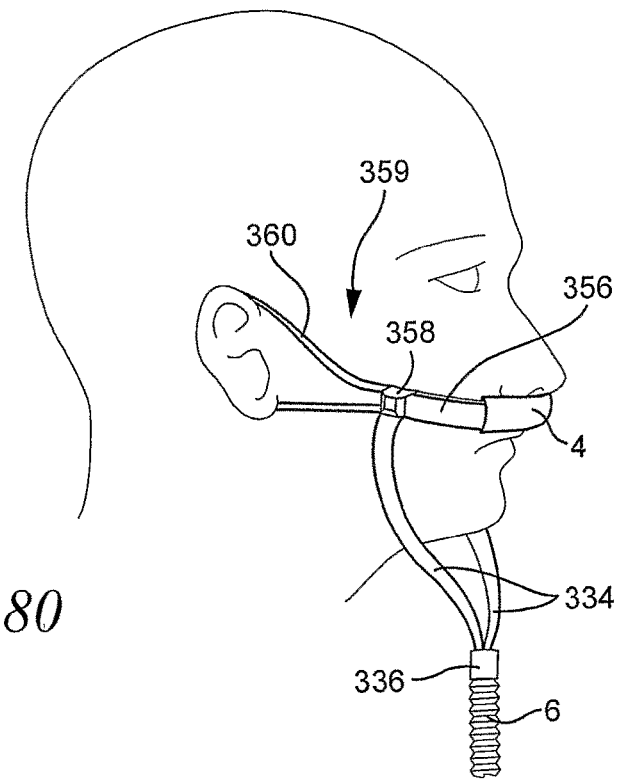
FIG. 80 schematically illustrates an interface system according to another sample embodiment.

As shown in FIG. 80, the headgear system 359 is configured to maintain the patient interface 4 in engagement with the nose of the patient and may comprise a strap 356 that is configured as a hose or conduit for delivery of the flow of breathable gas to the patient interface 4. A connector 358 is provided at each end of the strap 356 and each connector 358 is connected to an air delivery hose 334 that delivers the flow of breathable gas from a retractable tube 6 that is connected to the air delivery hoses 334 by a connector 336.

Each connector 358 is connected to an ear engaging strap 360 that is configured to extend around the ears of the patient to maintain the patient interface 4 in contact with the patient's nose.

2.7.19 Headgear Configuration Nineteenth Embodiment

Figure 81:
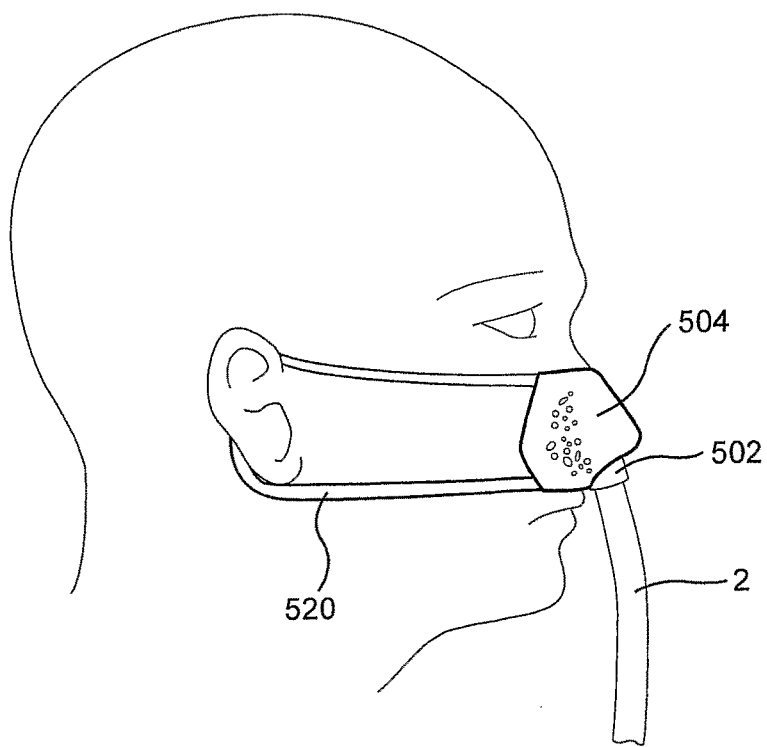
FIG. 81 schematically illustrates an interface system according to another sample embodiment.

Referring to FIG. 81, an interface comprises a cushion 504 that is configured to cover the patient's nose. The cushion 504 may be connected to straps 520 that are each configured to extend around the patient's ears. The flow of breathable gas may be delivered to the cushion by a cannula 2 that is connected to the cushion by sealing ring 502. The sealing ring 502 may swivelably connect the cannula 2 to the cushion 504.

2.7.20 Headgear Configuration Twentieth Embodiment

Figure 82:
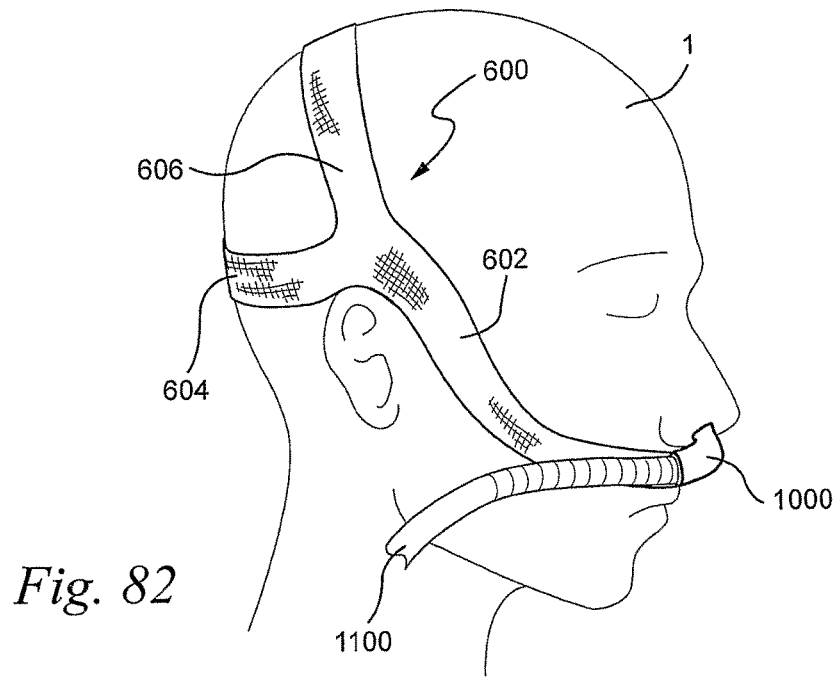
FIG. 82 schematically illustrates an interface system according to another sample embodiment.

Referring to FIG. 82, a patient interface 1000 is held in contact with the patient's face for delivery of a flow of breathable gas to the nares of the patient, for example, through the use of nasal prongs, by a headgear 600. The headgear 600 comprises a pair of side straps 602 (only one shown) that are connected by a lower back strap 604 and an upper back strap 606. A tube, or cannula, 1100 is connected to the patient interface 1000 along a side of the patient's face. The connection of the tube 1100 to the patient interface 1000 along the side of the patient's face reduces the component area in the exhalation airflow path of the patient, which reduces noise and obtrusiveness of the interface. The side connection of the tube 1100 to the patient interface 1000 also reduces the moment arm about contact with the patient's face, which improves the stability of the interface. The connection of the tube 1100 to the patient interface 1000 along the side of the patient's face also allows for the interchangeability of the tube connection from either the left side or the right side of the patient's face. Patients who prefer to sleep on a particular side may thus choose to connect the tube 1100 to the patient interface 1000 on the opposite side from which they sleep.

2.7.21 Headgear Configuration Twenty-First Embodiment

Figures 83, 84:
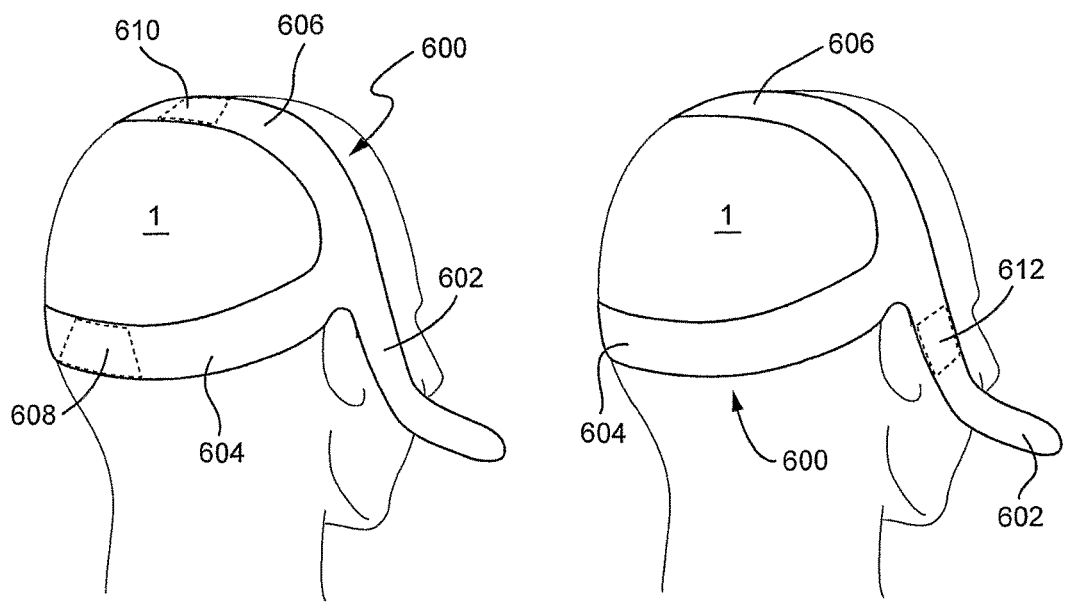
FIG. 83 schematically illustrates a headgear according to a sample embodiment.
FIG. 84 schematically illustrates a headgear according to another sample embodiment.

Referring to FIG. 83, a headgear 600 according to one sample embodiment may comprise a lower back strap adjustment 608 and an upper back strap adjustment 610 to permit adjustment of the fit of the interface. The strap adjustments 608, 610 may be hook and loop fasteners, e.g. VELCRO®, a buckle, or a ladder-lock type connector. The adjustments may be as disclosed, for example, in International Application PCT/AU2008/001557, filed Oct. 22, 2008, the entire contents of which are incorporated herein by reference. The provision of the strap adjustments 608, 610 provides good control over the positioning and fitting of the patient interface 1000.

2.7.22 Headgear Configuration Twenty-Second Embodiment

As shown in FIG. 84, according to another sample embodiment, the headgear 600 may comprise side strap adjustments 612 (only one shown) that permit adjustment of the length of the side straps 602 of the headgear 600. The provision of the side strap adjustments 612 allows for simpler adjustment of the headgear 600. As shown in FIG. 84, the lower back strap 604 and the upper back strap 606 are provided to the headgear 600 as a one piece construction. The side strap adjustments 612 may be, for example, hook and loop fasteners, buckles, or ladder-lock type connectors. The strap adjustments 612 may be as disclosed, for example, in International Application PCT/AU2008/001557, filed Oct. 22, 2008, the entire contents of which are incorporated herein by reference.

2.7.23 Headgear Configuration Twenty-Third Embodiment

Referring to FIGS. 85*a*-85*j*, an interface system according to another sample embodiment comprises a frame 660 comprising slots 662, 663 and strap guides, or connectors, 664, 665, respectively, configured to connect straps to the frame 660. As shown in FIGS. 85*d*-85*j*, a lower strap 1600 is connectable to the strap connectors 664 and side straps 1610 are connectable to the strap connectors 665.

Figure 85G:
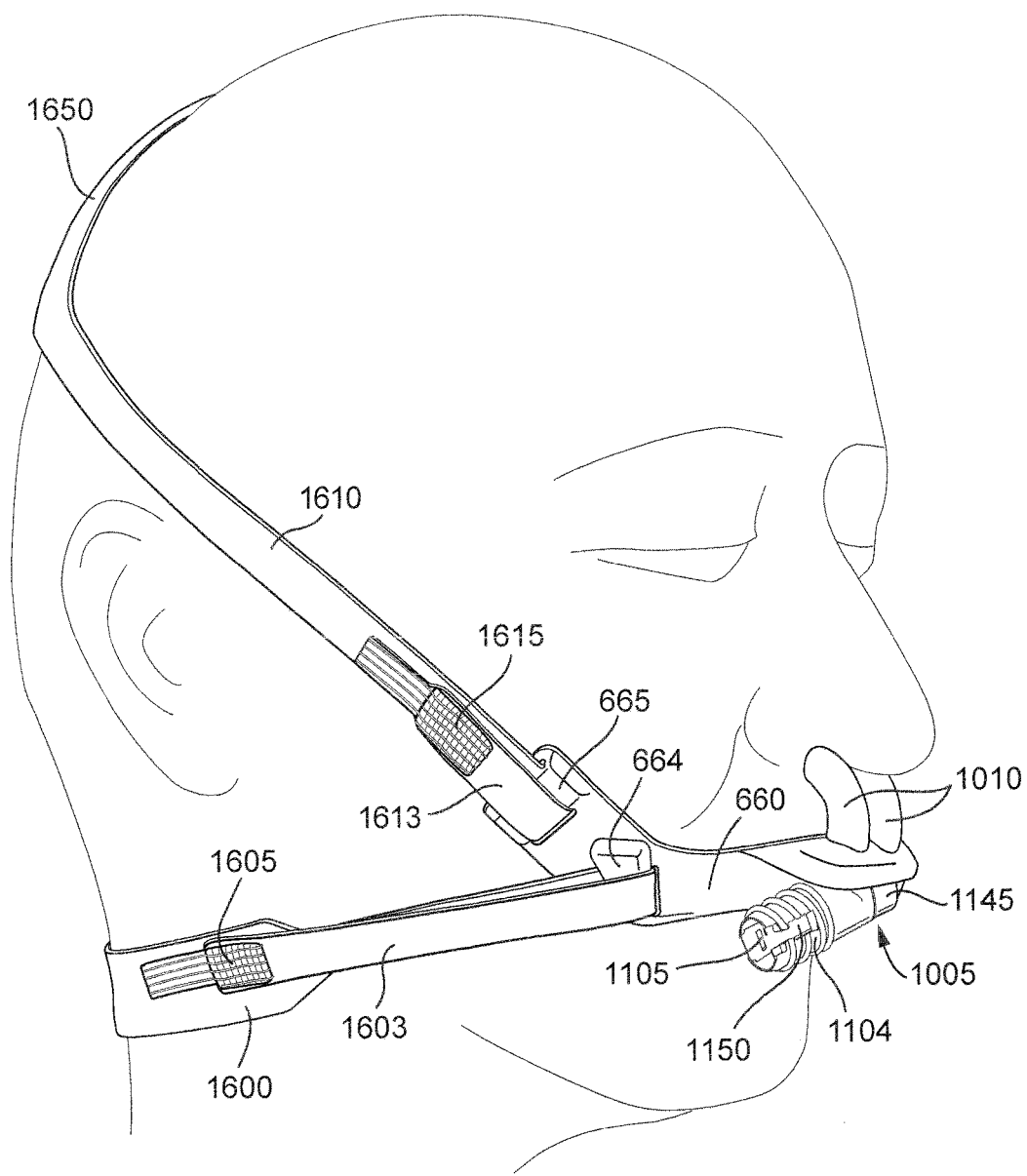
Figure 85H:
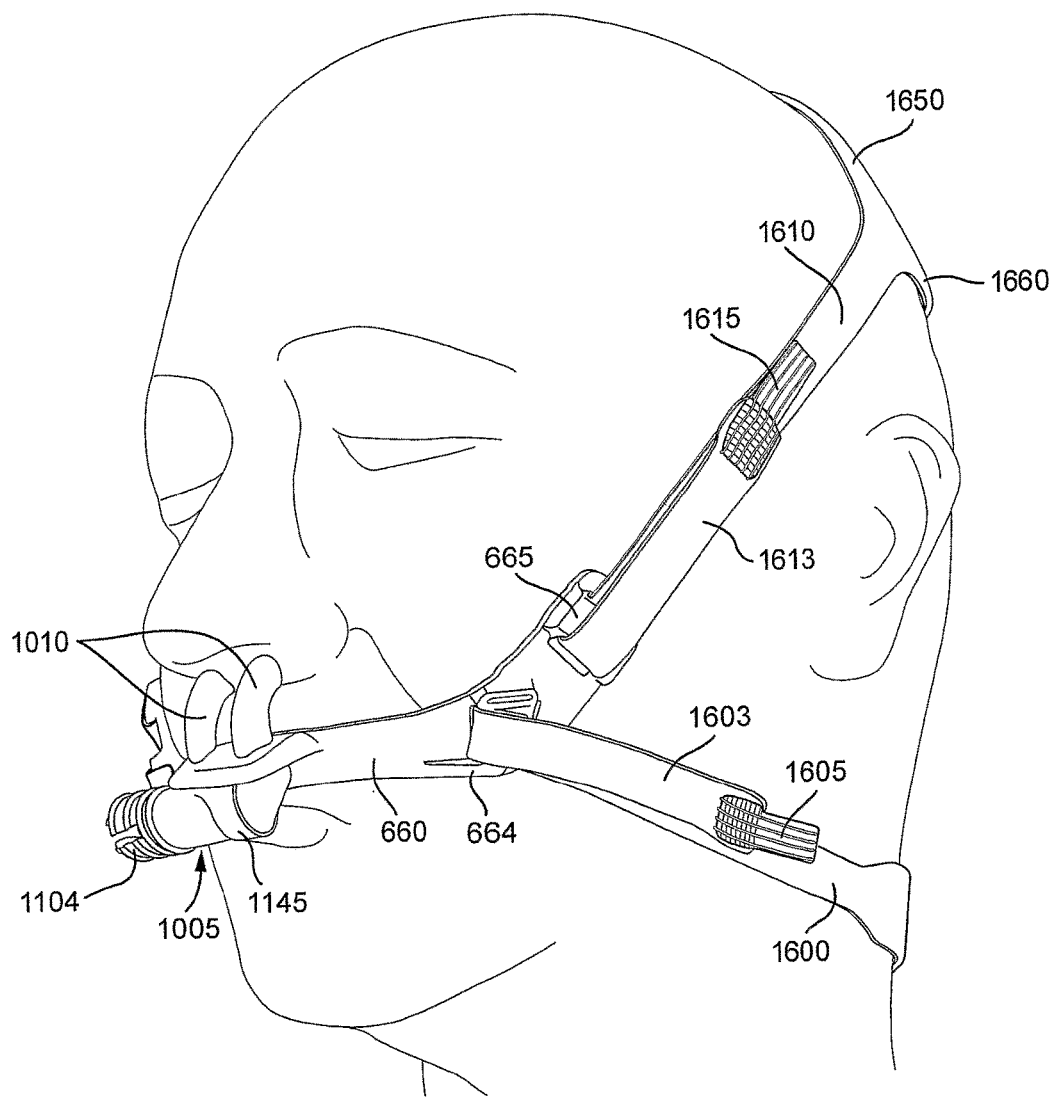
Figure 85I:
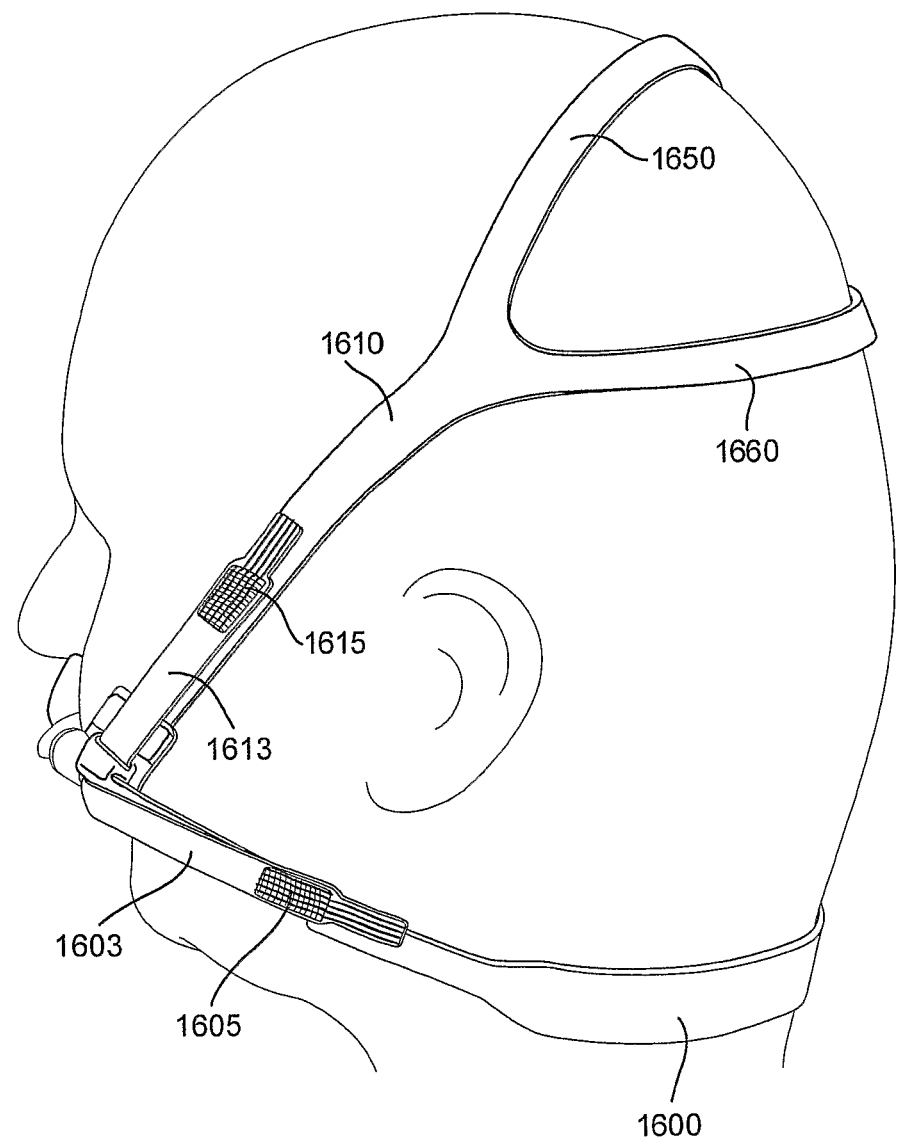

As shown in FIGS. 85*d*-85*j*, the lower strap 1600 may be connected to the strap guides or connectors 664 and extend below the patient's ears. The side straps 1610 may be connected to the strap guides or connectors 665 and extend along the sides of the patient's face above the patient's ears. Referring to FIGS. 85*g*-85*i*, the lower strap 1600 includes two ends 1603 that are looped around the strap guides or connectors 664 and secured to the lower strap by a lower strap fastener 1605. For example, the lower strap fastener 1605 may comprise hook or loop material that is engageable with loop or hook material, respectively, to fasten the ends 1603 to the lower strap 1600. As shown in, for example, FIG. 85*g*, the ends 1603 of the lower strap 1600 may have a width that is less than the remainder of the lower strap 1600 to make fastening of the fastener 1605 to the lower strap 1600 easier as precise alignment of the ends 1603 is not necessary. It should be appreciated that although the lower strap 1600 is shown having two ends 1603 comprising fasteners 1605, as shown for example in FIGS. 85*g* and 85*h*, it is possible that only one end 1603 includes a fastener 1605. The other end may be permanently connected to the strap guide or connector 664, for example by looping the end 1603 around the strap guide or connector 664 and stitching the end 1603 to the lower strap 1600. It should also be appreciated that other fasteners or connectors may be used to connect the end, or ends, to the lower strap. For example, the straps may be adjusted using a buckle(s) or ladder lock connector(s). It should also be appreciated that lower strap 1600 may be an optional accessory, i.e. the frame 660 can be efficiently stabilized with side straps 1610 and not require additional lower strap 1600.

The side straps 1610 may be connected to the frame 660 in a similar manner as the lower strap 1600. The ends 1613 of the sides straps 1610 may be looped around the strap guides or connectors 665 and the ends 1613 may be fastened to the side straps 1610 by fasteners 1615, for example hook and loop type fasteners. It should also be appreciated that other fasteners may be used, for example buckles or ladder lock connectors. It should further be appreciated that although both side straps 1610 are shown as including fasteners 1615, the interface system may include a single fastener provided to one of the side straps.

Figure 85J:
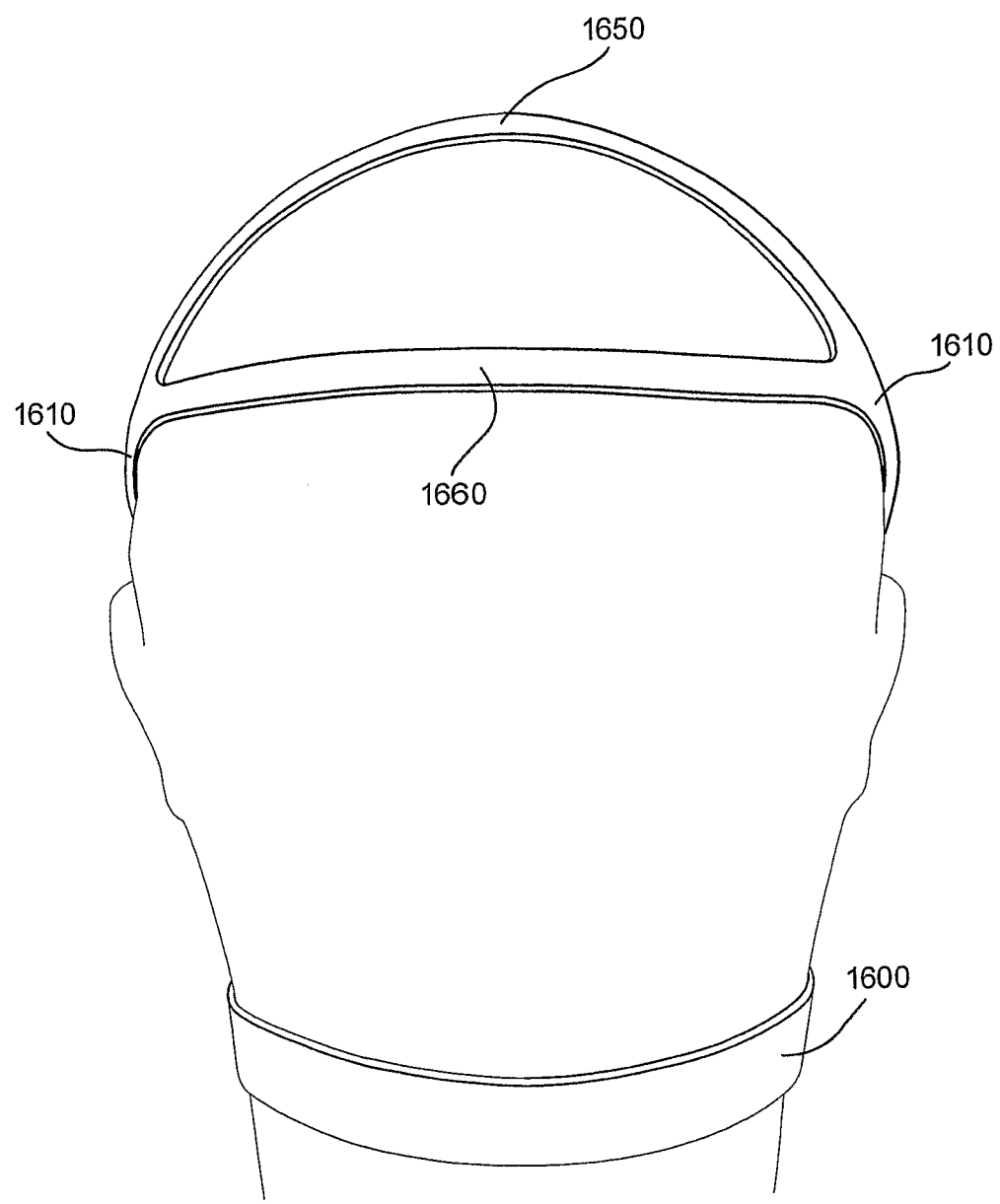

The sides straps 1610 may be connected by a rear upper strap 1650 and a rear lower strap 1660, as shown for example in FIGS. 85*h* and 85*j*. It should be appreciated that the rear straps 1650, 1660 may be integrally formed with the side straps 1610, or separately formed and then attached to the side straps 1610. It should also be appreciated that the side straps may be formed of fabric, rubber, TPE, silicone, elastic or any combination thereof. It should further be appreciated that the straps 1600, 1610, 1650, 1660 may be partially or wholly transparent, or have a varying color as described above.

3 Additional Aspects 3.1 Tube Connector

Figure 86A:
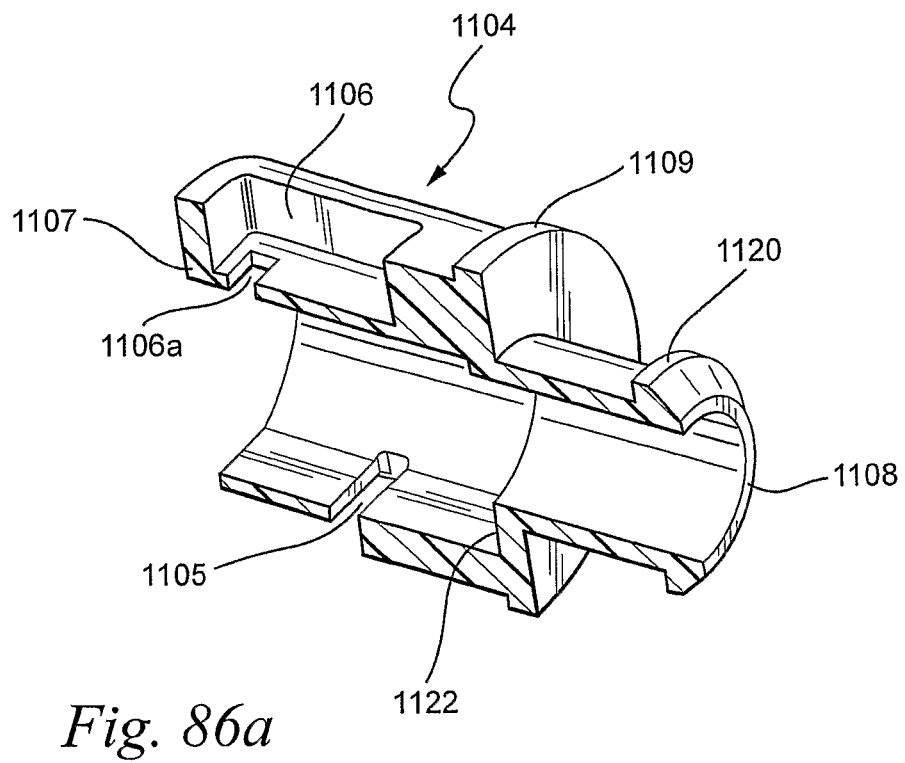
FIGS. 86*a*-86*c* schematically illustrate a tube connector according to a sample embodiment.
Figure 86B:
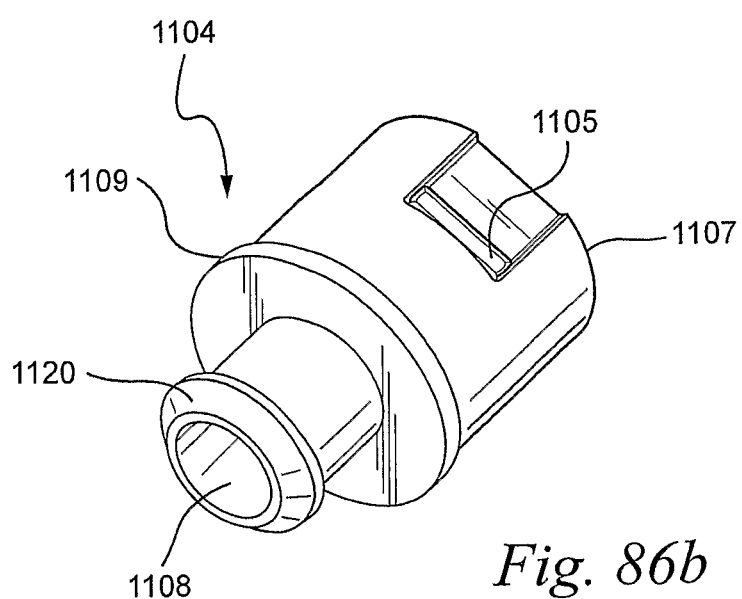
Figure 86C:
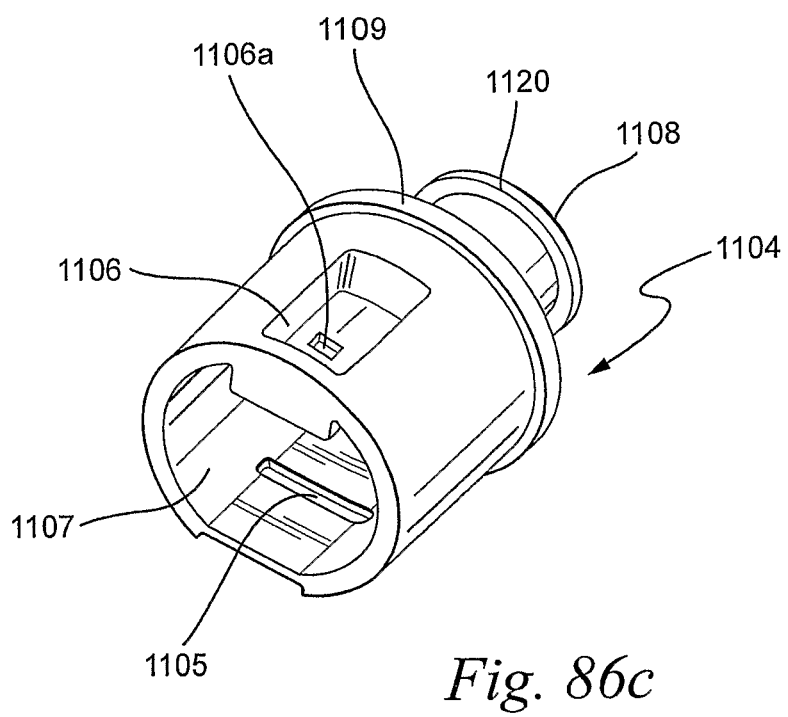

Referring to FIGS. 86*a*-86*c*, the tube connector 1104 comprises a chamfered flange 1120 at the second end 1108 to ease insertion of the tube connector 1104 into the barrel 1005 of the patient interface. As shown in FIG. 86*a*, a radial wall 1122 is formed between the first end 1107 and the second end 1108 of the tube connector 1104 corresponding to the position of the flange 1109. The radial wall 1122 presents an abrupt transition from the first end 1107 to the second end 1108 of the tube connector 1104. It should be appreciated, however, that a more gradual transition may be possible from the first end 1107 to the second end 1108.

The sensor pocket 1106 comprises a slot 1106*a* to allow leads from the sensor, or sensors, to be passed through the tube 1100 for connection to a control of either a flow generator or humidifier of a CPAP apparatus.

3.2 Pressure Port

Figure 87:
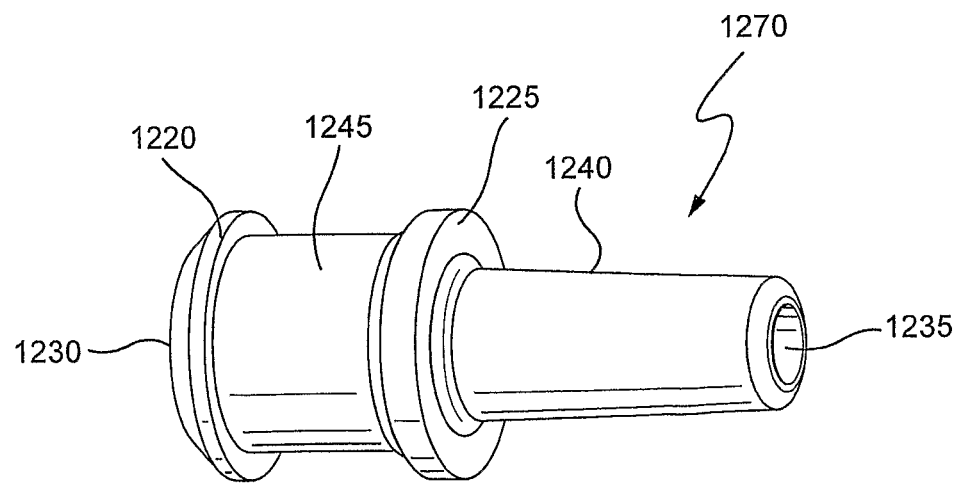
FIG. 87 schematically illustrates a pressure port according to a sample embodiment.

Referring to FIG. 87, the pressure port 1270 comprises a chamfered flange 1220 to assist in insertion of the pressure port 1270 into the end of the barrel 1005 of the patient interface. It should be appreciated that the chamfered flange may be replaced by a Luer fitting to connect the pressure port 1270 to the patient interface. The second end 1230 of the pressure port is inserted into the barrel 1005 of the patient interface and a first end 1235 is configured for connection to, for example, a pressure sensing device. The first portion 1240 of the pressure port 1270 has a smaller diameter than the second portion 1245 to permit connection of the pressure sensing device to the first end 1235 of the pressure port 1270.

3.3 Respiratory Therapy

Respiratory therapy may involve delivering a flow of breathable gas generated by a flow generator to a patient's airways. The flow of breathable gas may be delivered to the patient via a patient interface as described herein. The patient interface may form a seal with the patient's airways. The patient interface may not form a seal with the patient's airways. Respiratory therapy may also involve humidification and/or heating of the flow of breathable gas. Such respiratory therapy and apparatus are disclosed in U.S. Applications 61/059,084, filed Jun. 5, 2008, and 61/117,375, filed Nov. 24, 2008, the entire contents of each being incorporated herein by reference.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface for delivering a flow of breathable gas to a patient, the patient interface comprising:
    a barrel comprising a first end and a second end, a tubular portion extending between the first end and the second end, and a pair of nasal prongs extending from the tubular portion; and
    a tube connector configured to connect a tube or cannula to the barrel, the tube connector comprising a first end configured to be inserted into the first end or second end of the barrel, and a second end configured to be inserted into the tube or cannula, the first and second ends being divided by a flange with first and second sides, the first side being adapted to directly engage the barrel and the second side being adapted to directly engage the tube or cannula when the tube or cannula is connected to the barrel,
    wherein the barrel is rotatable relative to the tube connector and the first and second sides of the flange are substantially parallel to each other.

2. A patient interface according to claim 1, wherein the tube connector comprises a slot adjacent the second end of the tube connector configured to receive a wire extending from the tube or cannula.

3. A patient interface according to claim 1, wherein the tube connector comprises a pocket adjacent the second end of the tube connector configured to receive at least one sensor.

4. A patient interface according to claim 1, wherein the first end of the tube connector comprises a chamfered flange.

5. A patient interface according to claim 1, wherein a longitudinal axis of the tube connector is collinear with a longitudinal axis of the first end or the second end of the barrel.

6. A patient interface according to claim 1, wherein a longitudinal axis of the tube connector is offset from a longitudinal axis of the first or second end of the barrel.

7. A patient interface according to claim 1, wherein the tubular portion of the barrel is generally cylindrical.

8. A patient interface according to claim 1, wherein the tubular portion of the barrel comprises an oblique surface.

9. A patient interface according to claim 1, wherein the tubular portion of the barrel comprise a generally D-shaped cross section.

10. A patient interface according to claim 1, wherein the barrel comprises an aperture, and further comprising a plug configured to be received in the aperture to seal the aperture.

11. A patient interface according to claim 10, wherein the plug is connected to the barrel by at least one tether.

12. A patient interface according to claim 10, wherein the plug is connected to the barrel by adhesive.

13. A patient interface according to claim 1, further comprising a pressure port connected to the barrel at the first end or the second end opposite the tube connector.

14. A patient interface according to claim 1, wherein the tube connector and the barrel are formed of material having different hardnesses.

15. A patient interface according to claim 1, wherein the tube connector and the barrel are formed with different finishes.

16. A respiratory interface, comprising:
a patient interface according to claim 1; and
a headgear configured to support the patient interface in engagement with the face of the patient.

17. A respiratory interface according to claim 16, wherein the headgear comprises a pair of side straps configured to extend along opposite sides of the patient's face, an lower back strap extending between the side straps, and an upper back strap extending between the side straps.

18. A respiratory interface according to claim 17, wherein at least one of the lower back strap and the upper back strap comprises a strap adjustment.

19. A respiratory interface according to claim 18, wherein the strap adjustment comprises hook and loop fasteners, a buckle, or a ladder lock connector.

20. A respiratory interface according to claim 17, wherein at least one of the pair of side straps comprises a strap adjustment.

21. A respiratory interface according to claim 17, further comprising a rigidizer provided to each side strap.

22. A respiratory interface according to claim 21, wherein the rigidizers are connected to the barrel at the first and second ends.

23. A respiratory interface according to claim 21, wherein one of the rigidizers is integrally formed with the tube connector.

24. A respiratory interface according to claim 23, wherein the other rigidizer is integrally formed with a plug configured to be connected to the barrel.

25. A respiratory interface according to claim 17, further comprising a rigidizer extending between the side straps, the rigidizer comprising a pair of mounting bosses, each mounting boss being configured to be receive an end of the barrel of the patient interface.

26. A respiratory interface according to claim 25, wherein each mounting boss is configured to receive the tube connector.

27. A respiratory interface according to claim 16, wherein the headgear comprises side straps connected to ends of the barrel, each side strap having at least one slot configured to receive at least one additional strap.

28. A respiratory interface according to claim 27, wherein further comprising at least one strap guide extending over the at least one slot.

29. A patient interface according to claim 1, wherein the flange constitutes a thin-disc shape with first and second sides, the first side being configured to directly engage the barrel and the second side being configured to directly engage the tube or cannula.

30. A patient interface according to claim 29, wherein the flange of the tube connector is configured to engage the first end or the second end of the barrel when the tube connector is connected to the barrel.

31. A patient interface according to claim 30, wherein the tube connector further comprises an interior radial wall at a position corresponding to the position of the flange, the interior radial wall separating a first portion of the tube connector having a first diameter from a second portion of the tube connector having a second diameter.

32. A patient interface according to claim 31, wherein the first diameter is larger than the second diameter.

33. A patient interface according to claim 1, wherein the second side of the flange is configured to abut a terminal side of the tube or cannula.

34. A patient interface according to claim 1, wherein the barrel is coupled to the tube connector by way of a swivel connection.

35. A patient interface for delivering a flow of breathable gas to a patient, the patient interface comprising:
a barrel comprising a first end and a second end, a tubular portion extending between the first end and the second end, and a pair of nasal prongs extending from the tubular portion; and
a tube connector configured to connect a tube or cannula to the barrel, the tube connector comprising a first end configured to be inserted into the first end or second end of the barrel, and a second end configured to be inserted into the tube or cannula,
wherein the tube connector comprises an opening in an exterior surface of the tube connector, the opening providing communication between an interior of the tube connector and an exterior of the tube connector and being configured to receive a wire extending from the tube or cannula,
wherein the opening is covered by the tube or cannula when the tube connector is connected to the tube or cannula, and
wherein the barrel is rotatable relative to the tube connector.

36. A patient interface according to claim 35, wherein the exterior surface of the tube connector includes a recess with an opening.

37. A patient interface according to claim 36, wherein the recess is a pocket configured to receive at least one sensor.

38. A patient interface according to claim 37, wherein the pocket comprises an opening configured to receive wires from the sensor.

39. A patient interface according to claim 38, wherein the tube connector comprises a flange between the first and second end of the tube connector, the flange being configured to engage the first end or the second end of the barrel when the tube connector is connected to the barrel.

40. A patient interface according to claim 39, wherein the tube connector further comprises an interior radial wall at a position corresponding to the position of the flange, the interior radial wall extending inwardly from the exterior surface and separating a first portion of the tube connector having a first diameter from a second portion of the tube connector having a second diameter.

41. A patient interface according to claim 40, wherein the first diameter is larger than the second diameter.

42. A patient interface according to claim 35 further comprising:
the tube or cannula; and
the wire,
wherein the wire is looped through the opening in the exterior surface of the tube connector to secure the tube connector to the tube or cannula.

43. A patient interface according to claim 42, wherein the wire is at least one of a heating wire and a sensing wire.

44. A patient interface according to claim 35, wherein the wire is at least one of a heating wire and a sensing wire.

45. A patient interface according to claim 35, wherein the opening is configured to receive the wire from an interior of the tube or cannula.

\* \* \* \* \*

UNITED STATES PATENT AND TRADEMARK OFFICE
CERTIFICATE OF CORRECTION

PATENT NO. : 10,092,720 B2
APPLICATION NO. : 12/920969
DATED : October 9, 2018
INVENTOR(S) : Kooij et al.

Page 1 of 1

It is certified that error appears in the above-identified patent and that said Letters Patent is hereby corrected as shown below:

In the Claims

In Claim 17, Column 35, Line 16, "extend along opposite sides of the patient's face, an lower" should be corrected to -- extend along opposite sides of the patient's face, a lower... --

In Claim 28, Column 35, Line 51, "A respiratory interface according to claim 27, wherein further comprising at least" should be corrected to -- A respiratory interface according to claim 27, further comprising... --

Signed and Sealed this
Fourteenth Day of May, 2019

Andrei Iancu
*Director of the United States Patent and Trademark Office*